United States Patent
Brown et al.

(10) Patent No.: US 7,853,645 B2
(45) Date of Patent: Dec. 14, 2010

(54) REMOTE GENERATION AND DISTRIBUTION OF COMMAND PROGRAMS FOR PROGRAMMABLE DEVICES

(75) Inventors: Stephen J. Brown, Woodside, CA (US); David W. Brown, Bingen, WA (US)

(73) Assignee: Roy-G-Biv Corporation, Bingen, WA (US)

(*) Notice: Subject to any disclaimer, the term of this patent is extended or adjusted under 35 U.S.C. 154(b) by 235 days.

(21) Appl. No.: 10/966,848

(22) Filed: Oct. 14, 2004

(65) Prior Publication Data

US 2005/0114444 A1 May 26, 2005

Related U.S. Application Data

(63) Continuation of application No. 09/780,316, filed on Feb. 9, 2001, now abandoned, and a continuation-in-part of application No. 08/944,529, filed on Oct. 7, 1997, now abandoned.

(60) Provisional application No. 60/181,577, filed on Feb. 10, 2000.

(51) Int. Cl.
*G06F 15/16* (2006.01)
(52) U.S. Cl. .................. 709/203; 709/223; 709/224
(58) Field of Classification Search ................ 709/223, 709/224, 203, 217; 705/3
See application file for complete search history.

(56) References Cited

U.S. PATENT DOCUMENTS

| | | | |
|---|---|---|---|
| 4,078,195 | A | 3/1978 | Mathias et al. |
| 4,159,417 | A | 6/1979 | Rubincam |
| 4,199,814 | A | 4/1980 | Rapp et al. |
| 4,418,381 | A | 11/1983 | Molusis et al. |

(Continued)

FOREIGN PATENT DOCUMENTS

CA          2222235          12/1996

(Continued)

OTHER PUBLICATIONS

Remote Control and robots: an Internet Solution by John E.F. Baruch and Mark J. Cox, Computing & control Journal, Feb. 1996.*

(Continued)

*Primary Examiner*—Nathan J. Flynn
*Assistant Examiner*—Mohammad Siddiqi
(74) *Attorney, Agent, or Firm*—Michael R. Schacht; Schacht Law Office, Inc.

(57) ABSTRACT

A system for controlling a motion device. A motion control system comprises a motion control device, and a first user is associated with the motion control system. An output system is arranged to generate motion signals that may be perceived by the first user. A motion server system comprises a plurality of motion scripts associated with messages to be transmitted to the first user and a motion program web page. A processing system comprises a browser program compatible with the motion program web page. A communications system transfers data between the various systems. A second user controls the server system to form a motion message corresponding to a desired motion signal based on the at least one motion script stored by the server system. The motion control system causes the output system to generate the desired motion signal based on the motion message.

13 Claims, 13 Drawing Sheets

U.S. PATENT DOCUMENTS

| | | | |
|---|---|---|---|
| 4,422,150 A | 12/1983 | Keller et al. | |
| 4,444,061 A | 4/1984 | Mathias | |
| 4,494,060 A | 1/1985 | Chitayat et al. | |
| 4,531,182 A | 7/1985 | Hyatt | |
| 4,563,906 A | 1/1986 | Mathias | |
| 4,688,195 A | 8/1987 | Thompson et al. | |
| 4,713,808 A | 12/1987 | Gaskill | |
| 4,716,458 A | 12/1987 | Heitzman et al. | |
| 4,750,888 A | 6/1988 | Allard et al. | |
| 4,767,334 A | 8/1988 | Thorne et al. | |
| 4,769,771 A | 9/1988 | Lipmann et al. | |
| 4,782,444 A | 11/1988 | Munshi et al. | |
| 4,800,521 A | 1/1989 | Carter et al. | |
| 4,809,335 A | 2/1989 | Rumsy | |
| 4,815,011 A | 3/1989 | Mizuno et al. | |
| 4,829,219 A | 5/1989 | Penkar | |
| 4,829,419 A | 5/1989 | Hyatt | |
| 4,840,602 A | 6/1989 | Rose | |
| 4,843,566 A | 6/1989 | Gordon et al. | |
| 4,846,693 A | 7/1989 | Baer | |
| 4,852,047 A | 7/1989 | Lavallee et al. | |
| 4,853,877 A | 8/1989 | Parkhurst et al. | |
| 4,855,725 A | 8/1989 | Fernandez | |
| 4,857,030 A | 8/1989 | Rose | |
| 4,868,474 A | 9/1989 | Lancraft et al. | |
| 4,887,966 A | 12/1989 | Gellerman | |
| 4,897,835 A | 1/1990 | Gaskill | |
| 4,901,218 A | 2/1990 | Cornwell | |
| 4,912,650 A | 3/1990 | Tanaka et al. | |
| 4,923,428 A | 5/1990 | Curran | |
| 4,937,737 A | 6/1990 | Schwane et al. | |
| 4,937,759 A | 6/1990 | Vold | |
| 4,987,537 A | 1/1991 | Kawata | |
| 5,005,134 A | 4/1991 | Nakashima et al. | |
| 5,005,135 A | 4/1991 | Morser et al. | |
| 5,014,208 A | 5/1991 | Wolfson | |
| 5,020,021 A | 5/1991 | Kaji et al. | |
| 5,025,385 A | 6/1991 | Froyd | |
| 5,095,445 A | 3/1992 | Sekiguchi | |
| 5,119,318 A | 6/1992 | Paradies | |
| 5,120,065 A | 6/1992 | Driscoll et al. | |
| 5,126,932 A | 6/1992 | Wolfson et al. | |
| 5,162,986 A | 11/1992 | Graber et al. | |
| 5,168,441 A | 12/1992 | Onarheim et al. | |
| 5,175,684 A | 12/1992 | Chong | |
| 5,175,817 A | 12/1992 | Adams et al. | |
| 5,175,856 A | 12/1992 | Van Dyke et al. | |
| 5,204,599 A | 4/1993 | Hohn | |
| 5,230,049 A | 7/1993 | Chang et al. | |
| 5,245,703 A | 9/1993 | Hubert | |
| 5,247,650 A | 9/1993 | Judd et al. | |
| 5,287,199 A | 2/1994 | Zoccolillo | |
| 5,291,416 A | 3/1994 | Hutchins | |
| 5,309,351 A | 5/1994 | McCain et al. | |
| 5,329,381 A | 7/1994 | Payne | |
| 5,341,451 A | 8/1994 | Latte et al. | |
| 5,368,484 A | 11/1994 | Copperman et al. | |
| 5,377,258 A | 12/1994 | Bro | |
| 5,382,026 A | 1/1995 | Harvard et al. | |
| 5,390,304 A | 2/1995 | Leach et al. | |
| 5,390,330 A | 2/1995 | Talati | |
| 5,392,207 A | 2/1995 | Wilson et al. | |
| 5,392,382 A | 2/1995 | Schoppers | |
| 5,400,345 A | 3/1995 | Ryan, Jr. | |
| 5,402,518 A | 3/1995 | Lowery | |
| 5,405,152 A | 4/1995 | Katanics et al. | |
| 5,412,757 A | 5/1995 | Endo | |
| 5,413,355 A | 5/1995 | Gonzalez | |
| 5,417,210 A | 5/1995 | Funda et al. | |
| 5,418,964 A | 5/1995 | Conner et al. | |
| 5,438,529 A | 8/1995 | Rosenberg et al. | |
| 5,450,079 A | 9/1995 | Dunaway | |
| 5,453,933 A | 9/1995 | Wright et al. | |
| 5,459,382 A * | 10/1995 | Jacobus et al. | 318/568.11 |
| 5,465,215 A | 11/1995 | Strickland et al. | |
| 5,483,440 A * | 1/1996 | Aono et al. | 700/56 |
| 5,485,545 A | 1/1996 | Kojima et al. | |
| 5,485,620 A | 1/1996 | Sadre et al. | |
| 5,491,813 A | 2/1996 | Bondy et al. | |
| 5,493,281 A | 2/1996 | Owens | |
| 5,511,147 A | 4/1996 | Abdel-Malek | |
| 5,541,838 A | 7/1996 | Koyama et al. | |
| 5,566,278 A | 10/1996 | Patel et al. | |
| 5,566,346 A | 10/1996 | Andert et al. | |
| 5,576,727 A | 11/1996 | Rosenberg et al. | |
| 5,577,253 A | 11/1996 | Blickstein | |
| 5,596,994 A | 1/1997 | Bro | |
| 5,600,373 A | 2/1997 | Chui et al. | |
| 5,604,843 A | 2/1997 | Shaw et al. | |
| 5,607,336 A | 3/1997 | Lenensfeld et al. | |
| 5,608,894 A | 3/1997 | Kawakami et al. | |
| 5,613,117 A | 3/1997 | Davidson et al. | |
| 5,617,528 A | 4/1997 | Stechmann et al. | |
| 5,618,179 A | 4/1997 | Copperman et al. | |
| 5,623,582 A | 4/1997 | Rosenberg | |
| 5,625,820 A | 4/1997 | Hermsmeier et al. | |
| 5,625,821 A | 4/1997 | Record et al. | |
| 5,636,994 A | 6/1997 | Tong | |
| 5,652,866 A | 7/1997 | Aldred et al. | |
| 5,655,945 A | 8/1997 | Jani | |
| 5,659,753 A | 8/1997 | Murphy et al. | |
| 5,666,161 A | 9/1997 | Kohiyama et al. | |
| 5,666,264 A | 9/1997 | Chandler et al. | |
| 5,670,992 A | 9/1997 | Yasuhara et al. | |
| 5,691,897 A | 11/1997 | Brown et al. | |
| 5,691,898 A | 11/1997 | Rosenberg et al. | |
| 5,692,195 A | 11/1997 | Conner et al. | |
| 5,701,140 A | 12/1997 | Rosenberg et al. | |
| 5,704,837 A | 1/1998 | Iwasaki et al. | |
| 5,707,289 A | 1/1998 | Watanabe et al. | |
| 5,724,074 A | 3/1998 | Chainani et al. | |
| 5,733,131 A | 3/1998 | Park | |
| 5,734,373 A | 3/1998 | Rosenberg et al. | |
| 5,737,523 A | 4/1998 | Callaghan et al. | |
| 5,739,811 A | 4/1998 | Rosenberg et al. | |
| 5,746,602 A | 5/1998 | Kikinis | |
| 5,752,880 A | 5/1998 | Gabai et al. | |
| 5,754,855 A | 5/1998 | Miller et al. | |
| 5,764,155 A | 6/1998 | Kertesz et al. | |
| 5,766,077 A | 6/1998 | Hongo | |
| 5,772,504 A | 6/1998 | Machiguchi | |
| 5,790,178 A | 8/1998 | Shibata et al. | |
| 5,800,268 A | 9/1998 | Molnick | |
| 5,801,946 A | 9/1998 | Nissen et al. | |
| 5,802,365 A | 9/1998 | Kathail et al. | |
| 5,805,442 A | 9/1998 | Crater et al. | |
| 5,805,785 A | 9/1998 | Dias et al. | |
| 5,818,537 A | 10/1998 | Enokida et al. | |
| 5,821,920 A | 10/1998 | Rosenberg et al. | |
| 5,821,987 A | 10/1998 | Larson | |
| 5,822,207 A | 10/1998 | Hazama et al. | |
| 5,825,308 A | 10/1998 | Rosenberg | |
| 5,825,361 A | 10/1998 | Rubin et al. | |
| 5,828,575 A | 10/1998 | Sakai | |
| 5,832,189 A | 11/1998 | Tow | |
| 5,836,014 A | 11/1998 | Faiman, Jr. | |
| 5,846,132 A | 12/1998 | Junkin | |
| 5,848,415 A | 12/1998 | Guck | |
| 5,852,441 A | 12/1998 | Nakajima et al. | |
| 5,855,483 A | 1/1999 | Collins et al. | |
| 5,867,385 A | 2/1999 | Brown et al. | |
| 5,873,765 A | 2/1999 | Rifkin et al. | |
| 5,889,670 A | 3/1999 | Schuler et al. | |
| 5,889,672 A | 3/1999 | Schuler et al. | |

| | | | |
|---|---|---|---|
| 5,889,924 A | 3/1999 | Okabayashi et al. | |
| 5,890,963 A | 4/1999 | Yen | |
| 5,907,704 A | 5/1999 | Gudmundson et al. | |
| 5,907,831 A | 5/1999 | Lotvin et al. | |
| 5,914,876 A | 6/1999 | Hirai | |
| 5,917,840 A | 6/1999 | Cheney et al. | |
| 5,920,476 A | 7/1999 | Hennessey et al. | |
| 5,921,780 A | 7/1999 | Myers | |
| 5,924,013 A | 7/1999 | Guido et al. | |
| 5,926,389 A | 7/1999 | Trounson | |
| 5,956,484 A | 9/1999 | Rosenberg et al. | |
| 5,959,613 A | 9/1999 | Rosenberg et al. | |
| 5,960,085 A | 9/1999 | De La Huerga | |
| 5,960,168 A | 9/1999 | Shaw et al. | |
| 5,977,951 A | 11/1999 | Danieli et al. | |
| 5,984,499 A | 11/1999 | Nourse et al. | |
| 5,991,528 A | 11/1999 | Taylor et al. | |
| 5,999,964 A | 12/1999 | Murakata et al. | |
| 6,012,961 A | 1/2000 | Sharpe et al. | |
| 6,020,876 A | 2/2000 | Rosenberg et al. | |
| 6,028,593 A | 2/2000 | Rosenberg et al. | |
| 6,031,973 A | 2/2000 | Gomi et al. | |
| 6,038,493 A | 3/2000 | Tow | |
| 6,038,603 A | 3/2000 | Joseph | |
| 6,046,727 A | 4/2000 | Rosenberg et al. | |
| 6,055,579 A | 4/2000 | Goyal et al. | |
| 6,057,828 A | 5/2000 | Rosenberg et al. | |
| 6,061,004 A | 5/2000 | Rosenberg | |
| 6,065,365 A | 5/2000 | Ostler et al. | |
| 6,070,010 A | 5/2000 | Keenleyside et al. | |
| 6,078,308 A | 6/2000 | Rosenberg et al. | |
| 6,078,747 A | 6/2000 | Jewitt | |
| 6,078,968 A | 6/2000 | Lo et al. | |
| 6,080,063 A | 6/2000 | Khosla | |
| 6,083,104 A | 7/2000 | Choi | |
| 6,090,156 A | 7/2000 | MacLeod | |
| 6,100,874 A | 8/2000 | Schena et al. | |
| 6,101,425 A | 8/2000 | Govindaraj et al. | |
| 6,101,530 A | 8/2000 | Rosenberg et al. | |
| 6,104,158 A | 8/2000 | Jacobus et al. | |
| 6,125,385 A | 9/2000 | Wies et al. | |
| 6,128,006 A | 10/2000 | Rosenberg et al. | |
| 6,131,097 A | 10/2000 | Peurach et al. | |
| 6,133,867 A | 10/2000 | Eberwine et al. | |
| 6,139,177 A | 10/2000 | Venkatraman et al. | |
| 6,144,895 A | 11/2000 | Govindaraj et al. | |
| 6,147,647 A | 11/2000 | Tassoudji et al. | |
| 6,161,126 A * | 12/2000 | Wies et al. | 709/203 |
| 6,166,723 A | 12/2000 | Schena et al. | |
| 6,167,491 A | 12/2000 | McAlpine | |
| 6,169,540 B1 | 1/2001 | Rosenberg et al. | |
| 6,173,316 B1 | 1/2001 | De Boor et al. | |
| 6,191,774 B1 | 2/2001 | Schena et al. | |
| 6,195,592 B1 | 2/2001 | Schuler et al. | |
| 6,201,996 B1 | 3/2001 | Crater et al. | |
| 6,208,640 B1 | 3/2001 | Spell et al. | |
| 6,209,037 B1 | 3/2001 | Brown et al. | |
| 6,216,173 B1 | 4/2001 | Jones et al. | |
| 6,219,032 B1 | 4/2001 | Rosenberg et al. | |
| 6,219,033 B1 | 4/2001 | Rosenberg et al. | |
| 6,232,891 B1 | 5/2001 | Rosenberg | |
| 6,233,545 B1 | 5/2001 | Datig | |
| 6,242,880 B1 | 6/2001 | Hong | |
| 6,243,078 B1 | 6/2001 | Rosenberg | |
| 6,246,390 B1 | 6/2001 | Rosenberg | |
| 6,247,994 B1 | 6/2001 | DeAngelis et al. | |
| 6,252,579 B1 | 6/2001 | Rosenberg et al. | |
| 6,252,853 B1 | 6/2001 | Ohno | |
| 6,259,382 B1 | 7/2001 | Rosenberg | |
| 6,271,833 B1 | 8/2001 | Rosenberg et al. | |
| 6,278,439 B1 | 8/2001 | Rosenberg et al. | |
| 6,285,351 B1 | 9/2001 | Chang et al. | |
| 6,286,133 B1 | 9/2001 | Hopkins | |
| 6,288,705 B1 | 9/2001 | Rosenberg et al. | |
| 6,288,716 B1 | 9/2001 | Humpleman | |
| 6,290,565 B1 | 9/2001 | Galyean, III et al. | |
| 6,290,566 B1 | 9/2001 | Gabai et al. | |
| 6,292,170 B1 | 9/2001 | Chang et al. | |
| 6,292,174 B1 | 9/2001 | Mallett et al. | |
| 6,292,712 B1 | 9/2001 | Bullen | |
| 6,292,714 B1 | 9/2001 | Okabayashi | |
| 6,295,530 B1 | 9/2001 | Ritchie et al. | |
| 6,300,936 B1 | 10/2001 | Braun et al. | |
| 6,300,937 B1 | 10/2001 | Rosenberg | |
| 6,301,634 B1 | 10/2001 | Gomi et al. | |
| 6,304,091 B1 | 10/2001 | Shahoian et al. | |
| 6,305,011 B1 | 10/2001 | Safonov | |
| 6,309,275 B1 | 10/2001 | Fong et al. | |
| 6,310,605 B1 | 10/2001 | Rosenberg et al. | |
| 6,317,116 B1 | 11/2001 | Rosenberg et al. | |
| 6,317,871 B1 | 11/2001 | Andrews et al. | |
| 6,319,010 B1 * | 11/2001 | Kikinis | 434/169 |
| 6,343,349 B1 | 1/2002 | Braun et al. | |
| 6,345,212 B1 | 2/2002 | Nourse | |
| 6,353,850 B1 | 3/2002 | Wies et al. | |
| 6,366,272 B1 | 4/2002 | Rosenberg et al. | |
| 6,366,273 B1 | 4/2002 | Rosenberg et al. | |
| 6,366,293 B1 | 4/2002 | Hamilton et al. | |
| 6,374,195 B1 | 4/2002 | Li et al. | |
| 6,374,255 B1 | 4/2002 | Peurach et al. | |
| 6,400,996 B1 | 6/2002 | Hoffberg et al. | |
| 6,401,005 B1 | 6/2002 | Schwarz et al. | |
| 6,421,341 B1 | 7/2002 | Han et al. | |
| 6,425,118 B1 | 7/2002 | Molloy et al. | |
| 6,430,471 B1 | 8/2002 | Kintou et al. | |
| 6,439,956 B1 | 8/2002 | Ho | |
| 6,442,451 B1 | 8/2002 | Lapham | |
| 6,463,404 B1 | 10/2002 | Appleby | |
| 6,470,235 B2 | 10/2002 | Kasuga et al. | |
| 6,470,377 B1 | 10/2002 | Sevcik et al. | |
| 6,473,824 B1 | 10/2002 | Kreissig et al. | |
| 6,480,896 B1 | 11/2002 | Brown et al. | |
| 6,497,606 B2 | 12/2002 | Fong et al. | |
| 6,513,058 B2 | 1/2003 | Brown et al. | |
| 6,516,236 B1 | 2/2003 | Brown et al. | |
| 6,518,980 B1 | 2/2003 | DeMotte et al. | |
| 6,519,594 B1 | 2/2003 | Li | |
| 6,519,646 B1 | 2/2003 | Gupta et al. | |
| 6,523,171 B1 | 2/2003 | Dupuy et al. | |
| 6,528,963 B1 | 3/2003 | Hong | |
| 6,542,925 B2 | 4/2003 | Brown et al. | |
| 6,546,436 B1 | 4/2003 | Fainmesser et al. | |
| 6,559,860 B1 | 5/2003 | Hamilton et al. | |
| 6,560,513 B2 | 5/2003 | Krause et al. | |
| 6,560,592 B1 | 5/2003 | Reid et al. | |
| 6,571,141 B1 | 5/2003 | Brown | |
| 6,606,665 B2 | 8/2003 | Govindaraj et al. | |
| 6,615,091 B1 | 9/2003 | Birchenough et al. | |
| 6,647,328 B2 | 11/2003 | Walker | |
| 6,652,378 B2 | 11/2003 | Cannon et al. | |
| 6,658,325 B2 | 12/2003 | Zweig | |
| 6,658,627 B1 | 12/2003 | Gallup et al. | |
| 6,662,361 B1 | 12/2003 | Jackson | |
| 6,665,688 B1 | 12/2003 | Callahan, II et al. | |
| 6,668,211 B1 | 12/2003 | Fujita et al. | |
| 6,678,713 B1 | 1/2004 | Mason et al. | |
| 6,733,382 B2 | 5/2004 | Oe et al. | |
| 6,778,949 B2 | 8/2004 | Duan et al. | |
| 6,848,107 B1 | 1/2005 | Komine et al. | |
| 6,850,806 B2 | 2/2005 | Yutkowitz | |
| 6,859,671 B1 | 2/2005 | Brown | |
| 6,859,747 B2 | 2/2005 | Yutkowitz | |
| 6,865,499 B2 | 3/2005 | Yutkowitz | |
| 6,879,862 B2 | 4/2005 | Brown et al. | |
| 6,885,898 B1 | 4/2005 | Brown et al. | |
| 6,889,118 B2 | 5/2005 | Murray, IV et al. | |

| | | |
|---|---|---|
| 6,892,145 B2 | 5/2005 | Topka et al. |
| 6,920,408 B2 | 7/2005 | Yutkowitz |
| 6,922,826 B2 | 7/2005 | Bates et al. |
| 6,941,543 B1 | 9/2005 | Brown et al. |
| 6,944,584 B1 | 9/2005 | Tenney et al. |
| 7,024,255 B1 | 4/2006 | Brown et al. |
| 7,024,666 B1 | 4/2006 | Brown |
| 7,031,798 B2 | 4/2006 | Brown et al. |
| 7,035,697 B1 | 4/2006 | Brown |
| 7,076,336 B2 | 7/2006 | Murray, IV et al. |
| 7,113,833 B1 | 9/2006 | Brown et al. |
| 7,137,107 B1 | 11/2006 | Brown |
| 7,137,891 B2 | 11/2006 | Neveu et al. |
| 7,139,843 B1 | 11/2006 | Brown et al. |
| 7,216,179 B2 | 5/2007 | Ott et al. |
| 7,302,676 B2 | 11/2007 | Schmitt et al. |
| 2001/0020944 A1 | 9/2001 | Brown |
| 2001/0029443 A1 | 10/2001 | Miyahira |
| 2001/0032268 A1 | 10/2001 | Brown |
| 2001/0032278 A1 | 10/2001 | Brown et al. |
| 2001/0037492 A1 | 11/2001 | Holzmann |
| 2002/0044297 A1 | 4/2002 | Tanaka |
| 2002/0049776 A1 | 4/2002 | Aronoff et al. |
| 2002/0129333 A1 | 9/2002 | Chandhoke et al. |
| 2002/0156872 A1 | 10/2002 | Brown |
| 2002/0163909 A1 | 11/2002 | Sarkinen et al. |
| 2002/0165627 A1 | 11/2002 | Brown et al. |
| 2002/0165708 A1 | 11/2002 | Kumhyr |
| 2002/0173877 A1 | 11/2002 | Zweig |
| 2002/0177453 A1 | 11/2002 | Chen et al. |
| 2003/0033150 A1 | 2/2003 | Balan et al. |
| 2003/0037117 A1 | 2/2003 | Tabuchi |
| 2003/0061023 A1 | 3/2003 | Menezes et al. |
| 2003/0069998 A1 | 4/2003 | Brown et al. |
| 2003/0093187 A1 | 5/2003 | Walker |
| 2003/0165227 A1 | 9/2003 | De Beer |
| 2003/0171846 A1 | 9/2003 | Murray, IV et al. |
| 2003/0230998 A1 | 12/2003 | Miyaji et al. |
| 2004/0019683 A1 | 1/2004 | Lee et al. |
| 2004/0025150 A1 | 2/2004 | Heishi et al. |
| 2004/0044794 A1 | 3/2004 | Srinivasan |
| 2005/0114444 A1 | 5/2005 | Brown et al. |
| 2005/0132104 A1 | 6/2005 | Brown |
| 2006/0064503 A1 | 3/2006 | Brown et al. |
| 2006/0206219 A1 | 9/2006 | Brown et al. |
| 2006/0241811 A1 | 10/2006 | Brown et al. |
| 2006/0247801 A1 | 11/2006 | Brown et al. |
| 2006/0282180 A1 | 12/2006 | Brown et al. |
| 2007/0022194 A1 | 1/2007 | Brown et al. |
| 2008/0275576 A1 | 11/2008 | Brown et al. |
| 2008/0275577 A1 | 11/2008 | Brown et al. |
| 2009/0030977 A1 | 1/2009 | Brown et al. |
| 2009/0063628 A1 | 3/2009 | Brown et al. |
| 2009/0082686 A1 | 3/2009 | Brown et al. |
| 2009/0157199 A1 | 6/2009 | Brown et al. |
| 2009/0157807 A1 | 6/2009 | Brown et al. |
| 2009/0271007 A1 | 10/2009 | Brown et al. |
| 2010/0005192 A1 | 1/2010 | Brown et al. |
| 2010/0064026 A1 | 3/2010 | Brown et al. |

FOREIGN PATENT DOCUMENTS

| | | |
|---|---|---|
| CA | 2586401 | 12/1996 |
| CA | 2389183 | 5/2001 |
| CA | 2625283 | 5/2001 |
| CA | 2586401 | 10/2009 |
| EP | 0442676 A2 | 8/1991 |
| EP | 0 281 427 B1 | 8/1992 |
| EP | 0508912 A1 | 10/1992 |
| EP | 0 583 908 A2 | 2/1994 |
| EP | 1 260 891 A1 | 5/1995 |
| EP | 821522 A2 | 1/1998 |
| EP | 0829039 | 3/1998 |
| EP | 0275826 A1 | 7/1998 |
| EP | 1 174 779 A1 | 4/2000 |
| EP | 1560093 | 8/2005 |
| EP | 1678589 | 7/2006 |
| EP | 1690173 | 8/2006 |
| EP | 2081094 | 7/2009 |
| GB | 2 244 896 A | 12/1991 |
| JP | 59 228473 | 6/1983 |
| JP | 06-168157 | 6/1994 |
| JP | 8161335 A | 6/1996 |
| JP | 11506234 | 6/1999 |
| JP | 2000020114 A | 1/2000 |
| JP | 2000155693 | 6/2000 |
| JP | 2003513348 | 4/2003 |
| JP | 2004078904 | 3/2004 |
| JP | 2007102796 | 4/2007 |
| JP | 2008159046 | 7/2008 |
| WO | WO 92/11731 | 7/1992 |
| WO | WO 93/08654 | 4/1993 |
| WO | WO 95/07504 | 3/1995 |
| WO | 96/387769 | 5/1995 |
| WO | 0067081 | 11/2000 |
| WO | 0131408 | 5/2001 |
| WO | 0163431 | 8/2001 |
| WO | 02054184 | 7/2002 |
| WO | 02071241 | 9/2002 |
| WO | 03019397 | 3/2003 |
| WO | 2005031542 | 4/2005 |
| WO | 2005048086 | 5/2005 |

OTHER PUBLICATIONS

SEMI; "SEMI E4-0699 SEMI Equipment Communications Standard 1 Message Transfer (SECS-I)", Jan. 2, 1980.

SEMI; "SEMI E5-1104 SEMI Equipment Communications Standard 2 Message Content (SECS-II)", 1982, pp. 1-9.

Stewart, Schmitz, Khosla; "Implementing Real-Time Robotic Systems Using CHIMERA II", IEEE, 1990, pp. 254-255, Sections 3.1 and 3.2.

Paidy, Reeve; "Software Architecture for a Cell Controller", IEEE, 1991, pp. 344-349.

Payton, D., Bihari, T.; "Intelligent Real-Time Control of Robotic Vehicles", ACM, Aug. 1, 1991, pp. 49-63, vol. 34, No. B.

SEMI; "SEMI E30-1103 General Model For Communications and Control of Manufacturing Equipment (GEM)", 1992.

Blasvaer, Pirjanian; "An Autonomous Mobile Robot System", Jun. 8, 1994, pp. 52-61 and 122-124, Chapters 4 and 6.7.

Pirjanian, Christensen; "Hierarchical Control for Navigation Using Heterogeneous Models", Nov. 1, 1995, 19 pages, Denmark.

Xiaowei, M., Xiaoli, L., Yulin, M., Hegao, C.; "Real-time Self-reaction of Mobile Robot with Genetic Fuzzy Neural Network in Unknown Environment", Proceedings of the IEEE Intl. Conf. on Sys, Man, and Cybernetics, 1998, vol. 4.

GLOBALSPEC; "About CNC Controllers", 1999, Internet Location: http://motion-controls.globalspec.com/LearnMore/Motion_Controls/Machine_Motion_Controllers/CNC_Controllers.

Brown, K.; "SOAP for Platform Neutral Interoperability", Sep. 1, 2000, 16 pages.

OPC Foundation; "OPC Overview", Oct. 27, 1998, Version 1.0.

OPC Foundation; "OLE for Process Control, Data Access Standard", Jul. 30, 1997, pp. 1-168, UPDATED, version 1.0A.

Baruch, J., Cox, M.; "Remote control and robots: an Internet solution", Computing and Control Engineering Journal, Feb. 1, 1996.

Microsoft Corporation; "Dynamic Data Exchange"; *Windows 3.1 SDK Guide to Programming*; 1992, 1993; Chapter 22; 21 pages.

Microsoft Corporation; "Dynamic Data Exchange Management Library"; *Win32 SDK: Prog. Ref.* vol. 2; 1992, 1993; Chapter 77; 26 pages.

Microsoft Corporation; "Network Dynamic Data Exchange"; *Windows for Workgroups 3.1 Resource Kit*; 1992, 1993; Chapter 11; 19 pages.

Fitzgerald, M., Barbera, A.; "A Low-Level Control Interface for Robot Manipulators", Robotics and Computer-Integrated Manufacturing, 1985, vol. 2, No. 3/4, pp. 201-213.
Rembold, J., Blume, C., Frommherz, B.; "The Proposed Robot Software Interfaces SRL and IRDATA", Robotics and Computer-Integrated Manufacturing, 1985, vol. 2, No. 3/4, pp. 219-225.
Taylor, R.; "A General Purpose Control Architecture for Programmable Automation Research", IBM T.J. Watson Research Center, 1986, pp. 165-173.
Hayward, V., Paul, R.; "Robot Manipulator Control under Unix RCCL: A Robot Control "C" Library", The International Journal of Robotics Research, 1986, vol. 5, No. 4, pp. 94-111.
Lloyd, J., Parker, M., Mcclain, R.; "Extending the RCCL Programming Environment to Multiple Robots and Processors", IEEE, 1988, pp. 465-469.
Mangaser, A., Wang, Y., Butner, S.; "Concurrent Programming Support for a Multi-Manipulator Experiment on RIPS", IEEE, 1989, pp. 853-859.
Tesar, D., Butler, M.; "A Generalized Modular Architecture for Robot Structures", American Society of Mechanical Engineers, Jun. 1, 1989, pp. 91-118.
Bloom, H.; "Software and Computer Integrated Manufacturing", 1990, pp. 1-14.
Kasahara, T.; "Map 2.0 Entering the Practical Use Period in the Cim Era: Map 3.0 MMS Architecture and Mounting Method", Ohmsha Ltd., Mar. 1, 1990, pp. 57-62, Computer and Network LAN vol. 8, No. 3.
Miller, D., Lennox, C.; "An Object-Oriented Environment for Robot System Architectures", IEEE Control Systems, Feb. 1, 1991, pp. 14-23.
Yared, W., Sheridan, T.; "Plan Recognition and Generalization in Command Languages with Application to Telerobotics", IEEE, Mar. 1, 1991, vol. 21, No. 2, pp. 327-338.
Senehi, M., Wallace, S., Barkmeyer, E., Ray, S., Wallace, E.; "Control Entity Interface Document", Jun. 1, 1991, pp. 1-38.
Smith, M.; "An Environment for More Easily Programming a Robot", International Conference on Robotics and Automation, May 1, 1992, pp. 10-16.
Nielsen, L., Trostmann, S., Trostmann, E.; "Robot Off-line Programming and Simulation As a True CIME-Subsystem", International Conference on Robotics and Automation, May 1, 1992, pp. 1089-1094.
Albus, J.; "A Reference Model Architecture for Intelligent Systems Design", NIST, 1993, pp. 1-38.
Wallace, S., Senehi, M., Barkmeyer, E., Ray, S., Wallace, E.; "Control Entity Interface Specification", Sep. 1, 1993, pp. 10-20.
Proctor, F., Damazo, B., Yang, C., Frechette, S.; "Open Architectures for Machine Control", NIST, 1994, pp. 1-17.
US Department of Energy; "Robotic Technology Development Program", Feb. 1, 1994, pp. 1-114.
Miller, D.; "Using Generic Tool Kits to Build Intelligent Systems (AIAA 94-1214)", Sandia National Laboratories, Mar. 9, 1994, pp. 1-9.
Sakai, K.; "Object Orientation and C++ Language: Facts of Object-Oriented Programming", CQ Publishing Co., Ltd., Jun. 1, 1994, vol. 20, No. 6, pp. 83-93.
Hori, K.; "Protocol Conversion Software That Makes Possible Communication between Different Types of Field Devices", Cosmo Technica, Sep. 1, 1994, pp. 1-12.
Daiyo, M.; "The Full Color Era Has Arrived with Scanner and Printer Development", NIKKEI BYTE, Oct. 1, 1994, No. 130, pp. 160-172.
Senehi, M., Kramer, T., Michaloski, J., Quintero, R., Ray, S., Rippey, W., Wallace, S.; "Reference Architecture for Machine Control Systems Integration: Interim Report", Oct. 20, 1994, pp. 1-52.
Putnam, F.; "The WinSEM OLE Messaging Architecture Working Paper", Labtech, Dec. 1, 1994.
Fanuc Ltd.; "FANUC Robot i series Product Manual", 1995, pp. 1-8.
Koizumi, A.; "Pursuing Design Development with a Focus on Compatibility and Permeability with Incorporation of Worldwide Standard Specifications", Instrumentation: Instrumentation and Control Engineering, May 1, 1995, vol. 38, No. 5, pp. 58-62.
GE FANUC; "TCP/IP Ethernet Communications for the Series 90-70 PLC", 1996.

Burchard, R., Feddema, J.; "Generic Robotic and Motion Control API Based on GISC-Kit Technology and CORBA Communications", Sandia National Laboratories, Apr. 1, 1996, pp. 712-717.
Schneeman, R.; "Device Driver Development for Microsoft Windows NT: Accessing Motion Control Hardware Using a Multimedia Framework", NIST, Oct. 1, 1996, pp. 1-43.
Suzuki, T., Fujii, T., Yokota, K., Asama, H., Kaetsu, H., Endo, I.; "Teleoperation of Multiple Robots through the Internet", Nov. 14, 1996, pp. 84-88.
Kapoor, C.; "A Reusable Operational Software Architecture for Advanced Robotics", UMI, Dec. 1, 1996, pp. vi-vii, 1-79, 111-253, 302-368 (ch1, ch2, ch4, ch5 and ch7).
Jennings, R.; "Special Edition Using Access 97, Second Edition", Que, Oct. 9, 1997, Chapter 25.
Hall, E.; "Intelligent Robot Trends for 1998", University of Cincinnati, 1998, pp. 1-13.
Siemens AG Automation and Drives; "IT-Solutions for Machine Tools: SinCOM Computer Link SINUMERIK 840D/810D Description of Functions", 1998, 272 pages.
Claverie, S.; "Working the 'NET: Developing Applications with Internet Information Server and Visual Basic Active X Controls", Loyola University, Sep. 1, 1998, pp. 158-162.
Ge Fanuc; "Open Systems (Type II High Speed Serial Bus Setup for 32-Bit Windows 95 and Windows NT Applications)", Oct. 1, 1998.
Ge Fanuc; "Cimplicity HMI OPC Server", Apr. 1, 1999.
Platt, D.; "Understanding COM+: Events", Microsoft Press, Jun. 30, 1999, pp. 149-182.
Platt, D.; "Understanding COM+: Security", Microsoft Press, Jun. 30, 1999, pp. 44-57.
JARA; "Specifications of ORiN (Ver. 0.5)", Aug. 1, 1999.
Jeppsson, J.; "Sensor Based Adaptive Control and Prediction Software - Keys to Reliable HSM", The Boeing Company, Nov. 3, 1999.
LEGO; "Lego MindStorms RCX 2.0 Firmware Command Overview", Jul. 4, 2000.
Ott, M., Reininger, D., Makwana, D., Singh, M.; "U.S. Publication No. 2002/0150093", USPTO, Aug. 16, 2000.
Chen; "U.S. Publication No. 2002/0177453 A1", USPTO, Nov. 15, 2000.
Nacsa, J.; "Comparison of Three Different Open Architecture Controllers", 2001.
Evolution Robotics, Inc.; "ERSP 3.0 - Getting Started Guide", 2001.
Evolution Robotics, Inc.; "ERSP 3.0 - Robotic Development Platform", 2001, pp. 1-1134.
Evolution Robotics, Inc.; "ERSP 3.0 - Tutorials", 2001.
Evolution Robotics, Inc.; "ERSP 3.0 - User's Guide", 2001.
Jara; "Outline of ORiN (Open Robot Interface for the Network)", 2001.
Lee, K.; "U.S. Publication No. 2002/0052939", USPTO, Feb. 8, 2001.
U.S. Appl. No. 10/405,883, filed Apr. 1, 2003, Brown et al.
U.S. Appl. No. 10/316,451, filed Dec. 10, 2002, Brown et al.
U.S. Appl. No. 10/761,537, filed Jan. 21, 2004, Brown et al.
U.S. Appl. No. 10/844,025, filed May 12, 2004, Brown et al.
U.S. Appl. No. 11/067,327, filed Feb. 25, 2005, Brown et al.
U.S. Appl. No. 11/084,673, filed Mar. 18, 2005, Brown et al.
U.S. Appl. No. 11/416,660, filed May 3, 2006, Brown et al.
U.S. Appl. No. 11/375,502, filed Mar. 13, 2006, Brown et al.
U.S. Appl. No. 11/370,082, filed Mar. 6, 2006, Brown et al.
U.S. Appl. No. 11/418,075, filed May 4, 2006, Brown et al.
U.S. Appl. No. 11/454,053, filed Jun. 17, 2006, Brown et al.
U.S. Appl. No. 11/505,056, filed Aug. 15, 2004, Brown et al.
U.S. Appl. No. 11/583,233, filed Oct. 19, 2006, Brown et al.
U.S. Appl. No. 11/728,801, filed Mar. 22, 2007, Brown et al.
Pacific Scientific; "Advanced Motion Language", Date Unknown, pp. C-2 thru C-11.
Moore; "Advanced Process Automation and Control System (APACS Product Literature)", Date Unknown, pp. 1-13.
Katila, P.; "Applying Total Productive Maintenance - TPM Principles in the Flexible Manufacturing Systems", Lulea Tekniska Universitet, Date Unknown, pp. 1-41.
Silma; "CimStation Product Literature", Date Unknown, pp. 1-12.
Fanuc Robotics North America; "Manufacturing solutions for value-minded companies (Product Brochure)", Date Unknown, pp. 1-5.

Highland Technology, Inc.; "Perfect Parts Product Literature", Date Unknown, pp. 1-4.
Mitutoyo; "Quick Vision Product Literature", Date Unknown, pp. 1-8.
Fanuc Robotics North America; "Robotic Palletizing Provides Flexibility at High Speeds", Date Unknown, pp. 1-2.
Fanuc Robotics North America; "The Growing Demand for Advanced Robotic Packaging Systems", Date Unknown, pp. 1-2.
Mack, B., Bayoumi, M.; "Design and Integration of New Software for the Robot Controller Test Station", IEEE, 1988, pp. 866-873.
Pritchard, K.; "Applying Simulation to the Control Industry", Cahners Publishing Company, May 1, 1989, pp. 1-3 (reprinted from Control Engineering, May 1989).
Vaataja, H., Hakala, H., Mattila, P., Suoranta, R.; "3-D Simulation of Ultrasonic Sensor System in Mobile Robots", IEEE, 1992, pp. 333-336.
USDATA; "FactoryLink IV for Microsoft Windows and NT", 1992, pp. 1-4.
National Instruments; "IEEE 488 and VXIbus Control, Data Acquisition, and Analysis (Catalog)", 1993, pp. Main Table of Contents, Introduction pp. ii-xi, Section 1 Instrumentation Software Products.
Software Horizons, Inc.; "Operator Interface Software for Supervisory Control, Monitoring and Reporting for Windows Operating System (Product Literature)", 1993, pp. 1-12.
Pro-Log Corporation; "Pro-Log Motion Control for Allen-Bradley PLCs (Product Literature)", 1993, pp. 1-5.
Tele-Denken Resources, Inc.; "VIEWpoint (Product Data Sheet)", 1993, pp. 1-11.
Pritchard, K.; "PC-based Simulation in Control System Design", Cahners Publishing Company, Feb. 1, 1993, pp. 1-2 (reprinted from Control Engineering, Feb. 1993).
Laduzinsky, A.; "An Open Look for PLC Programs", Cahners Publishing Company,. May 1, 1993, p. 1 (reprint from Control Engineering - May 1993).
Christensen, J.; "Programmable controller users and makers to go global with IEC 1131-3", Instrument and Control Systems, Oct. 1, 1993, pp. 1-4 (reprint from Instrument and Control Systems - Oct. 1993).
National Instruments; "LabWindows/CVI Product Literature", 1994, pp. 1-8.
Honeywell Inc.; "SDS Physical Layer Specification", 1994, pp. 1-34.
Steeplechase Software, Inc.; "Visual Logic Controller (Product Literature)", 1994, pp. 1-3.
Tele-Denken Resources, Inc.; "The History of Programmable Controllers", Apr. 1, 1994, pp. 1-26.
Wonderware; "InTouch 5 Lite (Product Data Sheet)", Apr. 14, 1994, pp. 1-4.
Wonderware; "InTouch 5 (Product Data Sheet)", Apr. 19, 1994, pp. 1-4.
Wonderware; "InTouch 5 PDK/NT (Product Data Sheet)", Apr. 19, 1994, pp. 1-4.
Control; "Simulation Software Helps Troubleshoot PLC Code", Jun. 1, 1994, p. 1 (reprinted from Control, Jun. 1994).
Tele-Denken Resources, Inc.; "SoftPLC (Product Data Sheet)", Jun. 1, 1994, pp. 1-5.
Tele-Denken Resources, Inc.; "TopDoc (Product Data Sheet)", Oct. 1, 1994, pp. 1-7.
National Instruments; "LabVIEW Graphical Programming for Instrumentation", 1995, pp. 1-16.
Wizdom Controls, Inc.; "Paradym-31 Software Brochure", 1995, pp. 1-4.
Fanuc Robotics North America; "SpotTool Application Software", 1995, pp. 1-2.
Iconics, Inc.; "Configuring Input/Output (I/O) Devices (GENESIS Product Guide)", Feb. 15, 1995, pp. 1-31.
Quinn, T., George, G.; "Windows 95 Marks a New Era in PC-Based Automation", Cahners Publishing Company, Mar. 1, 1995, pp. 19-20, 22 (Control Engineering, Mar. 1995).
Automation and Control; "Plc Programming Standard Expands", Apr. 1, 1995, pp. 34 (Reprinted from Automation and Control, Apr. 1995).
Cahners Publishing Company; "PC Control Software Combines Ladder Logic, HMI and I/O", May 1, 1995, pp. 1-3 (reprint from Control Engineering - May 1995).
OASYS Group, Inc.; "OASYS Open Architecture System", Jul. 11, 1995, pp. 1-23.
Cahners Publishing Company; "PC Software Adds 'Joy-of-Use' to Power and Flexibility", Sep. 1, 1995, pp. 2-3 (reprinted from Control Engineering, Sep. 1995).
Wonderware; "InTouch 5.6 (Product Data Sheet)", Sep. 15, 1995, pp. 1-4.
Arc Advisory Group; "PC-Based Control Strategies", Oct. 1, 1995.
Wonderware; "InTrack Manufacturing Execution System (Product Data Sheet)", Nov. 15, 1995, pp. 1-5.
Kagami, S., Tamiya, Y., Inaba, M., Inoue, H.; "Design of Real-Time Large Scale Robot Software Platform and its Implementation in the Remote-Brained Robot Project", IEEE, 1996, pp. 1394-1399.
Factorysoft, Inc.; "FactorySoft Report Product Literature", 1996, pp. 1-2.
Galil Motion Control; "Motion Control Product Catalog", 1996, pp. 1-10, 82-91, 106-125.
GE Fanuc Automation; "PowerMotion Servo and Machine Control (Product Brochure)", 1996, pp. 1-8.
Compumotor Division, Parker Hannifin; "Step Motor and Servo Motor Systems and Controls", 1996, pp. 1, 28-29.
Sperber, B.; "Try These Two Little Disks for a Bit Step in Streamlined, Object-Oriented Scada", Control, Apr. 1, 1996, pp. 1-2 (reprinted from CONTROL - Apr. 1996).
GE Fanuc Automation; "GE Fanuc Automation Product Guide", May 1, 1996, pp. 1-8.
National Instruments; "Lookout Product Literature", May 15, 1996, pp. 1-12.
Fusaro, D.; "A Standard for Programming PLCs Emerges - Now What?", Control, Jun. 1, 1996, pp. 1-4 (reprint from CONTROL - Jun. 1993).
GE Fanuc Automation; "CIMPLICITY Product Brochure", Jun. 1, 1996, pp. 1-4.
Siemens Energy and Automation, Inc.; "Siemens Automation Technology Newsletter (Q2/96)", Jul. 1, 1996, pp. 1-24.
Steeplechase Software, Inc.; "Flow Charts Give Focus to Manufacturing", Oct. 1, 1996, pp. 1-2 (Reprinted from Managing Automation, Oct. 1996).
Wonderware; "The Factory Suite Product Literature", 1997, pp. 1-34.
Cahners Publishing Company; "Software Allows Combined Relay Ladder Logic and Flowchart Programming", Feb. 1, 1997, p. 1 (Reprint from Control Engineering, Feb. 1997).
Nematron Corporation; "Nematron OpenControl Product Literature", Mar. 15, 1997, pp. 1-7.
Compumotor Division, Parker Hannifin; "Motion Toolbox User Guide (A Library of LabVIEW Virtual Instruments for Motion Control)", Jun. 1, 1997, pp. i-v, 7-10, 85-93.
Yamamoto, K., Sawabe, T., Ishii, H., Ema, S., Takahashi, T.; "U.S. Publication No. 2002/0181937", USPTO, Nov. 28, 1997.
Iconics, Inc.; "GENESIS32 Version 5.2 Product Workshop", 1998, pp. 1-248.
Pirjanian, P.; "Behavior Coordination Mechanisms - State-of-the-art", USC Robotics Research Laboratory, Oct. 7, 1999, pp. 1-49.
Arc Advisory Group; "HMI Software Strategies", Apr. 1, 2000, pp. 1-16.
Arc Advisory Group; "E=Security Strategies for Enterprises", May 1, 2000, pp. 1-20.
Arc Advisory Group; "Open Control Strategies", May 1, 2000, pp. 1-20.
Deltheil, C., Didier, L., Hospital, E., Brutzman, D.; "Simulating an Optical Guidance System for the Recovery of an Unmanned Underwater Vehicle", IEEE Journal of Oceanic Engineering, Oct. 1, 2000, pp. 568-574.
Tajima, S., Rekimoto, J., Ayatsuka, Y., Matsushita, N., Hasegawa, T., Karasawa, H., Sciammarella, E.; "U.S. Publication No. 2003/0109959", USPTO, Oct. 20, 2000.
Roy-G-Biv Corporation; "Pleadings: Plaintiff Roy-G-Biv Corporation'S Response to Ge Fanuc Automation Corporation's Motion to Dismiss", Dec. 13, 2007, pp. 1-54.

GE Fanuc; "Pleadings: GE Fanuc Automation Corporation's Reply in Support of Its Motion to Dismiss for Lack of Personal Jurisdiction", Dec. 28, 2007, pp. 1-25.

Roy-G-Biv Corporation; "Pleadings: Joint Conference Report", Jan. 4, 2008, pp. 1-6.

Roy-G-Biv Corporation; "Pleadings: Roy-G-Biv Corporation's First Set of Interrogatories (Nos. 1-16) for Each Defendant", Jan. 18, 2008, pp. 1-16.

Roy-G-Biv Corporation; "Pleadings: Roy-G-Biv Corporation's First Set of Requests to Defendants for Document, Electronically Stored Information, and Things", Jan. 18, 2008, pp. 1-19.

GE Fanuc; "Pleadings: Defendants Fanuc Ltd.'s, Fanuc Robotics America, Inc.'s, GE Fanuc Automation Americas, Inc.'s, and GE Fanuc Intelligent Platforms, Inc.'S First Set of Interrogatories to Plaintiff Roy-G-Biv Corporation", Jan. 25, 2008, pp. 1-10.

GE Fanuc; "Pleadings: Defendants Fanuc Ltd.'s, Fanuc Robotics America, Inc.'S, GE Fanuc Automation Americas, Inc.'s, and GE Fanuc Intelligent Platforms, Inc.'s First Set of Requests for Production to Plaintiff Roy-G-Biv Corporation", Jan. 31, 2008, pp. 1-25.

GE Fanuc; "Pleadings: Defendant's Initial Disclosures Pursuant to Federal Rule of Civil Procedure 26(a)(1)", Feb. 1, 2008, pp. 1-6.

Roy-G-Biv Corporation; "Pleadings: Plaintiff Roy-G-Biv Corporation's Initial Disclosures", Feb. 1, 2008, pp. 1-5.

GE Fanuc; "Windows '95 and Windows NT 32-Bit Drivers and Libraries for Open CNC Systems", Nov. 1, 1997, pp. 8-828.

GE Fanuc; "Open Systems (Type II High Speed Serial Bus Setup for 32-Bit Windows 95 and Windows NT Applications) User's Manual", Oct. 1, 1998, pp. 1-1 to B-5.

GE FANUC; "CIMPLICITY HMI for CNC - CNC Machining Interface Plus Operation Manual", Dec. 1, 1999, pp. 1-1 to B-2.

GE FANUC; "CIMPLICITY Integrator's Toolkit - Application Developer's Guide", Dec. 1, 2000, pp. 1-1 to 48-12.

Roy-G-Biv Corporation; "Pleadings: Plaintiff Roy-G-Biv Corporation's Complaint for Patent Infringement and Demand for Jury Trial", Sep. 19, 2007, pp. 1-9.

GE FANUC; "Pleadings: Defendants Fanuc Ltd., Fanuc Robotics America, Inc., GE Fanuc Automation Americas, Inc., and GE Fanuc Intelligent Platforms, Inc.'s Answer to Plaintiff's Complaint for Patent Infringement and Counterclaims for Invalidity and Noninfringement", Nov. 15, 2007, pp. 1-12.

GE FANUC; "Pleadings: Motion to Dismiss", Nov. 21, 2007, 9 pages.

Roy-G-Biv Corporation; "Pleadings: Plaintiff Roy-G-Biv Corporation's Reply to Defendants' Counterclaims for Invalidity and Noninfringement", Dec. 10, 2007, pp. 1-5.

GE FANUC; "Pleadings: Defendant GE Fanuc Automation Americas, Inc.'s Notice of Change of Corporate Name", Dec. 14, 2007, pp. 1-3.

GE FANUC; "Windows '95 and Windows NT 32-Bit Drivers and Libraries for Open CNC Systems", Nov. 1, 1997, pp. 8-828.

GE FANUC; "Open Systems (Type II High Speed Serial Bus Setup for 32-Bit Windows 95 and Windows NT Applications) User's Manual", Oct. 1, 1998, pp. 1-1 to B-5.

GE FANUC; "CIMPLICITY HMI for CNC - CNC Machining Interface Plus Operation Manual", Dec. 1, 1999, pp. 1-1 to B-2.

GE FANUC; "CIMPLICITY Integrator's Toolkit - Application Developer's Guide", Dec. 1, 2000, pp. 1-1 to 48-12.

Roy-G-Biv Corporation; "Pleadings: Plaintiff Roy-G-Biv Corporation's Complaint for Patent Infringement and Demand for Jury Trial", Sep. 19, 2007, pp. 1-9.

GE FANUC; "Pleadings: Defendants Fanuc Ltd., Fanuc Robotics America, Inc., GE Fanuc Automation Americas, Inc., and GE Fanuc Intelligent Platforms, Inc.'s Answer to Plaintiff's Complaint for Patent Infringement and Counterclaims for Invalidity and Noninfringement", Nov. 15, 2007, pp. 1-12.

Roy-G-Biv Corporation; "Pleadings: Plaintiff Roy-G-Biv Corporation's Reply to Defendants' Counterclaims for Invalidity and Noninfringement", Dec. 10, 2007, pp. 1-5.

GE FANUC; "Pleadings: Defendant GE Fanuc Automation Americas, Inc.'s Notice of Change of Corporate Name", Dec. 14, 2007, pp. 1-3.

Daniel A. Norton, "Writing Windows Device Drivers", 1992, pp. 1-435, Addison-Wesley Publishing Company, Inc.

Microsoft Corporation, "Win32 Programmer's Reference: vol. I—Windows Management and Graphics Device Interface", 1993, pp. 1-869, Microsoft Press.

Microsoft Corporation, "Windows NT Device Driver Kit: Win32 Subsystem Driver Design Guide", 1993, pp. 1-80, Microsoft Corporation.

Microsoft Corporation, "Windows NT Device Driver Kit: Network Drivers", 1993, pp. 1-12, Microsoft Corporation.

Microsoft Corporation, "Windows NT Device Driver Kit: Win32 Subsystem Driver Reference", 1993, pp. 1-11, Microsoft Corporation.

Microsoft Corporation, "Windows NT Device Driver Kit: Programming Guide", 1993, pp. 1-11, Microsoft Corporation.

Microsoft Corporation, "Windows NT Device Driver Kit: Kernel-Mode Driver Design Guide", 1993, pp. 1-7. Microsoft Corporation.

Microsoft Corporation, "Windows NT Device Driver Kit: Kernel-Mode Driver Reference", 1993, pp. 1-5. Microsoft Corporation.

Martin Marietta, "Next Generation Workstation/Machine Controller (NGC): vol. VI—Sensor/Effector Standardized Application (SESA)", 1992, pp. 1-38.

Martin Marietta, "Next Generation Workstation/Machine Controller (NGC): vol. V—Controls Standardized Application (CSA)", 1992, pp. 1-95.

Martin Marietta, "Next Generation Workstation/Machine Controller (NGC): vol. IV—Workstation Planning Standardized Application (WPSA)", 1992, pp. 1-120.

Martin Marietta, "Next Generation Workstation/Machine Controller (NGC): vol. III—Workstation Management Standardized Application (WMSA)", 1992, pp. 1-85.

Martin Marietta, "Next Generation Workstation/Machine Controller (NGC): vol. II--NGC Data", 1992, pp. 1-309.

Martin Marietta, "Next Generation Workstation/Machine Controller (NGC): vol. I—Specification for an Open System Architecture Standard (SOSAS)", 1992, pp. 1-259.

Steven K. Sorensen, "An Off-line Approach to Task Level State Driven Robot Programming", 1989, pp. 1-229.

SERCOS Interface, Inc., "SERCOS Interface: Digital Interface for Communications Between Controls and Drives for Numerically Controlled Machines", 1991, pp. 1-366.

Charles Petzoid, "Programming Windows: The Microsoft Guide to Writing Applications for Windows 3—Second Edition", 1990, pp. 1-952, Microsoft Press.

Paul Wright Et Al., "MOSAIC: An Open-Architecture Machine Tool for Precision Manufacturing", 1993, pp. 1-10.

Steven Ashley, "A Mosaic for Machine Tools", Mechanical Engineering Cime, 1990, pp. 1-6.

Adrian King, "Inside Windows 95", 1994, pp. 1-505, Microsoft Press.

Bruel & Kjaer, "Bruel & Kjaer Product Brochure: A System to Build Systems", 1980, pp. 1-64.

Bruel & Kjaer, "Major Challenges in Test Systems for the 1990's", 1991, pp. 1-22.

Bruel & Kajar, "Modular Test System: A Second Generation VXI Architecture", 1980, pp. 1-23.

VME Bus Extensions for Instrumentation, "System Specification VXI-1, Draft 1.4", 1991, pp. 1-24.

Bruel & Kjaer, "Short Form Catalog 1991", 1991, pp. 1-68.

Bruel & Kjaer, "Modular Test System Software Presentation", 1980, pp. 1-36.

Ability Systems Corporation, "Development in Motion", 1990, p. 1.

Ability Systems Corporation, "Indexer LPT Version 5", 1989, pp. 1-214.

Cahners Publishing Company, "New Family of 'NT' Process Software Set to Move In", 1993, 2 pages.

Cahners Publishing Company, "Is Windows NT the PC Platform for the Future?", 1993, 3 pages.

Cahners Publishing Company, "From Distributed Control to Integrated Information", 1992, pp. 13-16.

Thomas, R.; "The Languages of Tape", American Machinist, Jan. 6, 1964, DEFS 00011360-00011367, Special Report No. 545.

Aerotech, Inc.; "Aerotech UNIDEX 31 Series Machine Controller Brochure", Date Unknown, Aerotech 613-623.

Mishra, B., Antoniotti, M.; "ED I: NYU Educational Robot", Date Unknown, DEFS 00007791-00007873.

Wright, P., Hong, J., Tan, X., Pavlakos, L, Hansen, F.; "Mosaic: Machine-tool, Open-System, Advanced Intelligent Controller", Date Unknown, DEFS 00030957-00030962.

Wizdom Controls, Inc.; "Paradym-31 User's Guide and Reference", Date Unknown, DEFS 00047946-00048274.

Wizdom Controls, Inc.; "Paradym-31 User's Guide and Reference", Date Unknown, DEFS 00047946-00048274.

Wizdom Controls, Inc.; "Paradym-31 User's Guide and Reference", Date Unknown, DEFS 00047946-00048274.

Precision Microcontrol; "Precision MicroControl Product Guide (with DEFS)", Date Unknown, RGB00076292-RGB00076323.

Wright, P., Hansen, F., Pavlakos, L.; "Tool Wear and Failure Monitoring on an Open-Architecture Machine Tool", New York University, Date Unknown, DEFS 00031419-00031436.

Allen-Bradley Company, Inc.; "Servo Positioning Assembly User Manual", Oct. 1, 1985, DEFS 00034317-00034563.

Allen-Bradley Company, Inc.; "Servo Positioning Assembly User Manual", Oct. 1, 1985, DEFS 00034317-00034563.

Gmfanuc Robotics Corporation; "GMFCOMM Communications Program Reference Manual - Version 2.11", 1986, DEFS 00058429-00058553.

Gmfanuc Robotics Corporation; "KCS-PC KAREL Communications Software Reference Manual - Version 1.0", 1986, DEFS 00058611-00058786.

Gmfanuc Robotics Corporation; "KAREL OLPC Off-line Programming Software Operations Guide - Version Olpc-V1.50P", 1987, DEFS 00058098-00058305.

Gmfanuc Robotics Corporation; "KAREL-VAX Communication Software Reference Manual - Version 1.1", 1987, DEFS 00057536-00057757.

Greenfeld, I., Hansen, F., Wright, P.; "Self-Sustaining, Open-System Machine Tools", NAMR/SME, 1989, DEFS 00030204-00030210, 1989 Transactions of NAMR/SME.

Greenfeld, I., Hansen, F., Fehlinger, J., Pavlakos, L.; "Robotics Research Technical Report", New York University, Jun. 15, 1989, DEFS00040323-00040398.

Step Tools, Inc.; "Database Use Case Presentation", Apr. 1, 2000, p. 1.

Can in Automation (CIA); "CANopen", Apr. 3, 2000, pp. 1-125, document created on Apr. 3, 2000.

Manufacturing Science and Technology Center (MSTC); "MIMOSA CRIS V2.1 Terminology", Apr. 7, 2000, pp. 1-3, document created Apr. 7, 2000.

Individual; "Containment Early Binding - Draft 1.2", Apr. 12, 2000, pp. 1-17.

ISO/IEC; "Part 203: Application Protocol: Configuration controlled 3D designs of mechanical Parts and assemblies, Amendment 1", May 4, 2000, all pages.

Machinery Information Management Open Systems Alliance (MIMOSA); "Common Relational Information Schema, CRIS Version 2.1", May 8, 2000, all pages.

Individual; "Containment Early Binding - Draft 1.6", May 24, 2000, pp. 1-23.

Can in Automation (CIA); "CANopen: Electronic Data Sheet Specification for CANopen", May 31, 2000, pp. 1-24, CiA Draft Standard Proposal 306, Version 1.0.

Can in Automation (CIA); "CANopen: Layer Setting Services and Protocol", May 31, 2000, pp. 1-17, CiA Draft Standard Proposal 305, Version 1.0.

Yee, K.; "Step @ Boeing", Jun. 1, 2000, The Boeing Company, pp. 1-19.

Mitsuishi, M.; Mutou, K.; Anmi, S.; Inazuru, I.; Kanemoto, M.; Shirakata, N.; Takagi, T.; Naitou, M.; Matsuda, S.; Yamaguchi, M.; Miyajima, H.; "User Interface for an Open-Architecture Controller", Jul. 1, 2000, 2000 Japan USA Symposium on Flexible Automation, pp. 1-4.

ISO - International Standards Organization; "ISO 10303-42: Industrial automation systems and integration - Product data representation and exchange - Part 42: Integrated generic resource: Geometric and topological representation", Sep. 1, 2000, pp. 1-346.

Manufacturing Science and Technology Center (MSTC); "MSTC/JOP-1202: Specifications of the OpenMES Framework, Version 1.0 (Draft alpha 2)", Sep. 1, 2000, pp. 1-72.

Spada, S.; "Roy-G-Biv Tames the Motion Control Tiger", Sep. 6, 2000, ARC Advisory Group, pp. 1-4.

Red, E.; "Introduction to Robotics", Sep. 8, 2000, BYU Mechanical Engineering Department, pp. 1-30, document created on Sep. 8, 2000.

ISO - International Standards Organization; "ISO 3592: Industrial automation systems - Numerical control of machines - NC processor output - File structure and language format, Second Edition", Sep. 15, 2000, all pages.

ISO - International Standards Organization; "CEB Binding - Draft 3.0", Sep. 29, 2000, pp. 1-45.

Price, D.; "Step Modularization Overview Presentation", Oct. 1, 2000, IBM Corporation, pp. 1-41.

Weyrich, M.; Rommel, B.; Haasis, S.; Mueller, P.; "First Prototype of a NC Controller based on Step-NC", Oct. 4, 2000, pp. 1-11, document creation date Oct. 4, 2000.

Individual; "ISO 4343: Industrial Automation Systems - Numerical control of machines - NC processor output - Post processor commands: Second Edition", Oct. 15, 2000, all pages.

ISO - International Standards Organization; "ISO/PDTS 10303-28: XML representation of Express schemas and data", Oct. 16, 2000, all pages.

ISO - International Standards Organization; "Proposal of New Process Data Model based on AP213", Oct. 16, 2000, all pages.

ISO - International Standards Organization; "ISO 10303-41: Industrial automation systems and integration - Product data representation and exchange - Part 41: Integrated generic resource: Fundamentals of product description and support: Second Edition", Nov. 1, 2000, all pages.

Penton Media, Inc.; "When data transfer goes awry", Dec. 7, 2000, all pages, Dec. 7, 2000 issue of Machine Design (www.machinedesign.com).

Step Tools, Inc.; "Introduction to STEP-NC: Advanced Control Flow for NC Workplans", 2001, pp. 1-14.

Step Tools, Inc.; "Introduction to STEP-NC: AP-238 and the Step Integrated Resources", 2001, pp. 1-19.

Step Tools, Inc.; "Introduction to STEP-NC: Cutting Tools for Milling", 2001, pp. 1-12.

Step Tools, Inc.; "Introduction to STEP-NC: Explicit Toolpaths", 2001, pp. 1-11.

Step Tools, Inc.; "Introduction to STEP-NC: In-Process Features", 2001, pp. 1-12.

Step Tools, Inc.; "Introduction to STEP-NC: Milling Operations", 2001, pp. 1-18.

Step Tools, Inc.; "Introduction to STEP-NC: Project and Setups", 2001, pp. 1-12.

Step Tools, Inc.; "Introduction to STEP-NC: Stock", 2001, pp. 1-3.

Step Tools, Inc.; "Introduction to STEP-NC: The STEP-NC Backbone: Executables", 2001, pp. 1-20.

Step Tools, Inc.; "Introduction to STEP-NC: The Step-NC Backbone: Workpiece and Features", 2001, pp. 1-37.

Step Tools, Inc.; "Introduction to STEP-NC: What is STEP-NC and What Does it Cover?", 2001, pp. 1-31.

Terakado, Y.; "Standardization Group - STEP Group", 2001, ECOM Journal, pp. 1-5, Published in ECOM Journal, No. 3 (believed published in 2001 or later as the article describes events occurring in 2001).

Loffredo, D.; "STEP-NC: E-Manufacturing Using Step Presentation", 2001, STEP Tools, Inc., pp. 1-22.

Shah, H.; "Packaging Industry Encourages Broad Adoption of Motion Control Technology", Jan. 4, 2001, ARC Advisory Group, pp. 1-4.

Roy-G-Biv Corporation; "Techno-isel CAD/CAM & CNC Brochure", Feb. 11, 2001, pp. 8-9.

OSACA Association; "OSACA Handbook, Version 2.0", Feb. 16, 2001, pp. 1-440 (all pages).

Radack, G.; "WG3 Presentation to SC4 Opening Plenary - T24 - STEP-Manufacturing Presentation", Feb. 19, 2001, ISO - International Standards Organization, pp. 1-2.

Popular Mechanics; "United Internet Technologies Transforms Toy Industry With Intelligent Creative Interactive Technology", Mar. 1, 2001.

Slansky, D.; Spada, S.; "OMAC Embraces the Internet to Enable Machine Tool Collaboration", Mar. 7, 2001, ARC Advisory Group, pp. 1-4.

Acroloop Motion Control Systems, Inc.; "Acroloop - Perfection in Motion Catalog", Mar. 29, 2001, pp. 3-54, document created on Mar. 29, 2001.

AB Journal; "AB Journal New and Noteworthy", Apr. 1, 2001, pp. 1-5.

ISO - International Standards Organization; "ISO 13584-1: Industrial automation systems and integration - Parts library - Part 1: Overview and fundamental principles: Apr. 15, 2001", pp. 1-26.

Can in Automation (CIA); "CANopen Cabling and Connector Pin Assignment", Apr. 20, 2001, pp. 1-22.

Compumotor Division, Parker Hannifin; "CompuCAM Computer Aided Motion", May 6, 2001, pp. 1-27.

Kanehiro, F.; Inaba, M.; Inoue, H.; Hirukawa, H.; Hirai, S.; "Developmental Software Environment that is applicable to Small-size Humanoids and Life-sized Humanoids", May 21, 2001, IEEE, pp. 4084-4089.

Lutz, P.; "OSACA Proposal of an XML Model for OSACA", May 23, 2001, OSACA Association, pp. 1-13.

Can in Automation (CIA); "CANopen Indicator Specification", Jun. 1, 2001, pp. 1-7, Draft Recommendation 303-3.

GE FANUC; "CIMPLICITY HMI for CNC - Operation Manual", Jun. 1, 2001, 260 pages.

Nell, J.; "ISO 10303: Step on a Page - #3", Jun. 7, 2001, p. 1.

Loffler, M.; Dawson, D.; Zergeroglu, E.; Costescu, N.; "Object-Oriented Techniques in Robot Manipulator Control Software Development", Jun. 25, 2001, Proceedings of the American Control Conference, pp. 4520-4525.

ISO - International Standards Organization; "ISO/FDIS 14649-10: Industrial automation systems and integration - Physical device control - Data model for Computerized Numerical Controls - Part 10: General Process Data: Draft", Aug. 29, 2001, pp. 1-172.

SO - International Standards Organization; "ISO/FDIS 14649-11: Industrial automation systems and integration - Process device control - Data model for Computerized Numerical Controllers - Part 11: Process Data for Milling: Draft", Aug. 29, 2001, pp. 1-76.

ISO - International Standards Organization; "ISO/FDIS 14649-111: Industrial automation systems and integration - Physical device control - Data model for Computerized Numerical Controllers - Part 111: Tools for Milling:Draft", Aug. 29, 2001, pp. 1-27.

Ryou, 0.; Jerard, R.; "Facile: A Clean Interface for Design and Fabrication of Mechanical Parts", Sep. 1, 2001, University of New Hampshire, Mechanical Engineering Department, pp. 1-85.

Michaloski, J.; "OMAC HMI Data Type Overview using W3C XML and STEP", Sep. 18, 2001, OMAC HMI Working Group, pp. 1-11, document created on Sep. 18, 2001.

National Electronic Manufacturing Initiative, Inc.; "NEMA Members Letter: Industry Input on Data Exchange Convergence", Sep. 21, 2001, pp. 1-6.

Stark, J.; "2PDM e-zine Web Article (www.johnstark.com)", Sep. 24, 2001, pp. 1-10, vol. 4, No. 3.

Loffredo, D.; "STEP-NC Mapping Notes", Sep. 26, 2001, STEP Tools, Inc., pp. 1-21.

Hoske, M.; "Connect the plant floor to supply chain", Oct. 1, 2001, Cahners Publishing Company, pp. 1-7, Oct. 2001 issue of Control Engineering.

Hardwick, D.; "STEP-NC Frequently Asked Questions", Oct. 1, 2001, pp. 1-10.

Bengtsson, K.; "Industry Interest - Design, Engineering Simulation", Nov. 1, 2001, EPM Technology, pp. 1-24, NorduGrid Workshop.

Microsoft Corporation; "Categorizing by Component Capabilities", Nov. 1, 2001, Platform SDK: COM.

Michaloski, J.; "STEP-NC Architecture Overview", Nov. 28, 2001, NIST, pp. 1-2, document creation date: Nov. 28, 2001.

Roy-G-Biv Corporation; "Roy-G-BIV Teams With OKUMA to Help Lean Manufacturing Vision Become Reality", Dec. 1, 2001, pp. 1-2.

Roy-G-Biv Corporation; "XMC Powers Robotic Welding Application for Future NASA Space Shuttles", Dec. 1, 2001, pp. 1-2.

Delta Tau Data Systems, Inc.; "PMAC Quick Reference Guide", Dec. 10, 2001, pp. 1-79.

Downie, B.; Hardwick, D.; "3D Data for Pipe Bending and Cutting Machines", 2002, STEP Tools, Inc., pp. 1-12.

Jerard, R.; Ryou, 0.; "E-Commerce for the Metal Removal Industry", Jan. 7, 2002, 2002 NSF Design, Service and MFG Grantees and Research Conference, pp. 1-28.

ISO - International Standards Organization; "ISO/FDIS 14649-10: Industrial automation systems and integration - Physical device control - Data model for Computerized Numerical Controllers - Part 10: General Process Data: Draft 2002", Feb. 6, 2002, pp. 1-179.

ISO - International Standards Organization; "ISO/FDIS 14649-11: Industrial automation systems and integration - Physical device control - Data model for Computerized Numerical Controllers - Part 11: Process Data for Milling: Draft 2002", Feb. 6, 2002, pp. 1-76.

ISO - International Standards Organization; "ISO/FDIS 14649-111: Industrial automation systems and integration - Physical device control - Data model for Computerized Numerical Controllers - Part 111: Tools for Milling: Draft 2002", Feb. 6, 2002, pp. 1-27.

Brown, D.; "OMAC-HMI, OSACA, JOP Standard CNC Data Type Analysis", Feb. 9, 2002, ROY-G-BIV Corporation.

ISO - International Standards Organization; "ISO/WD 10303-238: STEP-NC AIM v2.8 - Draft", Feb. 24, 2002, pp. 1-810.

Krar, S.; Gill, A.; "Open Architecture CNC (Advanced Manufacturing Magazine)", Mar. 1, 2002, CLB Media Inc., pp. 23-27. vol. 4, No. 2.

Cover, R.; "The XML Cover Pages STEP/EXPRESS and XML", Mar. 29, 2002, pp. 1-11.

STEP Tools, Inc.; "ST-XML Manual", Apr. 1, 2002, pp. 1-60.

Individual; "AAM for AP2xx (Process Plans for Machined Products) Presentation", Apr. 11, 2002, pp. 1-11, document creation date: Apr. 11, 2002.

Callen, J.; "A View from the CAM Side - Moving into 3D", May 1, 2002, Desktop Engineering Magazine, pp. 1-3, Desktop Engineering Magazine Web Article (www.deskeng.com).

OMAC Users Group; "OMAC STEP-NC: The Value Proposition for STEP-NC", May 1, 2002, pp. 1-23.

GE FANUC; "TCP/IP Ethernet Communications - Station Manager Manual", May 1, 2002, Chapters 1, 3, 4 and 5, pp. 1-9, 14-56.

I++ Working Group; "I++ DME Interface, Version 1.09", May 17, 2002, pp. 1-76, document created on May 17, 2002.

Wood, R.; "Integrated Steel Processing Environment (ISPE) Project Presentation", Jun. 10, 2002, Northrop Grumman Corporation, pp. 1-3.

Vorburger, T.; "Report on AP219 - Dimensional Inspection Information Exchange Project Presentation", Jun. 10, 2002, NIST, pp. 1-16.

Radack, G.; "WG3 Presentation to SC4 Opening Plenary - TC4 - STEP-Manufacturing", Jun. 10, 2002, ISO - International Standards Organization, pp. 1-4, document creation date: Jun. 10, 2002.

Individual; "AP2XX_ARM_060602 Presentation", Jun. 11, 2002, pp. 1-18, document creation date: Jun. 11, 2002.

Individual; "TC 184, SC4, WG3, T24 (Manufacturing) Session on AP219 Meeting Notes", Jun. 12, 2002, pp. 1-2.

Danner, B.; Frechette, S.; Vorburger, T.; "AP219 Dimensional Inspection - Informational requirements document Presentation", Jun. 14, 2002, Seneca-IT.com, pp. 1-24.

Danner, B.; Frechette, S.; Vorburger, T.; "A Step-Based Information Model for Dimensional Inspection - Draft", Jun. 20, 2002, ISO - International Standards Organization, pp. 1-95.

Kepware Technologies; "KEPServerEX OPC Server Software", Jul. 12, 2002, pp. 1-202.

Siemens AG Automation and Drives; "SCADA: The Strategic Centre - IT and Business Integration Technical Article", Dec. 10, 2002.

Rockwell Automation Technologies, Inc.; "FactoryTalk - Enabled Solutions", 2003.

Fanuc Ltd.; "FANUC Series 30i/31i/32i:300i/310i/320i:300is/310is/320is-MODEL A Brochure", 2003, pp. 1-28.

Fanuc Robotics America, Inc; "HandlingWorks Product Brochure", 2003, pp. 1-2.

Baron, M.; "Process Visualization - Up to Date - Technical Article", 2003, Siemens AG Automation and Drives.

Fanuc Robotics North America, Inc.; "R-J3/R-J3iB Integrated PMC", 2003, pp. 1-2.

Siemens AG Automation and Drives; "Simatic WinCC Version 6 System Description Product Brochure", 2003.
Roy-G-Biv Corporation; "XMC Helps Systems Integrator Improve Customer's Efficiency With CNC Machine-Tool Retrofit", 2003, pp. 1-2.
Individual; "AP240_ARM_DIS_012003 Presentation", Feb. 25, 2003, pp. 1-20, document creation date: Feb. 25, 2003.
Kepware Technologies; "User Configurable Driver Users Manual", 2004.
Rockwell Automation Technologies, Inc.; "Integrated Architecture Product Literature", Apr. 1, 2004.
GE Fanuc; "Proficy Machine Edition - a suite of Proficy products for Control, Motion, and Operator Interface applications", Jul. 1, 2004, pp. 1-120.
Ard, J.; "ReExamination Declaration of Joel B. Ard", Apr. 23, 2009, Black, Lowe and Graham, all pages.
Roy-G-Biv Corp, Fanuc Ltd, Fanuc Robotics, and GE Fanuc; "Pleadings: Notice of Compliance With P.R. 4-5(d)", Jan. 9, 2009, pp. 1-3.
Roy-G-Biv Corp, Fanuc Ltd, Fanuc Robotics, and GE Fanuc; "Pleadings: Supplemental Joint Claim Construction and Prehearing Statement - Exhibit A", Jan. 9, 2009, pp. 1-2.
Roy-G-Biv Corp, Fanuc Ltd, Fanuc Robotics, and GE Fanuc; "Pleadings: Supplemental Joint Claim Construction and Prehearing Statement - Exhibit B", Jan. 9, 2009, pp. 1-9.
Roy-G-Biv Corp, Fanuc Ltd, Fanuc Robotics, and GE Fanuc; "Pleadings: Supplemental Joint Claim Construction and Prehearing Statement - Exhibit C", Jan. 9, 2009, pp. 1-110.
Roy-G-Biv Corp, Fanuc Ltd, Fanuc Robotics, and GE Fanuc; "Pleadings: Supplemental Joint Claim Construction and Prehearing Statement - Exhibit D", Jan. 9, 2009, pp. 1-80.
Roy-G-Biv Corp, Fanuc Ltd, Fanuc Robotics, and GE Fanuc; "Pleadings: Supplemental Joint Claim Construction and Prehearing Statement", Jan. 9, 2009, pp. 1-4.
Fanuc Ltd, Fanuc Robotics, and GE Fanuc; "Pleadings: Defendants and Counterclaim Plaintiffs Fourth Set of Requests for Production to Plaintiff and Counterclaim Defendant (Nos. 144 to 183)", Feb. 19, 2009, pp. 1-11.
Fanuc Ltd, Fanuc Robotics, and GE Fanuc; "Pleadings: Objections and Responses of Defendants to Plaintiff's Second Set of Interrogatories (Nos. 17-18) - Redacted", Mar. 16, 2009, All pages.
Fanuc Ltd, Fanuc Robotics, and GE Fanuc; "Pleadings: Defendant's Markman Claim Construction Hearing Tutorial", Apr. 15, 2009, all pages.
Roy-G-Corporation; "Pleadings: Plaintiff Markman Claim Construction Tutorial", Apr. 15, 2009, all pages.
Folsom, D.; "Order: (GRANTING) Motion for Continuance", Aug. 25, 2009, US Dist Court EDTX, Marshal Div, p. 1.
Folsom, D.; "Order: Claim Construction ('897, '058, '236 and '543 Patents)", Aug. 25, 2009, US Dist Court EDTX, Marshal Div, pp. 1-64.
Fanuc Ltd, Fanuc Robotics, and GE Fanuc; "Pleadings: Defendant's Markman Presentation for Claim Construction Hearing", Apr. 16, 2009, all pages.
Roy-G-Biv Corporation; "Pleadings: Plaintiff Markman Claim Construction Argument", Apr. 16, 2009, all pages.
Everingham IV, C.; "Order: (Granted in Part) Plaintiff Motion for Proctective Order re Experts", Jun. 4, 2009, US Dist Court EDTX, Marshal Div, All pages.
Everingham IV, C.; "Order: (Granted) Plaintiff Motion to Complel re Fanuc Witnesses", Jun. 4, 2009, US Dist Court EDTX, Marshal Div, All pages.
Fanuc Ltd, Fanuc Robotics, and GE Fanuc; "Pleadings: Defendant's Request for Leave to File a Motion for Summary Adjudication of Non-Infringement", Jun. 15, 2009, All pages.
Fanuc Ltd, Fanuc Robotics, and GE Fanuc; "Pleadings: Defendants Motion for Reconsideration of Order Granting Plantiff's (Amended) Motion for Protective Order (D.E. 170)", Jun. 15, 2009, All pages.
Fanuc Ltd, Fanuc Robotics, and GE Fanuc; "Pleadings: Defendants Third Set of Interrogatories to Plaintiff (Nos. 19-28)", Jun. 17, 2009, All pages.
Roy-G-Biv Corporation; "Pleadings: Plaintiffs Fourth Set of Interrogatories (Nos. 25-27) for Each Defendant", Jun. 19, 2009, All pages.
Fanuc Ltd, Fanuc Robotics, and GE Fanuc; "Pleadings: Objections and Responses of Defendants to Plaintiffs Fourth Set of Interrogatories (Nos. 25-27)", Jul. 2, 2009, All pages.
Individual; "Order: (Denying) Defendants Motion for Reconsideration re Protective Order", Jul. 9, 2009, All pages.
Galil Motion Control; "Galil Dynamic Data Exchange Server for DMC-1000", Date Unknown, pp. 1-2.
Galil Motion Control; "Galil OPINT600 Product Features", Date Unknown, pp. 1-3.
Tal, J.; "Motion Control by Microprocessors", 1984, Galil Motion Control.
Tal, J.; "Motion Control Applications", 1989, Galil Motion.
Galil Motion Control; "Galil G-Code Translator News Release", Apr. 14, 1989, pp. 1-2.
Galil Motion Control; "Galil OPINT600 Product Literature", Jun. 1, 1989, pp. 1-2.
Galil Motion Control; "Galil ServoTRENDS vol. V. No. 3", Jul. 1, 1989, pp. 1-3.
Galil Motion Control; "Galil OPINT600 Press Release", Jul. 10, 1989, pp. 1-2.
Takase, K.; "Project of a robot performing in an extreme situation", Oct. 15, 1991, vol. 9, No. 5, pp. 79-82, p. 59.
Dictionary.com LLC; "www.dictionary.com definition of 'persistent'", 1993.
Galil Motion Control; "Galil ServoTRENDS vol. IX. No. 2", Sep. 1, 1993, pp. 1-4.
Cahners Publishing Company; "Control Engineering Software", Oct. 1, 1993, p. 184 of Oct. 1993 issue of Control Engineering.
Tuggle, E.; "Introduction to Device Driver Design", Oct. 5, 1993, Proceedings of the Fifth Annual Embedded Systems Conference, pp. 455-468, vol. 2.
Tal, J.; "Step-By-Step Design of Motion Control Systems", 1994, Galil Motion Control.
Galil Motion Control; "Galil ServoTRENDS vol. X. No. 2", Jul. 1, 1994, pp. 1-4.
Wonderware; "Wonderware InTouch DDE I/O Server Listing", Nov. 1, 1996, pp. 1-14.
Numerical Control Society; "Who's Who in Numerical Control - 1972", 1972, all pages.
Numerical Control Society; "Who's Who In Numerical Control - 1973", 1973, all pages.
Greenfeld, I.; Wright, P.; "A Generic User-Level Specification for Open-System Machine Controllers", Date Unknown, New York University, pp. 1-17.
Penton Media, Inc.; "Technology Trends section of American Machinist", Date Unknown, all pages (publish date unknown, from American Machinist).
ISO - International Standards Organization; "ISO 6983/1: Numerical control of machines - Program format and definition of address words: Part 1: Data format for positioning, line motion and contouring control systems: First Edition", Sep. 15, 1982, pp. 1-16.
ISO- International Standards Organization; "ISO 4342: Numerical control of machines - NC processor input - Basic part program reference language, First Edition", Dec. 15, 1985, all pages.
Petzold, C.; "The GDI Philosophy", 1988, Microsoft Development Library, Jul. 1994 MSDN, Programming Windows 3.1, pdf pp. 1-2.
Electronic Industries Association; "EIA-511 Manufacturing Message Specification - Service Definition and Protocol", Mar. 1, 1989, pp. 1-177.
Electronic Industries Association; "EIA-511 Errata", Apr. 18, 1989, pp. 1-7.
Salkind, L.; "Robotics Research Technical Report - SAGE A Real-Time Operating System for Robotic Supervisory Control", May 1, 1990, New York University, pp. 1-132. (DEFS 0004094-00041085).
ISO/IEC; "ISO/IEC 8824: Information Technology - Open Systems Interconnection - Specification of Abstract Syntax Notation One", Dec. 15, 1990, all pages.
Compumotor Division, Parker Hannifin; "6000 Series Programmer's Guide", 1991, all pages.
Iyengar, S.; Elfes, A.; "Autonomous Mobile Robots: Control, Planning, and Architecture", 1991, IEEE Computer Society Press, all pages.

Iyengar, S.; Elfes, A.; "Autonomous Mobile Robots: Perception, Mapping, and Navigation", 1991, IEEE Computer Society Press, All pages.

Microsoft Development Library; "1.1 Printer Driver Operation", 1992, Jul. 1994 MSDN, Windows NT DDK: Win32 Subsystem Driver Design Guide, pdf pp. 1-6.

Microsoft Development Library; "3.1.1 Using Unitool", 1992, Jul. 1994 MSDN, Windows NT DDK: Win32 Subsystem Driver Design Guide, pdf pp. 1-101.

Microsoft Development Library; "3.4 Specifying Cursor-Movement Commands", 1992, Jul. 1994 MSDN, Windows NT DDK: Win32 Subsystem Driver Design Guide, pdf pp. 1-7.

Microsoft Development Library; "4.1.22 Banding Drivers", 1992, Jul. 1994 MSDN, Windows 3.1 DDK: Device Driver Adaptation Guide, pdf pp. 1-3.

Microsoft Development Library; "Chapter 11 - Graphics-Driver Escapes", 1992, Jul. 1994 MSDN, Windows 3.1 DDK: Device Driver Adaptation Guuide, pdf pp. 1-50.

Microsoft Development Library; "Chapter 2 Supporting DDI Printing and User Interface Functions", 1992, Jul. 1994 MSDN, Windows NT DDK: Win32 Subsystem Driver Design Guide, pdf pp. 1-5.

Microsoft Development Library; "Chapter 4 - Specifying Control Information", 1992, Jul. 1994 MSDN, Windows 3.1 DDK: Minidriver Development Guide, pdf pp. 1-16.

Microsoft Development Library; "Chapter 5 Printer Escapes", 1992, Jul. 1994 MSDN, Windows 3.1 SDK: Programmers Reference, vol. 3: Messages, Structures, Macros, pdf pp. 1-5.

Microsoft Development Library; "Chpater 7 Minidriver", 1992, Jul. 1994 MSDN, International SDKS: Hanguel Windows DDK, pdf pp. 1-8.

Lynch, M.; "Computer Numerical Control for Machining", 1992, McGraw-Hill Inc., All pages (Copyright 1992).

Microsoft Development Library; "Win32 SDK Programmers API Reference, Escape Function", 1992, Jul. 1994 MSDN, Win32 SDK Programmers API Reference, vol. 3, pdf pp. 1-2.

Microsoft Development Library; "Windows 3.1 SDK: Programmers Reference vol. 2: Functions - SpoolFile", 1992, Jul. 1994 MSDN, Windows 3.1 Programmers Reference vol. 2: Functions, pdf p. 1.

Ambrose, C.; "The Development of an Interactive Synthesis Tool for Intelligent Controllers of Modular Reconfigurable Robots", Dec. 1, 1992, pp. 1-304.

Microsoft Development Library; "How to Send Printer Escape Codes from a WinWord Document", Oct. 25, 1993, Jul. 1994 MSDN, Knowledge Base Article, PSS ID No. Q93658, pdf p. 1.

Lin, S.; "Computer Numerical Control - From Programming to Networking", 1994, Delmar Publishers, Inc, all pages.

Microsoft Development Library; "Using Passthrough Escape to Send Data Directly to Printer", Feb. 2, 1994, Jul. 1994 MSDN, Knowledge Base Article, PSS ID No. Q96795, pdf pp. 1-2.

Can in Automation (CIA); "CAN Physical Layer for Industrial Applications", Apr. 20, 1994, pp. 1-4, CiA Draft Standard 102, Version 2.0.

Kramer, T.; Proctor, F.; Michaloski, J.; "The NIST RS274/NGC Interpreter - Version 1", Apr. 28, 1994, NIST, pp. 1-26.

ISO - International Standards Organization; "ISO/CD 10303-204: Application protocol: Mechanical design using boundary representation - Draft", Apr. 29, 1994, pp. 1-214.

Microsoft Development Library; "INF: An Alternative to SpoolFile()", May 6, 1994, Jul. 1994 MSDN, Knowledge Base Article, PSS ID No. Q111010, pdf pp. 1-5.

Microsoft Development Library; "INF: Banding, Printing, and the Number of Bands", May 6, 1994, Jul. 1994 MSDN, Knowledge Base Article, PSS ID No. Q72691.

Microsoft Development Library; "INF: Basics of Banding Printing in Windows", May 6, 1994, Jul. 1994 MSDN, Knowledge Base, PSS ID No. Q75471, pdf pp. 1-2.

ISO/IEC; "ISO/IEC 9506-6: Industrial automation systems - Manufacturing message specification - Part 6: Companion Standard for Process Control", Jun. 1, 1994, pp. 1-267.

ISO/IEC; "ISO/IEC 9545: Information technology - Open Systems Interconnection - Application Layer structure", Aug. 15, 1994, pp. 1-20.

ISO - International Standards Organization; "ISO 10303-1: Industrial automation systems and integration - Product data representation and exchange - Part 1: Overview and fundamental principles: First Edition", Dec. 15, 1994, pp. 1-28.

ISO-International Standards Organization; "ISO 1033-11: Part 11: Description methods: The EXPRESS language reference manual", Dec. 15, 1994, all pages.

Lewis, M.; "Five best bets for the machine-tool industry", Mar. 1, 1997, Penton Media, Inc., p. 79, 80, 92 (Mar. 1997 issue of American Machinist).

Penton Media, Inc.; "CAM software offers simultaneous 5-axis machining", Apr. 1, 1997, p. 32, Apr. 1997 edition of American Machinist.

Penton Media, Inc.; "Software opens up many possibilities", Sep. 1, 1997, p. 36 (Sep. 1997 issue of American Machinist).

Fritz, K.; Grant, K.; Khambholja, K.; Krueger, J.; "Circuit Board Prototyping System, CS400 Senior Design", Oct. 10, 1997, Milwaukee School of Engineering, pp. 1-17.

Scholar's International Publishing Corp.; "Chapter 1 - CNC Programming Fundamentals - From MasterCam Documentation", 1998, all pages.

Petzold, C.; "The Technique of Banding", 1998, Microsoft Development Library, Jul. 1994 MSDN, Programming Windows 3.1, pdf pp. 1-9.

Loffredo, D.; "Efficient Database Implementation of EXPRESS Information Models (Presentation)", Apr. 10, 1998, pp. 1-26.

Loffredo, D.; "Efficient Database Implementation of EXRESS Information Models", May 1, 1998, pp. 1-133.

Can in Automation (CIA); "CAN Specification 2.0, Part A", Jun. 12, 1998, pp. 1-31, document created on Jun. 12, 1998.

Can in Automation (CIA); "CAN Specification 2.0, Part B", Jun. 12, 1998, pp. 1-38, document created on Jun. 12, 1998.

Fredriksson, L; "A Can Kingdom", 1995, KVASER AB, pp. 1-109, Rev 3.01.

Webb, J.; Reis, R.; "Programmable Logic Controllers - Principles and Applications (Third Edition)", 1995, Prentice-Hall, Inc., All pages. (Copyright 1995).

ISO - International Standards Organization; "ISO/CD 10303-214 - Application protocol: Core Data for Automotive Mechanical Design Process - Draft", Aug. 8, 1995, pp. 1-1967.

Kramer, T.; Proctor, F.; "The NIST RS274/NGC Interpreter - Version 2", Oct. 26, 1995, NIST, pp. 1-58.

Selamoglu, H.; "Component Categories", Dec. 1, 1995, Microsoft Development Library, pp. 1-19.

OPC Foundation; "OLE for Process Control Standard - Version 1.0 Draft", Dec. 22, 1995, pp. 1-70.

ESPRIT 5629 Project; "Open System Architecture for Controls within Automation Systems EP 6379 and EP 9115, Osaca I and II Final Report", Apr. 30, 1996, pp. 1-79.

Individual; "SC4 Framework Presentation - Annex A-N326 Presentation", Sep. 30, 1996, pp. 1-8, document creation date: Sep. 30, 1996.

ISO/IEC; "ISO/IEC 8649: Information Technology - Open Systems Interconnection - Service definition for the Association Control Service Element", Oct. 15, 1996, all pages.

Penton Media, Inc.; "Computer Store (American Machinist)", 1997, p. 83 (Jan. 1997 issue of American Machinist).

ISO - International Standards Organization; "ISO 10303-49: Industrial automation systems and integration - Product data representation and exchange - Part 49: Integrated generic resources: Process structure and properties: First Edition", Jun. 15, 2998, pp. 1-64.

ISO - International Standards Organization; "ISO 13584-20: Industrial automation systems and integration - Parts library - Part 20: Logical resource: Logical model of expressions: First Edition", Jul. 1, 1998, pp-1-96.

Can in Automation (CIA); "Can Specification 2.0, Addendum - Implementation Guide for the CAN Protocol", Jul. 7, 1998, pp. 1-3, document created on Jul. 7, 1998.

SO - International Standards Organization; "ISO - DIS 14649-1: Industrial automation systems and integration - Physical device control - Data model for Computerized Numerical Controllers - Part 1: Overview and Fundamental Principles", Sep. 1, 1998, pp. 1-15.

Haynes, T.; "Data Interface for Numerical Controls", Sep. 21, 1998, National Center for Manufacturing Sciences, all pages, NCMS Fall Conference.

Barco Gerber Systems Corporation; "Gerber RS-274X Format User's Guide", Sep. 21, 1998, pp. 1-55.
Price, D.; West, M.; Fowler, J.; "The STEP Data Integration Architecture Activity", Oct. 1, 1998, pp. 1-9, document creation date: Oct. 1, 1998.
ISO 10303 Editing Committee; "ISO 10303 - STEP on a Page", Oct. 23, 1998, p. 1.
ISO 10303 Editing Committee; "ISO 10303: STEP on a p. #2", Oct. 23, 1998, p. 1.
SO/IEC; "ISO/IEC 8824-1: Information technology - Abstract Syntax Notation One (ASN.1): Specification of basic notation: Second Edition", Dec. 15, 1998, all pages.
Birla, S.; Yen, J.; Skeries, F.; Berger, D.; "Controls Software Requirements for Global Commonization", 1999, Cahners Publishing Company, pp. 1-4, Jan. 1999 issue of Control Engineering.
Lee, K.; "Principles of CAD/CAM/CAE Systems", 1999, Addison Wesley Longman, Inc., All pages (Copyright 1999).
Manufacturing Science and Technology Center (MSTC); "The Introduction of Standard Protocol in Japanese Manufacturing Systems and a Proposal of Collaboration", 1999, pp. 1-48.
Brooks, M.; "CAN Bus Simulation Results", Mar. 30, 1999, pp. 1-4.
Brooks, M.; "Rate Monotonic Analysis of an Antenna CAN Bus", May 28, 1999, pp. 1-3.
Mathias, D.; Hellmann, R.; "Boeing Implements HMI", Jun. 1, 1999, Manufacturing Engineering, pp. 1-3.
Hardwick, D.; "STEP Database Tutorial, Chapter One - Making Business Objects Using EXPRESS-X", Jun. 21, 1999, STEP Tools, Inc., pp. 1-20.
ISO/IEC; "CEI/IEC 9506-5: Industrial automation systems - Manufacturing message specification - Part 5: Companion Standard for Programmable Controllers", Jul. 1, 1999, pp. 1-129.
Manufacturing Science and Technology Center (MSTC); "MST/JOP -1012: FL-net Protocol Specifications, Version 1.0", Jul. 1, 1999, pp. 1-65.
Manufacturing Science and Technology Center (MSTC); "MSTC/JOP - 1013: FL-net Device Profile Common Specification, Version 1.0", Jul. 1, 1999, pp. 1-28.
Manufacturing Science and Technology Center (MSTC); "MSTC/JOP-1014: FL-net Implementation Guideline, Version 1.0", Jul. 1, 1999, pp. 1-39.
Manufacturing Science and Technology Center (MSTC); "MSTC/JOP-1015: Basic Specifications of FL-net Product Certification System, Version 1.0", Jul. 1, 1999, pp. 1-11.
Manufacturing Science and Technology Center (MSTC); "MSTC/JOP-1302: CNC Application Programming Interface, PAPI Specification 1.01E", Jul. 26, 1999, pp. i-v, 1-143.
Can in Automation (CIA); "CAN Application Fields", Jul. 28, 1999, pp. 1-5, document created on Jul. 28, 1999.
Can in Automation (CIA); "CAN Data Link Layer", Aug. 9, 1999, pp. 1-44, document created on Aug. 9, 1999.
Can in Automation (CIA); "CAN Implementation", Aug. 9, 1999, pp. 1-33, document created on Aug. 9, 1999.
Can in Automation (CIA); "CAN Physical Layer", Aug. 9, 1999, pp. 1-45, document created on Aug. 9, 1999.
Loffredo, D.; "Fundamentals of STEP Implementation", Sep. 9, 1999, STEP Tools, Inc., pp. 1-12, document creation date: Sep. 9, 1999.
Manufacturing Science and Technology Center (MSTC); "MSTC/JOP-1101: Specifications for Autonomous Decentralized Protocol (R 3.0)", Sep. 30, 1999, pp. 1-79.
ISO - International Standards Organization; "EXPRESS-X Language Reference Manual - Draft", Oct. 15, 1999, all pages.
Manufacturing Science and Technology Center (MSTC); "MSTC/JOP - 1304: Management-data Format for Machine tool", Nov. 30, 1999, pp. i-iii, 1-10.
Hemmett, J.; Fussell, B.; Jerard, R.; "A Robust and Efficient Approach to Feedrate Selection for 3-axis Machining", 2000, ASME IMECE, pp. 1-15, Submission for "Dynamics and Control of Material Removal Process", 2000 ASME IECE.
Proctor, F.; Kamatsu, C.; Glantschnig, F.; "ISO/DIS 14649-1: Industrial automation systems and integration -Physical device control - Data model for computerized numerical controllers - Part 1: Overview and fundamental principles: Draft", 2000, ISO - International Standards Organization, all pages.
SO - International Standards Organization; "ISO/DIS 14649-10: Industrial automation systems and integration - Physical device control - Data model for computerized numerical controllers - Part 10: General process data: Draft", 2000 pp. 1-149.
Westenberg, A.; "Linux CAN-bus HOWTO", 2000, pp. 1-33.
EPM Technology; "STEP-NC A NewData Interface for NC-Programming", 2000, p. 1, The Expressway web-site.
Loffredo, D.; "The STEP ISO Standard Presentation", 2000, STEP Tools, Inc., pp. 1-15.
Jerard, R.; Ryou, O.; "Internet Babsed Fabrication of Discrete Mechanical Parts", Jan. 3, 2000, Proceedings of the 2000 Design and Mfg Research Conference, pp. 1-9.
Can in Automation (CIA); "CANopen Representation of SI Units and Prefixes", Jan. 19, 2000, pp. 1-7.
Individual; "Non-Neutral Comparison of the Part 28 Early Bindings", Mar. 24, 2000, pp. 1-10.
GE Fanuc; "Pleadings: Defendants Proposed Terms and Claim Elements for Construction Pursuant to Patent Rule 4-1", Jul. 25, 2008, pp. 1-16 (pdf pages).
Roy-G-Biv Corporation; "Pleadings: Plaintiff Proposed Terms and Claim Elements for Construction", Jul. 25, 2008, pp. 1-4 (pdf pages).
Roy-G-Biv Corporation; "Pleadings: Plaintiff Identification of Ten Asserted Claims", Aug. 18, 2008, pp. 1-3.
GE Fanuc; "Pleadings: Defendants Claim Constructions and Preliminary Identification of Extrinsic Evidence Pursuant to Patent Rule 4-2", Oct. 3, 2008, pp. 1-13 (pdf pages).
Roy-G-Biv Corporation; "Pleadings: Plaintiff Proposed Claim Constructions and Extrinsic Evidence", Oct. 3, 2008, pp. 1-22 (pdf pages).
GE Fanuc; "Pleadings: Defendant's Preliminary Constructions for Three Terms Identified by Plaintiff", Oct. 16, 2008, pp. 1-2.
GE Fanuc; "Pleadings: Defendant's Second Set of Interrogatories to Plaintiff", Oct. 17, 2008, pp. 1-9 (pdf pages).
GE Fanuc; "Pleadings: Defendants Preliminary Claim Constructions and Preliminary Identification of Extrinsic Evidence Pursuant to Patent Rule 4-2", Oct. 17, 2008, pp. 1-29 (pdf pages).
Roy-G-Biv Corporation; "Pleadings: Plaintiff's Proposed Constructions and Extrinsic Evidence for Terms Identified in Defendant's Letter Dated October 7, 2008", Oct. 17, 2008, pp. 1-9.
Roy-G-Biv Corporation and GE Fanuc; "Pleadings: Joint Claim Construction and Prehearing Statement of Plaintiff and Defendant", Oct. 24, 2008, pp. 1-5 (pdf pages).
Roy-G-Biv Corporation and GE Fanuc; "Pleadings: Joint Claim Construction and Prehearing Statement of Plaintiff and Defendant - Exhibit A", Oct. 24, 2008, pp. 1-2 (pdf pages).
Roy-G-Biv Corporation and GE Fanuc; "Pleadings: Joint Claim Construction and Prehearing Statement of Plaintiff and Defendant - Exhibit B", Oct. 24, 2008, pp. 1-19.
Roy-G-Biv Corporation and GE Fanuc; "Pleadings: Joint Claim Construction and Prehearing Statement of Plaintiff and Defendant - Exhibit C", Oct. 24, 2008, pp. 1-64.
Roy-G-Biv Corporation and GE Fanuc; "Pleadings: Joint Claim Construction and Prehearing Statement of Plaintiff and Defendant - Exhibit C", Oct. 24, 2008, pp. 65-133.
Roy-G-Biv Corporation and GE Fanuc; "Pleadings: Joint Claim Construction and Prehearing Statement of Plaintiff and Defendant - Exhibit D", Oct. 24, 2008, pp. 1-22.
GE Fanuc; "Pleadings: Sixth Supplemental Objections and Responses of Defendants to Plaintiff's First Set of Interrogatories (Nos. 3-5)", Nov. 12, 2008, pp. 1-11 (pdf pages).
Roy-G-Biv Corporation; "Pleadings: Plaintiff's Answers and Objections to Defendant's Second Set of Interrogatories", Nov. 20, 2008, pp. 1-9 (pdf pages).
Roy-G-Biv Corporation; "Pleadings: Plaintiff Opening Markman Brief", Nov. 21, 2008, pp. 1-43 (pdf pages).
Roy-G-Biv Corporation; "Pleadings: Plaintiff Opening Markman Brief - Exhibit 1", Nov. 21, 2008, pp. 1-12 (pdf pages).
Roy-G-Biv Corporation; "Pleadings: Plaintiff Opening Markman Brief - Exhibit 10", Nov. 21, 2008, pp. 1-21 (pdf pages).
Roy-G-Biv Corporation; "Pleadings: Plaintiff Opening Markman Brief - Exhibit 11", Nov. 21, 2008, pp. 1-20 (pdf pages).

Roy-G-Biv Corporation; "Pleadings: Plaintiff Opening Markman Brief - Exhibit 12", Nov. 21, 2008, pp. 1-11 (pdf pages).
Roy-G-Biv Corporation; "Pleadings: Plaintiff Opening Markman Brief - Exhibit 13", Nov. 21, 2008, pp. 1-11 (pdf pages).
Roy-G-Biv Corporation; "Pleadings: Plaintiff Opening Markman Brief - Exhibit 14", Nov. 21, 2008, pp. 1-6 (pdf pages).
Roy-G-Biv Corporation; "Pleadings: Plaintiff Opening Markman Brief - Exhibit 15", Nov. 21, 2008, pp. 1-4 (pdf pages).
Roy-G-Biv Corporation; "Pleadings: Plaintiff Opening Markman Brief - Exhibit 16", Nov. 21, 2008, pp. 1-19 (pdf pages).
Roy-G-Biv Corporation; "Pleadings: Plaintiff Opening Markman Brief - Exhibit 17", Nov. 21, 2008, pp. 1-3 (pdf pages).
Roy-G-Biv Corporation; "Pleadings: Plaintiff Opening Markman Brief - Exhibit 18", Nov. 21, 2008, pp. 1-11 (pdf pages).
Roy-G-Biv Corporation; "Pleadings: Plaintiff Opening Markman Brief - Exhibit 19", Nov. 21, 2008, pp. 1-8 (pdf pages).
Roy-G-Biv Corporation; "Pleadings: Plaintiff Opening Markman Brief - Exhibit 20", Nov. 21, 2008, pp. 1-3 (pdf pages).
Roy-G-Biv Corporation; "Pleadings: Plaintiff Opening Markman Brief - Exhibit 21", Nov. 21, 2008, pp. 1-2 (pdf pages).
Roy-G-Biv Corporation; "Pleadings: Plaintiff Opening Markman Brief - Exhibit 2", Nov. 21, 2008, pp. 1-64 (pdf pages).
Roy-G-Biv Corporation; "Pleadings: Plaintiff Opening Markman Brief - Exhibit 2", Nov. 21, 2008, pp. 65-130 (pdf pages).
Roy-G-Biv Corporation; "Pleadings: Plaintiff Opening Markman Brief - Exhibit 3", Nov. 21, 2008, pp. 1-40 (pdf pages).
Roy-G-Biv Corporation; "Pleadings: Plaintiff Opening Markman Brief - Exhibit 3", Nov. 21, 2008, pp. 41-81 (pdf pages).
Roy-G-Biv Corporation; "Pleadings: Plaintiff Opening Markman Brief - Exhibit 4", Nov. 21, 2008, pp. 1-50 (pdf pages).
Roy-G-Biv Corporation; "Pleadings: Plaintiff Opening Markman Brief - Exhibit 4", Nov. 21, 2008, pp. 51-99 (pdf pages).
Roy-G-Biv Corporation; "Pleadings: Plaintiff Opening Markman Brief - Exhibit 6", Nov. 21, 2008, pp. 1-50.
Roy-G-Biv Corporation; "Pleadings: Plaintiff Opening Markman Brief - Exhibit 6", Nov. 21, 2008, pp. 51-94.
Roy-G-Biv Corporation and GE Fanuc; "Pleadings: Supplemental Joint Claim Construction and Prehearing Statement of Plaintiff and Defendant - Exhibit C", Nov. 21, 2008, pp. 1-64 (pdf pages).
Roy-G-Biv Corporation and GE Fanuc; "Pleadings: Supplemental Joint Claim Construction and Prehearing Statement of Plaintiff and Defendant - Exhibit C", Nov. 21, 2008, pp. 65-131 (pdf pages).
Roy-G-Biv Corporation and GE Fanuc; "Pleadings: Supplemental Joint Claim Construction and Prehearing Statement of Plaintiff and Defendant - Exhibit D", Nov. 21, 2008, pp. 1-50 (pdf pages).
Roy-G-Biv Corporation and GE Fanuc; "Pleadings: Supplemental Joint Claim Construction and Prehearing Statement of Plaintiff and Defendant - Exhibit D", Nov. 21, 2008, pp. 51-98 (pdf pages).
Roy-G-Biv Corporation; "Pleadings: Plaintiff Opening Markman Brief - Exhibit 7", Nov. 21, 2008, p. 1.
Roy-G-Biv Corporation; "Pleadings: Plaintiff Opening Markman Brief - Exhibit 8", Nov. 21, 2008, pp. 1-10 (pdf pages).
Roy-G-Biv Corporation; "Pleadings: Plaintiff Opening Markman Brief - Exhibit 9", Nov. 21, 2008, pp. 1-3 (pdf pages).
Roy-G-Biv Corporation and GE Fanuc; "Pleadings: Supplemental Joint Claim Construction and Prehearing Statement of Plaintiff and Defendant", Nov. 21, 2008, pp. 1-4.
Roy-G-Biv Corporation and GE Fanuc; "Pleadings: Supplemental Joint Claim Construction and Prehearing Statement of Plaintiff and Defendant - Exhibit B", Nov. 21, 2008, pp. 1-13 (pdf pages).
Roy-G-Biv Corporation and GE Fanuc; "Pleadings: Supplemental Joint Claim Construction and Prehearing Statement of Plaintiff and Defendant - Exhibit A", Nov. 21, 2008, pp. 1-2 (pdf pages).
Roy-G-Biv Corporation; "Pleadings: Plaintiff's Answer to Defendant's Second Amended Answer and Counterclaims", Dec. 5, 2008, pp. 1-15 (pdf pages).
Roy-G-Biv Corporation; "Pleadings: Plaintiff's Motion to Dismiss GE Fanuc Intelligent Platforms, Inc. and General Electric Company's Infringement Claims or, Alternatively, Motion to Sever - and Proposed Order", Dec. 5, 2008, pp. 1-11 (pdf pages).
GE Fanuc; "Pleadings: Claim Construction Brief of Defendants", Dec. 6, 2008, pp. 1-46 (pdf pages).
GE Fanuc; "Pleadings: Claim Construction Brief of Defendants - Exhibit A", Dec. 6, 2008, pp. 1-2 (pdf pages).
GE Fanuc; "Pleadings: Claim Construction Brief of Defendants - Exhibit B", Dec. 6, 2008, pp. 1-2 (pdf pages).
GE Fanuc; "Pleadings: Claim Construction Brief of Defendants- Exhibit C", Dec. 6, 2008, pp. 1-2 (pdf pages).
GE Fanuc; "Pleadings: Claim Construction Brief of Defendants- Exhibit D", Dec. 6, 2008, pp. 1-2 (pdf pages).
GE Fanuc; "Pleadings: Declaration of Christina M. Finn", Dec. 6, 2008, pp. 1-6 (pdf pages).
GE Fanuc; "Pleadings: Declaration of Christina M. Finn - Exhibit A", Dec. 6, 2008, pp. 1-13 (pdf pages).
GE Fanuc; "Pleadings: Declaration of Christina M. Finn - Exhibit B", Dec. 6, 2008, pp. 1-2 (pdf pages).
GE Fanuc; "Pleadings: Declaration of Christina M. Finn - Exhibit C", Dec. 6, 2008, pp. 1-2 (pdf pages).
GE Fanuc; "Pleadings: Declaration of Christina M. Finn - Exhibit D", Dec. 6, 2008, pp. 1-2 (pdf pages).
GE Fanuc; "Pleadings: Declaration of Christina M. Finn - Exhibit E", Dec. 6, 2008, pp. 1-17 (pdf pages).
GE Fanuc; "Pleadings: Declaration of Christina M. Finn - Exhibit F", Dec. 6, 2008, pp. 1-2 (pdf pages).
GE Fanuc; "Pleadings: Declaration of Christina M. Finn - Exhibit G", Dec. 6, 2008, pp. 1-2 (pdf pages).
GE Fanuc; "Pleadings: Declaration of Christina M. Finn - Exhibit H", Dec. 6, 2008, pp. 1-2 (pdf pages).
GE Fanuc; "Pleadings: Declaration of Christina M. Finn - Exhibit I", Dec. 6, 2008, pp. 1-9 (pdf pages).
GE Fanuc; "Pleadings: Declaration of Christina M. Finn - Exhibit J", Dec. 6, 2008, pp. 1-9 (pdf pages).
GE Fanuc; "Pleadings: Declaration of Christina M. Finn - Exhibit K", Dec. 6, 2008, pp. 1-8 (pdf pages).
GE Fanuc; "Pleadings: Declaration of Christina M. Finn - Exhibit L", Dec. 6, 2008, pp. 1-5 (pdf pages).
GE Fanuc; "Pleadings: Declaration of Melvin Ray Mercer", Dec. 6, 2008, pp. 1-34 (pdf pages).
GE Fanuc; "Pleadings: Declaration of Melvin Ray Mercer - Exhibit A", Dec. 6, 2008, pp. 1-22 (pdf pages).
GE Fanuc; "Pleadings: Declaration of Melvin Ray Mercer - Exhibit B", Dec. 6, 2008, pp. 1-2 (pdf pages).
GE Fanuc; "Pleadings: Declaration of Melvin Ray Mercer - Exhibit C", Dec. 6, 2008, pp. 1-2 (pdf pages).
GE Fanuc; "Pleadings: Declaration of Melvin Ray Mercer - Exhibit D", Dec. 6, 2008, pp. 1-2 (pdf pages).
GE Fanuc; "Pleadings: Declaration of Melvin Ray Mercer - Exhibit E", Dec. 6, 2008, pp. 1-2 (pdf pages).
GE Fanuc; "Pleadings: Declaration of Melvin Ray Mercer - Exhibit F", Dec. 6, 2008, pp. 1-5 (pdf pages).
GE Fanuc; "Pleadings: Declaration of Melvin Ray Mercer - Exhibit G", Dec. 6, 2008, pp. 1-8 (pdf pages).
Roy-G-Biv Corporation; "Pleadings: Plaintiff's Motion to Dismiss GE Fanuc Intelligenc Platforms, Inc. and General Electric Company's Infringement Claims or, Alternatively Motion to Sever", Jan. 8, 2009, pp. 1-7 (pdf pages).
GE Fanuc; "Pleadings: Defendant's Reply in Support of Their Motion to Stay the Litigation Plending the Outcome of the Reexamination Proceedings", Jan. 12, 2009, pp. 1-8 (pdf pages).
GE Fanuc; "Pleadings: Defendant's Reply in Support of Their Motion to Stay the Litigation Plending the Outcome of the Reexamination Proceedings - Exhibit 1", Jan. 12, 2009, pp. 1-2 (pdf pages).
GE Fanuc; "Pleadings: Defendant's Reply in Support of Their Motion to Stay the Litigation Plending the Outcome of the Reexamination Proceedings - Exhibit 2", Jan. 12, 2009, pp. 1-2 (pdf pages).
GE Fanuc; "Pleadings: Defendant's Reply in Support of Their Motion to Stay the Litigation Plending the Outcome of the Reexamination Proceedings - Exhibit 3", Jan. 12, 2009, pp. 1-2 (pdf pages).
US Dist Court Edtx, Marshal Div; "Order: Order Resetting Markman Date", Jan. 14, 2009, p. 1.
Roy-G-Biv Corporation; "Pleadings: Plaintiff's Opposition to Defendant's Motion to Stay the Litigation Pending the Outcome of the Reexamination Proceedings (Corrected)", Jan. 27, 2009, pp. 1-8 (pdf pages).

Roy-G-Biv Corporation; "Pleadings: Plaintiff's Second Set of Interrogatories (Nos. 17-18) for Each Defendant", Feb. 6, 2009, pp. 1-4.
Roy-G-Biv Corporation; Pleadings: Plaintiff Opening Markman Brief - Exhibit 5, Nov. 21, 2008, pp. 1-50.
Roy-G-Biv Corporation; Pleadings: Plaintiff Opening Markman Brief - Exhibit 5, Nov. 21, 2008, pp. 51-92.
Folsom, D,; "Order: Judgment Dismissing Action By Reason of Settlement", Oct. 19, 2009, US Dist Court EDTX, Marshal Div, pp. 1-2.
Folsom, D.; "Order: Reopen and Dismissal of Case", Nov. 20, 2009, US Dist Court EDTX, Marshal, Div, p.1.
Health Hero Network, Inc.; "USPTO Patent FileHist: P213698 (U.S. Appl. No. 08/944,529) File History", Oct. 7, 1997, Now Abandoned (123 pages).
Roy-G-Biv Corporation; "USPTO Patent FileHist: P210652 (U.S. Appl. No. 09/191,981) File History", Nov. 13, 1998, Now Abandoned (290 pages).
Roy-G-Biv Corporation; "USPTO Patent FileHist: P213781 (U.S. Appl. No. 09/882,800) File History", Jun. 14, 2001, Now Abandoned (132 pages).
Roy-G-Biv Corporation; "USPTO Patent FileHist: P214064 (U.S. Appl. No. 10/074,552) File History", Feb. 11, 2002, Now Abandoned (115 pages).
Roy-G-Biv Corporation; "USPTO Patent FileHist: P214119 (U.S. Appl. No. 10/150,237) File History", May 17, 2002, Now Abandoned (39 pages).
Roy-G-Biv Corporation; "USPTO Patent FileHist: P214185 (U.S. Appl. No. 10/405,883) File History", Apr. 1, 2003, Pending (1144 pages).
Roy-G-Biv Corporation; "USPTO Patent FileHist: P214321 (U.S. Appl. No. 10/409,393) File History", Apr. 7, 2003, Now Abandoned (140 pages).
Roy-G-Biv Corporation; "USPTO Patent FileHist: P214322 (Ussn: 10/412,166) File History", Apr. 10, 2003, Now Abandoned (282 pages).
Roy-G-Biv Corporation; "USPTO Patent FileHist: P214408 (U.S. Appl. No. 10/643,533) File History", Aug. 18, 2003, Now Abandoned (282 pages).
Roy-G-Biv Corporation; "USPTO Patent FileHist: P214760 (U.S. Appl. No. 11/067,327) File History", Feb. 25, 2005, Now Abandoned (311 pages).
Roy-G-Biv Corporation; "USPTO Patent FileHist: P215062 (U.S. Appl. No. 11/368,231) File History", Mar. 3, 2006, Now Abandoned (113 pages).
Roy-G-Biv Corporation; "USPTO Patent FileHist: P215032 (U.S. Appl. No. 11/370,082) File History", Mar. 6, 2006, Pending (1226 pages).
Roy-G-Biv Corporation; "USPTO Patent FileHist: P215031 (U.S. Appl. No. 11/375,502) File History", Mar. 13, 2006, Pending (1306 pages).
Roy-G-Biv Corporation; "USPTO Patent FileHist: P215322 (U.S. Appl. No. 11/583,233) File History", Oct. 18, 2006, Now Abandoned (664 pages).
Roy-G-Biv Corporation; "USPTO Patent FileHist: P215429 (U.S. Appl. No. 11/728,801) File History", Mar. 26, 2007, Pending (1338 pages).
Roy-G-Biv Corporation; "USPTO Patent FileHist: P216068 (U.S. Appl. No. 12/271,724) File History", Nov. 14, 2008, Pending (361 pages).
Roy-G-Biv Corporation; "USPTO Patent FileHist: P216258 (U.S. Appl. No. 12/546,566) File History", Aug. 24, 2009, Pending (646 pages).
USPTO; "USPTO Patent FileHist: P215032 (U.S. Appl. No. 11/370,082) File History - Office Action", Mar. 16, 2010, pp. 1-88.
USPTO; "ReEx: U.S. Patent No. 6,941,543 Inter-Partes Reexamination (Control No. 95/000,397) - Granted", Nov. 25, 2008, all pages.
USPTO; "ReEx: U.S. Patent No. 6,516,236 Reexamination (Control No. 95/000,396) - Non-Final Office Action", Jan. 23, 2009, all pages.
USPTO; "ReEx: U.S. Patent No. 6,513,058 Reexamination (Control No. 95/000,398) - Non-Final Office Action", Jan. 29, 2009, all pages.
USPTO; "ReEx: U.S. Patent No. 6,941,543 Reexamination (Control No. 95/000,397) - Non-Final Office Action", Jan. 29, 2009, all pages.
USPTO; "ReEx: U.S. Patent No. 5,691,897 Reexamination (Control No. 90/009,282) - Non-Final Office Action", Feb. 4, 2009, all pages.
USPTO; "ReEx: U.S. Patent No. 5,691,897 Reexamination (Control No. 90/009,282) - Decision for Petition for Extension of Time", Feb. 12, 2009, all pages.
Black, Lowe and Graham; "ReEx: U.S. Patent No. 6,941,543 Reexamination (Control No. 95/000,397) - Decision on Petition Extension For Time", Feb. 12, 2009, all pages.
Black, Lowe and Graham; "ReEx: U.S. Patent No. 6,516,236 Reexamination (Control No. 95/000,396) - Decision for Petition For Extension of Time", Feb. 13, 2009, all pages.
USPTO; "ReEx: U.S. Patent No. 6,513,058 Reexamination (Control No. 95/000,398) - Decision for Petition For Extension of Time", Feb. 17, 2009, all pages.
Ard, J.; "ReEx: U.S. Patent No. 5,691,897 Reexamination (Control No. 90/009,282) - Response Declaration: Ard", Apr. 23, 2009, Black, Lowe and Graham, (declaration - 8 pages) and (supporting Exhibits A-BB - 237 pages). See supporting Exhibit CC listed in "RGRX__06 Exhibit Index".
National Electrical Manufacturers Association; "ReEx: Malina Exhibit B - Excerpts from NEMA Motion Control Handbook", Nov. 1, 1992, all pages.
Armstrong Teasdale LLP; "ReEx: U.S. Patent No. 5,691,897 Reexamination (Control No. 90/009,282) - Third Party Request", Sep. 23, 2008, all pages.
Armstrong Teasdale LLP; "ReEx: U.S. Patent No. 6,513,058 Reexamination (Control No. 95/000,398) - Third Party Request", Sep. 23, 2008, all pages.
Armstrong Teasdale LLP; "ReEx: U.S. Patent No. 6,516,236 Reexamination (Control No. 95/000,396) - Third Party Request", Sep. 23, 2008, all pages.
USPTO; "ReEx: U.S. Patent No. 5,691,897 Reexamination (Control No. 90/009,282) - Notice of Assignment of Request", Sep. 26, 2008, pp. 1-2.
USPTO; "ReEx: U.S. Patent No. 6,516,236 Reexamination (Control No. 95/000,396) - Notice of Assignment of Request", Oct. 2, 2008, all pages.
USPTO; "ReEx: U.S. Patent No. 6,513,058 Reexamination (Control No. 95/000,398) - Notice of Assignment of Request", Oct. 6, 2008, all pages.
USPTO; "ReEx: U.S. Patent No. 5,691,897 Ex-Partes Reexamination (Control No. 90/009,282) - Granted", Nov. 10, 2008, all pages.
USPTO; "ReEx: U.S. Patent No. 6,516,236 Inter-Partes Reexamination (Control No. 95/000,396) - Granted", Nov. 20, 2008, all pages.
USPTO; "ReEx: U.S. Patent No. 6,513,058 Inter-Partes Reexamination (Control No. 95/000,398) - Granted", Nov. 25, 2008, all pages.
Chouinard, D.; "ReEx: U.S. Patent No. 5,691,897 Reexamination (Control No. 90/009,282) - Response Declaration: Chouinard", Apr. 23, 2009, (declaration - 8 pages) and (supporting Exhibit A - 4 pages).
Levy, A.; "ReEx: U.S. Patent No. 5,691,897 Reexamination (Control No. 90/009,282) - Response Declaration: Levy", Apr. 23, 2009, (declaration - 9 pages) and (supporting Exhibits A-C - 7 pages).
Malina, R.; "ReEx: U.S. Patent No. 5,691,897 Reexamination (Control No. 90/009,282) - Response Declaration: Malina", Apr. 23, 2009, (declaration - 34 pages) and (supporting Exhibits A-F - 19 pages).
Mathias, R.; "ReEx: U.S. Patent No. 5,691,897 Reexamination (Control No. 90/009,282) - Response Declaration: Mathias", Apr. 23, 2009, (declaration - 73 pages). See supporting Exhibits AA1-AA3, Y1-Y25, and Z1-Z10 - listed in "RGRX__06 Exhibit Index".
McConnel, S.; "ReEx: U.S. Patent No. 5,691,897 Reexamination (Control No. 90/009,282) - Response Declaration: McConnell", Apr. 23, 2009, (12 pages).
Omoigui, N.; "ReEx: U.S. Patent No. 5,691,897 Reexamination (Control No. 90/009,282) - Response Declaration: Omoigui", Apr. 23, 2009, (declaration - 22 pages) and (supporting Exhibit C - 8 pages). See supporting Exhibits A-B -listed in "RGRX__06 Exhibit Index".
Petzold, C.; "ReEx: U.S. Patent No. 5,691,897 Reexamination (Control No. 90/009,282) - Response Declaration: Petzold", Apr. 23, 2009, (declaration - 12 pages) and (supporting Exhibit A-B, where Ehxibit B includes sub-exhbits A-G - 78 pages).
Richter, J.; "ReEx: U.S. Patent No. 5,691,897 Reexamination (Control No. 90/009,282) - Response Declaration: Richter", Apr. 23, 2009, (declaration - 27 pages) and (supporting Exhibits A-B where Exibit B includes sub-exhibits A-G - 80 pages).

Stone, M.; "ReEx: U.S. Patent No. 5,691,897 Reexamination (Control No. 90/009,282) - Response Declaration: Stone", Apr. 23, 2009, (declaration - 13 pages) and (supporting Exhibit a - 4 pages).

Black, Lowe and Graham; "ReEx: U.S. Patent No. 6,516,236 Reexamination (Control No. 95/000,396) -Certificate of Service", Apr. 23, 2009, all pages.

Black, Lowe and Graham; "ReEx: U.S. Patent No. 6,516,236 Reexamination (Control No. 95/000,396) - Fee Transmittal", Apr. 23, 2009, all pages.

Black, Lowe and Graham; "ReEx: U.S. Patent No. 6,516,236 Reexamination (Control No. 95/000,396) - Information Disclosure Statement", Apr. 23, 2009, all pages.

Ard, J.; "ReEx: U.S. Patent No. 6,516,236 Reexamination (Control No. 95/000,396) - Response Declaration: Ard", Apr. 23, 2009, (declaration - 8 pages) and (supporting Exhibits A-BB - 237 pages). See supporting Exhibit CC listed in "RGRX_06 Exhibit Index".

Chouinard, D.; "ReEx: U.S. Patent No. 6,516,236 Reexamination (Control No. 95/000,396) - Response Declaration: Chouinard", Apr. 23, 2009, (declaration - 8 pages) and (supporting Exhibit A - 4 pages).

Levy, A.; "ReEx: U.S. Patent No. 6,516,236 Reexamination (Control No. 951000,396) - Response Declaration: Levy", Apr. 23, 2009, (declaration - 9 pages) and (supporting Exhibits A-C - 7 pages).

Malina, R.; "ReEx: U.S. Patent No. 6,516,236 Reexamination (Control No. 95/000,396) - Response Declaration:Malina", Apr. 23, 2009, (declaration - 34 pages) and (supporting Exhibits A-F - 19 pages).

Mathias, R.; "ReEx: U.S. Patent No. 6,516,236 Reexamination (Control No. 951000,396) - Response Declaration: Mathias", Apr. 23, 2009, (declaration - 74 pages). See supporting Exhibits AA1-AA3, Y1-Y25, and Z1-Z10 - listed in "RGRX_06 Exhibit Index".

Mcconnel, S.; "ReEx: U.S. Patent No. 6,516,236 Reexamination (Control No. 95/000,396) - Response Declaration: McConnell", Apr. 23, 2009, (12 pages).

Omoigui, N.; "ReEx: U.S. Patent No. 6,516,236 Reexamination (Control No. 95/000,396) - Response Declaration: Omoigui",Apr. 23, 2009, (declaration - 22 pages) and (supporting Exhibit C - 8 pages). See supporting Exhibits A-B - listed in "RGRX_06 Exhibit Index".

Petzold, C.; "ReEx: U.S. Patent No. 6,516,236 Reexamination (Control No. 95/000,396) - Response Declaration: Petzold", Apr. 23, 2009, (declaration - 12 pages) and (supporting Exhibit A-B, where Ehxibit B includes sub-exhbits A-G - 78 pages).

Richter, J.; "ReEx: U.S. Patent No. 6,516,236 Reexamination (Control No. 951000,396) - Response Declaration: Richter", Apr. 23, 2009, (declaration - 27 pages) and (supporting Exhibits A-B where Exibit B includes sub-exhibits A-G - 80 pages).

Stone, M.; "ReEx: U.S. Patent No. 6,516,236 Reexamination (Control No. 951000,396) - Response Declaration: Stone", Apr. 23, 2009, (declaration - 13 pages) and (supporting Exhibit A - 4 pages).

Black, Lowe and Graham; "ReEx: U.S. Patent No. 6,516,236 Reexamination (Control No. 95/000,396) -Transmittal Letter", Apr. 23, 2009, all pages.

Black, Lowe and Graham; "ReEx: U.S. Patent No. 6,513,058 Reexamination (Control No. 95/000,398) -Certificate of Service", Apr. 28, 2009, all pages.

Black, Lowe and Graham; "ReEx: U.S. Patent No. 6,513,058 Reexamination (Control No. 95/000,398) - Fee Transmittal", Apr. 28, 2009, all pages.

Black, Lowe and Graham; "ReEx: U.S. Patent No. 6,513,058 Reexamination (Control No. 95/000,398) - Information Disclosure Statement", Apr. 28, 2009, all pages.

Ard, J.; "ReEx: U.S. Patent No. 6,513,058 Reexamination (Control No. 95/000,398) - Response Declaration: Ard", Apr. 28, 2009, (declaration - 8 pages) and (supporting Exhibits A-BB - 237 pages). See supporting Exhibit CC listed in "RGRX_06 Exhibit Index".

Chouinard, D.; "ReEx: U.S. Patent No. 6,513,058 Reexamination (Control No. 95/000,398) - Response Declaration: Chouinard", Apr. 28, 2009, (declaration - 8 pages) and (supporting Exhibit A - 4 pages).

Levy, A.; "ReEx: U.S. Patent No. 6,513,058 Reexamination (Control No. 95/000,398) - Response Declaration: Levy", Apr. 28, 2009, (declaration - 9 pages) and (supporting Exhibits A-C - 7 pages).

Malina, R.; "ReEx: U.S. Patent No. 6,513,058 Reexamination (Control No. 95/000,398) - Response Declaration: Malina", Apr. 28, 2009, (declaration - 34 pages) and (supporting Exhibits A-F - 19 pages).

Mathias, R.; "ReEx: U.S. Patent No. 6,513,058 Reexamination (Control No. 95/000,398) - Response Declaration: Mathias", Apr. 28, 2009, See supporting Exhibits AA1-AA3, Y1-Y25, and Z1-Z10 - listed in "RGRX_06 Exhibit Index".

Mcconnel, S.; "ReEx: U.S. Patent No. 6,513,058 Reexamination (Control No. 95/000,398) - Response Declaration: McConnell", Apr. 28, 2009, (12 pages).

Omoigui, N.; "ReEx: U.S. Patent No. 6,513,058 Reexamination (Control No. 95/000,398) - Response Declaration: Omoigui", Apr. 28, 2009, (declaration - 22 pages). See supporting Exhibits A-B - listed in "RGRX_06 Exhibit Index".

Petzold, C.; "ReEx: U.S. Patent No. 6,513,058 Reexamination (Control No. 95/000,398) - Response Declaration: Petzold", Apr. 28, 2009, (declaration - 11 pages) and (supporting Exhibit A-B, where Ehxibit B includes sub-exhbits A-G - 78 pages).

Richter, J.; "ReEx: U.S. Patent No. 6,513,058 Reexamination (Control No. 95/000,398) - Response Declaration: Richter", Apr. 28, 2009, (declaration - 27 pages) and (supporting Exhibits A-B where Exibit B includes sub-exhibits A-G - 80 pages).

Stone, M.; "ReEx: U.S. Patent No. 6,513,058 Reexamination (Control No. 95/000,398) - Response Declaration: Stone", Apr. 28, 2009, (declaration - 13 pages) and (supporting Exhibit A - 4 pages).

USPTO; "ReEx: U.S. Patent No. 6,513,058 Reexamination (Control No. 95/000,398) - Returned Postcards", Apr. 28, 2009, all pages.

Black, Lowe and Graham; "ReEx: U.S. Patent No. 6,513,058 Reexamination (Control No. 95/000,398) - Transmittal Letter", Apr. 28, 2009, all pages.

Black, Lowe and Graham; "ReEx: U.S. Patent No. 6,941,543 Reexamination (Control No. 95/000,397) -Information Disclosure Statement", Apr. 28, 2009, all pages.

Black, Lowe and Graham; "ReEx: U.S. Patent No. 6,513,058 Reexamination (Control No. 95/000,398) -Response after Non-Final Office Action", Apr. 29, 2009, all pages.

Black, Lowe and Graham; "ReEx: U.S. Patent No. 6,941,543 Reexamination (Control No. 95/000,397) - Certificate of Service", Apr. 29, 2009, all pages.

Black, Lowe and Graham; "ReEx: U.S. Patent No. 6,941,543 Reexamination (Control No. 95/000,397) - Fee Transmittal", Apr. 29, 2009, all pages.

Black, Lowe and Graham; "ReEx: U.S. Patent No. 6,941,543 Reexamination (Control No. 95/000,397) - Response after Non-Final Office Action", Apr. 29, 2009, all pages.

Ard, J.; "ReEx: U.S. Patent No. 6,941,543 Reexamination (Control No. 95/000,397) - Response Declaration: Ard", Apr. 29, 2009, (declaration - 8 pages) and (supporting Exhibits A-BB - 237 pages). See supporting Exhibit CC listed in "RGRX_06 Exhibit Index".

Chouinard, D.; "ReEx: U.S. Patent No. 6,941,543 Reexamination (Control No. 95/000,397) - Response Declaration: Chouinard", Apr. 29, 2009, (declaration - 8 pages) and (supporting Exhibit A - 4 pages).

Levy, A.; "ReEx: U.S. Patent No. 6,941,543 Reexamination (Control No. 95/000,397) - Response Declaration: Levy", Apr. 29, 2009, (declaration - 9 pages) and (supporting Exhibits A-C - 7 pages).

Malina, R.; "ReEx: U.S. Patent No. 6,941,543 Reexamination (Control No. 95/000,397) - Response Declaration: Malina", Apr. 29, 2009, (declaration - 34 pages) and (supporting Exhibits A-F - 19 pages).

Mathias, R.; "ReEx: U.S. Patent No. 6,941,543 Reexamination (Control No. 95/000,397) - Response Declaration: Mathias", Apr. 29, 2009, (declaration - 73 pages). See supporting Exhibits AA1-AA3, Y1-Y25, and Z1-Z10 - listed in "RGRX_06 Exhibit Index".

McConnel, S.; "ReEx: U.S. Patent No. 6,941,543 Reexamination (Control No. 95/000,397) - Response Declaration: McConnell", Apr. 29, 2009, (12 pages).

Omoigui, N.; "ReEx: U.S. Patent No. 6,941,543 Reexamination (Control No. 95/000,397) - Response Declaration: Omoigui", Apr. 29, 2009, (22 pages) and (supporting Exhibit C - 8 pages). See supporting Exhibits A-B - listed in "RGRX_06 Exhibit Index".

Petzold, C.; "ReEx: U.S. Patent No. 6,941,543 Reexamination (Control No. 95/000,397) - Response Declaration: Petzold", Apr. 29, 2009, (declaration - 12 pages) and (supporting Exhibit A-B, where Ehxibit B includes sub-exhbits A-G - 78 pages).

Richter, J.; "ReEx: U.S. Patent No. 6,941,543 Reexamination (Control No. 95/000,397) - Response Declaration: Richter", Apr. 29, 2009, (declaration - 27 pages) and (supporting Exhibits A-B where Exibit B includes sub-exhibits A-G - 80 pages).

Stone, M.; "ReEx: U.S. Patent No. 6,941,543 Reexamination (Control No. 95/000,397) - Response Declaration: Stone", Apr. 29, 2009, (declaration - 13 pages) and (supporting Exhibit A - 4 pages).

USPTO; "ReEx: U.S. Patent No. 6,941,543 Reexamination (Control No. 95/000,397) - Returned Postcards", Apr. 29, 2009, all pages.

Black, Lowe and Graham; "ReEx: U.S. Patent No. 6,941,543 Reexamination (Control No. 95/000,397) - Transmittal Letter", Apr. 29, 2009, all pages.

Black, Lowe and Graham; "ReEx: U.S. Patent No. 5,691,897 Reexamination (Control No. 90/009,282) - Certificate of Service", May 1, 2009, all pages.

Black, Lowe and Graham; "ReEx: U.S. Patent No. 5,691,897 Reexamination (Control No. 90/009,282) - Fee Transmittal", May 1, 2009, all pages.

Black, Lowe and Graham; "ReEx: U.S. Patent No. 5,691,897 Reexamination (Control No. 90/009,282) - Information Disclosure Statement", May 1, 2009, all pages.

Black, Lowe and Graham; "ReEx: U.S. Patent No. 5,691,897 Reexamination (Control No. 90/009,282) - Response after Non-Final Office Action", May 1, 2009, all pages.

Black, Lowe and Graham; "ReEx: U.S. Patent No. 5,691,897 Reexamination (Control No. 90/009,282) - Transmittal Letter", May 1, 2009, all pages.

USPTO; "ReEx: U.S. Patent No. 5,691,897 Reexamination (Control No. 90/009,282) - Returned Postcards", May 6, 2009, all pages.

Armstrong Teasdale Llp; "ReEx: U.S. Patent No. 6,516,236 Reexamination (Control No. 95/000,396) - Third Party Requester Comments after Non-Final Office Action", May 22, 2009, all pages.

Individual; "ReEx: U.S. Patent No. 6,516,236 Reexamination (Control No. 95/000,396) - Third Party Requester Comments after Non-Final Office Action: Exhibits A-1 thru A-47", May 22, 2009, all pages.

Individual; "ReEx: U.S. Patent No. 6,516,236 Reexamination (Control No. 95/000,396) - Third Party Requester Comments after Non-Final Office Action: Exhibits B thru Q", May 22, 2009, all pages. See transcript - Contains multiple refs. with varying pub. dates. Exh Q not provided by requestor.

Individual; "ReEx: U.S. Patent No. 6,513,058 Reexamination (Control No. 95/000,398) - Third Party Certificate of Mailing", May 28, 2009, all pages.

Armstrong Teasdale LLP; "ReEx: U.S. Patent No. 6,513,058 Reexamination (Control No. 95/000,398) - Third Party Requester Comments after Non-Final Office Action", May 28, 2009, all pages.

Individual; "ReEx: U.S. Patent No. 6,513,058 Reexamination (Control No. 95/000,398) - Third Party Requester Comments after Non-Final Office Action: Exhibits A-1 thru A-55", May 28, 2009, all pages.

Individual; "ReEx: U.S. Patent No. 6,513,058 Reexamination (Control No. 95/000,398) - Third Party Requester Comments after Non-Final Office Action: Exhibits B thru S", May 28, 2009, all pages.

Armstrong Teasdale LLP; "ReEx: U.S. Patent No. 6,941,543 Reexamination (Control No. 951000,397) - Third Party Requester Comments after Non-Final Office Action", May 29, 2009, all pages.

Individual; "ReEx: U.S. Patent No. 6,941,543 Reexamination (Control No. 95/000,397) - Third Party Requester Comments after Non-Final Office Action: Exhibits T thru V", May 29, 2009, all pages.

Individual; "ReEx: U.S. Patent No. 6,513,058 Reexamination (Control No. 95/000,398) - Third Party Certificate of Service", Jun. 11, 2009, all pages.

Individual; "ReEx: U.S. Patent No. 6,516,236 Reexamination (Control No. 95/000,396) - Third Party Certificate of Service", Jun. 11, 2009, all pages.

Individual; "ReEx: U.S. Patent No. 6,513,058 Reexamination (Control No. 95/000,398) - Petition and Request for Return of 3rd Party Req. Comments Without Consideration", Jun. 12, 2009, all pages.

Black, Lowe and Graham; "ReEx: U.S. Patent No. 6,516,236 Reexamination (Control No. 95/000,396) - Petition and Request of 3rd Party Req. Comments Without Consideration", Jun. 12, 2009, all pages.

Armstrong Teasdale LLP; "ReEx: U.S. Patent No. 6,941,543 Reexamination (Control No. 95/000,397) - Third Party Request", Sep. 23, 2009, all pages.

USPTO; "ReEx: U.S. Patent No. 5,691,897 Reexamination (Control No. 90/009,282) - Final Office Action", Jan. 13, 2010, all pages.

USPTO; "ReEx: U.S. Patent No. 6,516,236 Reexamination (Control No. 95/000,396) - Non-Final Office Action #2", Feb. 4, 2010, all pages.

USPTO; "ReEx: U.S. Patent No. 6,941,543 Reexamination (Control No. 95/000,397) - Non-Final Office Action #2", Feb. 4, 2010, all pages.

USPTO; "ReEx: U.S. Patent No. 6,513,058 Reexamination (Control No. 95/000,398) - Non-Final Office Action #2", Feb. 8, 2010, all pages.

Black, Lowe and Graham; "ReEx: U.S. Patent No. 6,516,236 Reexamination (Control No. 95/000,396) - Response after Non-Final Office Action", Feb. 16, 2010, all pages.

Black, Lowe and Graham; "ReEx: U.S. Patent No. 6,513,058 Reexamination (Control No. 95/000,398) - Response after PTO's Notice Dated Feb. 4, 2010", Feb. 19, 2010 (52 pages).

Black, Lowe and Graham; "ReEx: U.S. Patent No. 6,513,058 Reexamination (Control No. 95/000,397) - Response after PTO's Notice Dated Feb. 4, 2010", Feb. 19, 2010 (59 pages).

Roy-G-Biv Corporation; "ReEx: RGRX_06 Exhibit Index", Feb. 24, 2010, (7 pages).

Black, Lowe and Graham; "ReEx: U.S. Patent No. 5,691,897 Reexamination (Control No. 95/009,282) - Response after Final Office Action", Mar. 12, 2010, 43 pages.

Black, Lowe and Graham; "ReEx: U.S. Patent No. 6,516,236 Reexamination (Control No. 95/000,396) - Response after PTO's Notice Dated Feb. 4, 2010", Mar. 19, 2010 (56 pages).

Stegburger, W.; "Intertask-Communication Inside A Real-Time Database", 1989, IFAC Distributed Databases in Real-time, pp. 63-69.

Sycara, K.; Pannu, A.; Williamson, M.; Zeng, D.; "Distributed Intelligent Agents - 1", Dec. 1, 1996, IEEE Expert, Downloaded from IEEE, 11(6): pp. 36-46.

Sycara, K.; Pannu, A.; Williamson, M.; Zeng, D.; "Distributed Intelligent Agents - 2", Dec. 1, 1996, IEEE Expert, (Downloaded from CiteSeer) 11(6): 36-46.

Think and Do Software, Inc.; "Think and Do Smart Distributed System Brochure", May 18, 1998, pp. 1-2, (document creation date May 18, 1998).

Rockwell Automation; "Interchange for Windows Release Notes", Jun. 1, 1999, pp. 1-14.

EPO; "FileHist: European Patent Application No. EP04816957 - Search Report", Mar. 24, 2010, (4 pages).

Roy-G-Biv Corporation; "USPTO Patent FileHist: P214185 (U.S. Appl. No. 10/405,883) File History; Amend after Final Rejection Office Action", Mar. 29, 2010, (6 pages).

USPTO; "USPTO Patent FileHist: 7110.00002 (U.S. Appl. No. 12/263,953) File History; Non-Final Office Action", Mar. 31, 2010, (476 pages).

Roy-G-Biv Corporation; "USPTO Patent FileHist: P215031 (U.S. Appl. No. 11/375,502) File History; Response After Oct. 1, 2009 Non-Final Office Action", Mar. 31, 2010, (13 pages).

Roy-G-Biv Corporation; "USPTO Patent FileHist: P215057 (U.S. Appl. No. 11/454,053) File History; Supp Amend after Non-Final Office Action", Apr. 1, 2010, (15 pages).

Roy-G-Biv Corporation; "USPTO Patent FileHist: P215057 (U.S. Appl. No. 11/454,053) File History; Supp Amend after Non-Final Office Action", Apr. 5, 2010, (8 pages).

Richter, J.; "Advanced Windows NT - The Developer's Guide to the Win32 Application Programming Interface", 1994, Microsoft Press, (732 pages) Copyright 1994.

Kruglinski, D.; "Inside Visual C++- Version 1.5; Second Edition", 1994, Microsoft Press, (754 pages) Copyright 1994.

Microsoft Press; "Microsoft Windows NT(TM) 3.5 Guidelines for Security, Audit, and Control", 1994, (296 pages) Copyright 1994.

Brockschmidt, K.; "Inside OLE - Second Edition", 1995, Microsoft Press, (1236 pages) Copyright 1995.

Kruglinski, D.; "Inside Visual C++- The Standard Reference for Programming with Microsoft Visual C++ version 4", 1996, Microsoft Press, (946 pages) Copyright 1996.

Chappell, D.; "Understanding ActiveX and OLE - A Guide for Developers and Managers", 1996, Microsoft Press, (347 pages) Copyright 1996.

Redmond III, F.; "DCOM - Microsoft Distributed Component Object Model", Sep. 22, 1997, IDG Books Worldwide, Inc., (371 pages) Copyright 1997.

USPTO; "USPTO Patent FileHist: P214185 (U.S. Appl. No. 10/405,883) File History; Notice of Allowance", Apr. 19, 2010, (58 pages).

Roy-G-Biv Corporation; "USPTO Patent FileHist: P215057 (U.S. Appl. No. 11/454,053) File History - Remarks", Apr. 23, 2010, 2 pages.

Roy-G-Biv Corporation; "USPTO Patent FileHist: P215057 (U.S. Appl. No. 11/454,053) File History - Supplemental Amendment After Non-Final Rejection", Apr. 23, 2010, 1 page.

Roy-G-Biv Corporation; "USPTO Patent FileHist: P215057 (U.S. Appl. No. 11/454,053) File History - Terminal Disclaimer", Apr. 23, 2010, 2 pages.

Roy-G-Biv Corporation; "USPTO Patent FileHist: P216039 (U.S. Appl. No. 12/244,673) File History - Remarks", Apr. 23, 2010, 2 pages.

Roy-G-Biv Corporation; "USPTO Patent FileHist: P216039 (U.S. Appl. No. 12/244,673) File History - Supplemental Amendment After Non-Final Rejection", Apr. 23, 2010, 1 page.

Roy-G-Biv Corporation; "USPTO Patent FileHist: P216039 (U.S. Appl. No. 12/244,673) File History - Terminal Disclaimer", Apr. 23, 2010, 2 pages.

Popovic, D.; Bhatkar, V.; "Distributed Computer Control for Industrial Automation", 1990, Marcel Dekker, Inc., (721 pages).

Amy, L.; "Automation Systems for Control and Data Acquisition", 1992, Instrument Society of America, (235 pages).

Shinskey, F.; "Process Control Systems: Application, Design, and Tuning - Fourth Edition", 1996, McGraw-Hill Inc., (450 pages).

Johnson, C,; "Process Control Instrumentation Technology - Fifth Edition", 1997, Prentice-Hall, Inc., (645 pages).

USPTO; "USPTO Patent FileHist: P215429 (U.S. Appl. No. 11/728,801) - Notice of Allowance", Jun. 16, 2010, (72 pages).

USPTO; "ReEx: U.S. Patent No. 5,691,897 Reexamination (Control No. 90/009,282) - Examiner Interview Summary", May 12, 2010, (9 pages).

Roy-G-Biv Corporation; "ReEx: U.S. Patent No. 5,691,897 Reexamination (Control No. 90/009,282) - Supplemental Response to Final Office Action", May 18, 2010, (48 pages).

USPTO; "ReEx: U.S. Patent No. 5,691,897 Reexamination (Control No. 90/009,282) - Examiner Advisory Action", May 24, 2010, (5 pages).

USPTO; "USPTO Patent FileHist: P216068 (U.S. Appl. No. 12/271,724) - Office Action", Apr. 27, 2010, (153 pages).

JPO; "Japanese Patent Application No. JP2003513348 - FileHist: Office Action", Jun. 10, 2010, (13 pages).

Roy-G-Biv Corporation; "USPTO Patent FileHist: P215032 (U.S. Appl. No. 11/370,082) File History - Response to Office Action", Jul. 16, 2010, (10 pages).

USPTO; "USPTO Patent FileHist: P215031 (U.S. Appl. No. 11/375,502) File History; Final Office Action", Jul. 21, 2010, (195 pages).

Roy-G-Biv Corporation; "ReEx: U.S. Patent No. 5,691,897 Ex-Partes Reexamination (Control No. 90/009,282) - Appeal Brief", Jul. 12, 2010, (75 pages).

* cited by examiner

FIG. 6

SPEAK: SAY OK WHEN YOU ARE READY {LF}
RECOGNIZE: OK {LF}
SPEAK: PLEASE REMEMBER TO TAKE YOUR
    INSULIN ON TIME {LF}
DELAY: 3 {LF}
SPEAK: REMEMBER TO MEASURE YOUR BLOOD SUGAR
    BEFORE BREAKFAST EACH MORNING {LF}
DELAY: 3 {LF}
SPEAK: IT IS IMPORTANT TO EXERCISE EVERY DAY {LF}
DELAY: 3 {LF}
SPEAK: MANAGING DIABETES IS TOUGH BUT
    YOU CAN DO IT {LF}
DELAY: 3 {LF}
SPEAK: THAT'S ALL THE NEWS FOR NOW {LF}
DELAY: 1 {LF}
SPEAK: CONNECT ME TO THE TELEPHONE LINE
    TO GET NEW MESSAGES {LF}
{EOF}

FIG. 7

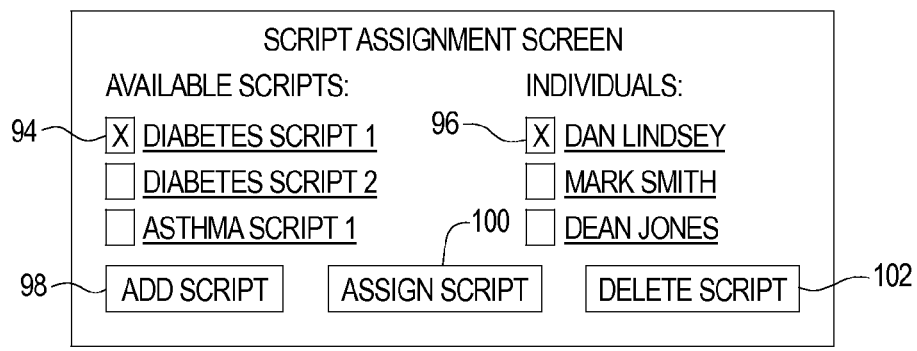

FIG. 13

SPEAK: SAY OK WHEN YOU ARE READY {LF}
RECOGNIZE: OK {LF}
SPEAK: <<INSERT PATIENT_NAME>> PLEASE REMEMBER TO TAKE
          YOUR <<INSERT MEDICATION_NAME>> ON TIME {LF}
DELAY: 3 {LF}
SPEAK: <<INSERT PATIENT_NAME>> REMEMBER TO MEASURE YOUR
          <<INSERT MEASURED_PARAMETER>> EACH DAY {LF}
DELAY: 3 {LF}
SPEAK: MANAGING <<INSERT DISEASE_NAME>> IS TOUGH
          BUT YOU CAN DO IT <<INSERT PATIENT_NAME>> {LF}
DELAY: 3 {LF}
SPEAK: THAT'S ALL THE NEWS FOR NOW {LF}
DELAY: 1 {LF}
SPEAK: CONNECT ME TO THE TELEPHONE LINE
          TO GET NEW MESSAGES {LF}
{EOF}

FIG. 14

SPEAK: SAY OK WHEN YOU ARE READY {LF}
RECOGNIZE: OK {LF}
SPEAK: DAN PLEASE REMEMBER TO TAKE
          YOUR INSULIN ON TIME {LF}
DELAY: 3 {LF}
SPEAK: DAN REMEMBER TO MEASURE YOUR
          BLOOD SUGAR EACH DAY {LF}
DELAY: 3 {LF}
SPEAK: MANAGING DIABETES IS TOUGH
          BUT YOU CAN DO IT DAN {LF}
DELAY: 3 {LF}
SPEAK: THAT'S ALL THE NEWS FOR NOW {LF}
DELAY: 1 {LF}
SPEAK: CONNECT ME TO THE TELEPHONE LINE
          TO GET NEW MESSAGES {LF}
{EOF}

REMOTE GENERATION AND DISTRIBUTION OF COMMAND PROGRAMS FOR PROGRAMMABLE DEVICES

RELATED APPLICATIONS

This application is a continuation of U.S. patent application Ser. No. 09/780,316 filed on Feb. 9, 2001, now abandoned, which claims priority of U.S. Provisional Patent Application Ser. No. 60/181,577 filed on Feb. 10, 2000, and is a continuation-in-part of U.S. patent application Ser. No. 08/944,529 filed Oct. 7, 1997, now abandoned. The contents of all related applications listed above are incorporated herein by reference.

TECHNICAL FIELD

The present invention relates to control systems for programmable devices and, more particularly, to the generation and distribution of control commands that control the operation of programmable devices.

BACKGROUND OF THE INVENTION

A wide variety of devices contain a combination of software and hardware that control the operation of the device. These devices will be referred to herein as programmable devices. Programmable devices include a wide variety of items such as toys, industrial motion control systems, exercise equipment, medical devices, household appliances, HVAC systems, and the like.

A common characteristic of such programmable devices is that they are programmed to perform a limited number of predetermined tasks. For example, a toy may be programmed to speak, move, or react to external stimulation in a predetermined manner. An industrial motion control system is programmed to assemble parts in a precise, repetitive manner. A household appliance may be programmed to perform one or more cooking or cleaning tasks. An HVAC system will be programmed to control a heating element and heat distribution systems to obtain a desired air temperature.

Some programmable devices contain means for allowing the end user to control the functionality of the system to a limited degree. In the context of a toy, the end user may operate a switch or joystick to select a manner of movement. An HVAC system will normally allow the end user to set the desired temperature. In most cases, however, the input of the end user is limited to changing variables or selecting from among a plurality of stand-alone programs.

Programmable devices thus take many forms but have certain common characteristics. A programmable device includes some form of memory for storing control commands that define a predetermined command program. The command program may accept input from the user or contain discrete sub-programs from which the end user may select, but the end user may not modify the command program.

A programmable device further comprises a processor capable of executing the command program and generating control signals. To reduce manufacturing costs, the processor is normally an inexpensive dedicated processor with relatively limited capabilities and resources.

A programmable device will also comprise control hardware that performs a desired task as defined by the control signals. The control hardware can be as simple as an LED or speaker that generates light or sound or as complicated as a multi-axis industrial motion control device that performs a complex welding procedure.

The relevance of the present invention is particularly significant given the varying degrees of technical skill possessed by the various patient end users involved in the design, manufacturing, and use of a typical programmable device. The user of a programmable device must be assumed to have little or no capability to create the command programs necessary to operate a programmable device. Certainly a typical child using a toy will not have the skills necessary to create command program for that toy. Even a highly trained technician operating an industrial motion control system typically will likely not have the skill to program the system to perform a desired task.

Accordingly, in this application the term "end user" will refer to a person who uses a programmable device but cannot be assumed to have the expertise to create a command program for that programmable device.

In contrast, the term "programmer" will be used herein to refer to a person having the expertise to create a command program for a particular programmable device. The skill level and background of the programmer will vary depending upon the specific programmable device; the term programmer is thus not intended to define a particular level of expertise, but is instead defined in relation to the specific programmable device.

With some programmable devices, the programmer has no direct contact with the end user. For example, a programmer of a toy or household appliance will typically not have direct contact with the end user. A programmer of an HVAC system or industrial motion control system may, on the other hand, have contact with the end user.

Without direct contact with the end user, the programmer must anticipate what task the end user will desire of the programmable device. Even with direct contact, the programmer may not fully comprehend the desired task, or the desired task may change after the command program has been created. In either case, obtaining the services of the programmer to modify the command program is likely to be difficult and expensive, if not impossible.

In general, while the end user may not be able to create a command program, the end user will be able to define the desired task. A technician operating an industrial motion control system will likely be able to observe that a change in the operation of the system will increase product yield or speed up the manufacturing process. Even a child might be able to determine that a doll that walks should also be able to jump.

The term "end user" may include any other person involved with a programmable device without the technical expertise to qualify as a programmer of that device. For example, a medical device may be used by a patient and controlled by a caregiver, neither of which would have the expertise to be considered a programmer; both the patient and the caregiver would be considered end users in the present application.

The purpose of the present invention is to facilitate the generation and distribution of command programs for programmable devices. In particular, the present invention is designed to allow an end user of a particular programmable device to define a desired task, interact with a remote computer over a communications network to generate a command program, and then download the command program into the programmable device over the communications network.

SUMMARY OF THE INVENTION

The present invention may be embodied as a system for controlling a motion device. A motion control system comprises a motion control device, and a first user is associated with the motion control system. An output system is arranged to generate motion signals that may be perceived by the first user. A motion server system comprises a plurality of motion scripts associated with messages to be transmitted to the first user and a motion program web page. A processing system comprises a browser program compatible with the motion program web page. A communications system transfers data between the various systems. A second user controls the server system to form a motion message corresponding to a desired motion signal based on the at least one motion script stored by the server system. The motion control system causes the output system to generate the desired motion signal based on the motion message.

BRIEF DESCRIPTION OF THE DRAWINGS

FIG. 6 is a listing of a sample script program according to the preferred embodiment of the invention.

FIG. 7 is a script assignment screen according to the preferred embodiment of the invention.

FIG. 13 is a listing of a generic script program according to the second embodiment of the invention.

FIG. 14 is a listing of a custom script program according to the second embodiment of the invention.

DETAILED DESCRIPTION

The present invention may be embodied in any programmable device. The present invention will be described below in the context of a toy that may be programmed to speak or move in a desired fashion. The present invention has application to other programmable devices, and the scope of the present invention should be determined by the claims appended hereto and not the following discussion.

The invention may be embodied as a networked system including one or more programmable toys that can be controlled to perform a desired task such as move and/or communicate messages to end users. In contrast to conventional programmable toys whose desired task is programmed during manufacture or through the insertion of external media, the programmable toys of the present invention are programmed remotely through the use of script programs. The script programs allow flexible and dynamic updating of the movement of or messages delivered by the toys, as well as convenient tailoring of toy movement and/or the communicated messages to the needs of particular end users.

In an example embodiment of the invention disclosed below, the end users as described above are patients and healthcare providers, and the programmable toys are remotely programmed to encourage healthy behavior in the patients. The terms "patient" and "health care provider" will be used below interchangeably with the term end user.

In the present exemplary embodiment, the programmable toys may be programmed to encourage children to take their medicine or to tolerate difficult healthcare regimens. The encouragement can take the form of a request audibly delivered to the patient in the form of speech and feedback in the form of movement when the request is followed.

As generally discussed throughout this application, the system of the present invention is equally well suited for purposes other than healthcare, such as industrial motion control systems, exercise equipment, HVAC systems, advertising, home appliances, education, entertainment, or any other application which involves the control of programmable devices to perform a desired task for an end user.

Figure 1:
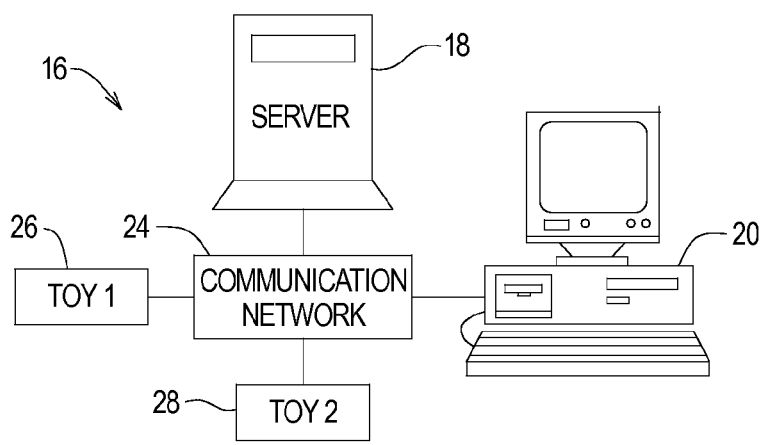
FIG. 1 is a block diagram of a networked system according to a preferred embodiment of the invention.

The preferred embodiment of the invention is illustrated in FIGS. 1-7. Referring to FIG. 1, a networked system 16 includes a server 18 and a workstation 20 connected to server 18 through a communication network 24. Server 18 is preferably a world wide web server and communication network 24 is preferably the Internet. It will be apparent to one skilled in the art that server 18 may comprise a single stand-alone computer or multiple computers distributed throughout a network. Workstation 20 is preferably a personal computer, remote terminal, or web TV unit connected to server 18 via the Internet. Workstation 20 functions as a remote interface for entering in server 18 the end task to be performed for the benefit of the end user.

System 16 also includes first and second programmable toys 26 and 28. Each programmable toy interacts with a patient end user in accordance with script programs received from server 18. Each programmable toy is connected to server 18 through communication network 24, preferably the Internet. Alternatively, the programmable toys may be placed in communication with server 18 via wireless communication networks, cellular networks, telephone networks, or any other network which allows each programmable toy to exchange data with server 18. For clarity of illustration, only two programmable toys are shown in FIG. 1. It is to be understood that system 16 may include any number of programmable toys for communicating messages to any number of patient end users.

In general, a healthcare provider end user will operate the workstation 20, a programmer will design and operate the server 18, and the patient end user will use the toys 26 and 28.

Figure 2:
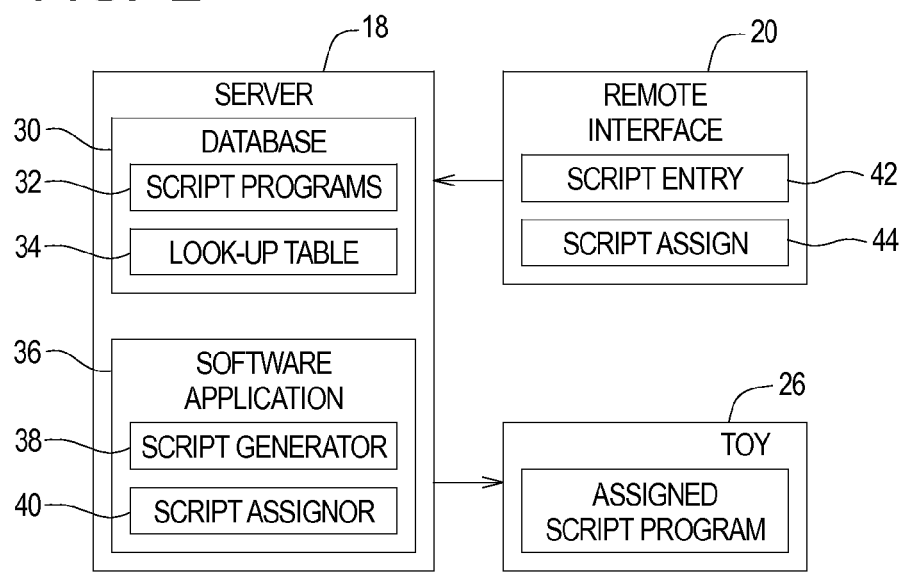
FIG. 2 is a block diagram illustrating the interaction of the components of the system of FIG. 1.

FIG. 2 shows server 18, workstation 20, and programmable toy 26 in greater detail. Server 18 includes a database 30 for storing script programs 32. The script programs are executed by the programmable toys to communicate messages to the patients. Database 30 further includes a look-up table 34. Table 34 contains a list of the patients who are to receive messages, and for each of the patient end user, a unique identification code and a respective pointer to the script program assigned to the end user. Each programmable toy is designed to execute assigned script programs which it receives from server 18.

Figure 3:
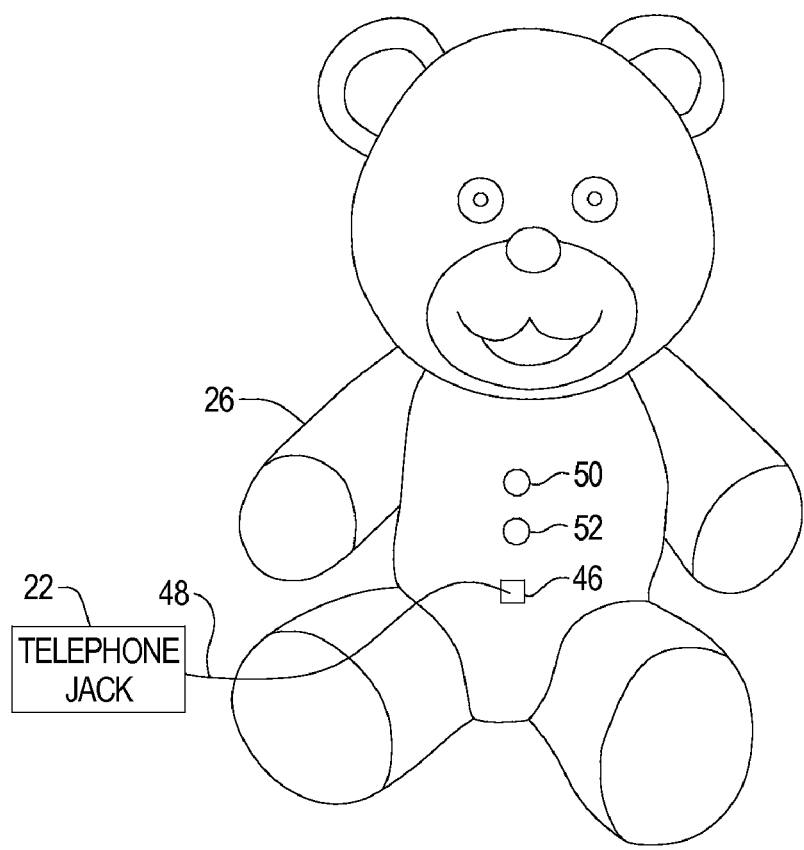
FIG. 3 is a perspective view of a remotely programmable talking toy of the system of FIG. 1.
Figure 4:
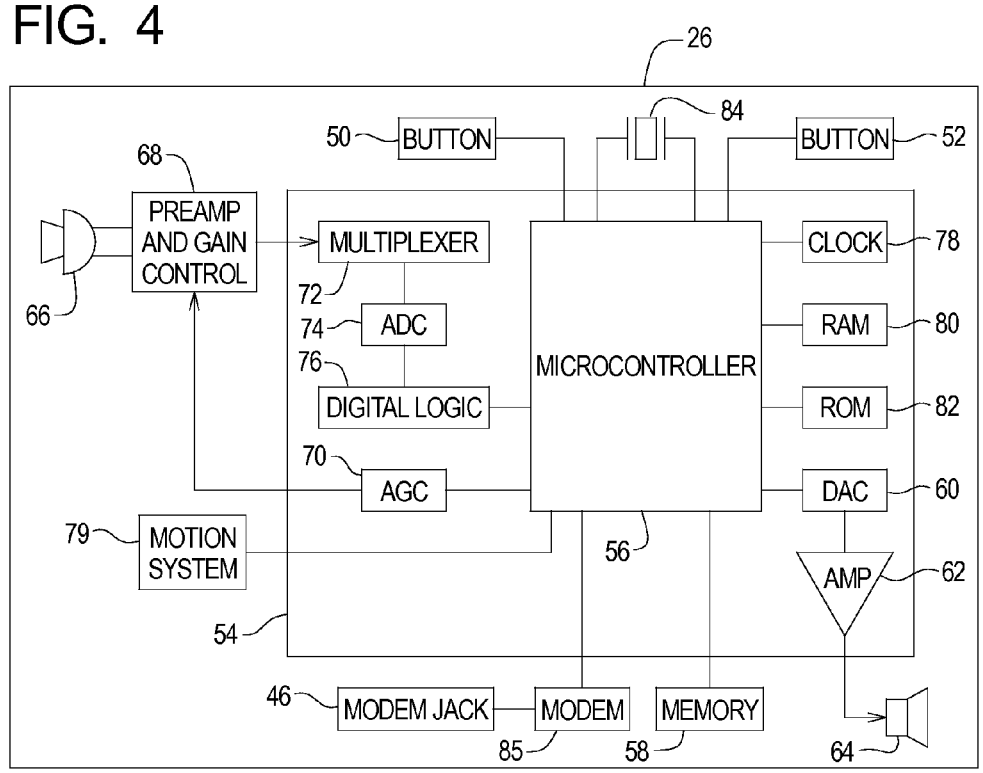
FIG. 4 is a block diagram illustrating the components of the talking toy of FIG. 3.

FIGS. 3-4 show the structure of each programmable toy according to the preferred embodiment. For clarity, only programmable toy 26 is illustrated since each programmable toy of the exemplary preferred embodiment has substantially identical structure to toy 26. Referring to FIG. 3, toy 26 is preferably embodied as a doll, such as a teddy bear. Alternatively, toy 26 may be embodied as an action figure, robot, or any other desired toy.

Toy 26 includes a modem jack 46 for connecting the toy to a telephone jack 22 through a connection cord 48. Toy 26 also includes first and second user control buttons 50 and 52. Button 50 is pressed to instruct the toy to execute a script program. Button 52 is pressed to instruct the toy to establish a communication link to the server and download a new script program. In alternative embodiments, the control buttons may be replaced by switches, keys, sensors, or any other type of interface suitable for receiving user input.

FIG. 4 is a schematic block diagram illustrating the internal components of toy 26. Toy 26 includes an audio processor chip 54, which is preferably an RSC-164 chip commercially available from Sensory Circuits Inc. of 1735 N. First Street, San Jose, Calif. 95112. Audio processor chip 54 has a microcontroller 56 for executing script programs received from the server. A memory 58 is connected to microcontroller 56. Memory 58 stores the end user's unique identification code, script programs received from the server, and a script interpreter used by microcontroller 56 to execute the script programs.

The script interpreter translates script commands into the native processor code of microcontroller 56. Specific techniques for translating and executing script commands in this manner are well known in the art. Memory 58 also stores a control program executed by microcontroller 56 to perform various control functions which are described in the operation section below. Memory 58 is preferably a non-volatile memory, such as a serial EEPROM.

Toy 26 also includes a modem 85 which is connected between microcontroller 56 and modem jack 46. Modem 85 operates under the control of microcontroller 56 to establish communication links to the server through the communication network and to exchange data with the server. The data includes the end user's unique identification code which modem 85 transmits to the server, as well as assigned script programs which modem 85 receives from the server. Modem 85 is preferably a complete 28.8 K modem commercially available from Cermetek, although any suitable modem may be used.

Toy 26 further includes a speaker 64 and a microphone 66. Audio processor chip 54 has built in speech synthesis functionality for audibly communicating messages and prompts to an end user through speaker 64. For speech synthesis, chip 54 includes a digital to analog converter (DAC) 60 and an amplifier 62. DAC 60 and amplifier 62 drive speaker 64 under the control of microcontroller 56 to communicate the messages and prompts.

Audio processor chip 54 also has built in speech recognition functionality for recognizing responses spoken into microphone 66. Audio signals received through microphone 66 are converted to electrical signals and sent to a preamp and gain control circuit 68. Circuit 68 is controlled by an automatic gain control circuit 70, which is in turn controlled by microcontroller 56. After being amplified by preamp 68, the electrical signals enter chip 54 and pass to through a multiplexer 72 and an analog to digital converter (ADC) 74. The resulting digital signals pass through a digital logic circuit 76 and enter microcontroller 56 for speech recognition.

Audio processor chip 54 also includes a RAM 80 for short term memory storage and a ROM 82 which stores audio sounds for speech synthesis and programs executed by microcontroller 56 to perform speech recognition and speech synthesis. Chip 54 operates at a clock speed determined by a crystal 84. Chip 54 further includes a clock 78 which provides the current date and time to microcontroller 56. Microcontroller 56 is also connected to control buttons 50 and 52 to receive user input. Toy 26 is preferably powered by one or more batteries (not shown). Alternatively, the toy may be powered by a standard wall outlet. Both methods for supplying power to a toy are well known in the art.

The toy 26 further comprises a motion system 79 that receives control signals from the microcontroller 56. The motion system 79 can be similar to the motion system used in the "FURBY" doll; this system 79 allows the toy 26 to shake, move its hands and feet, and open and close its mouth and eyes. The motion system 79 is well-known in the art, but is conventionally preprogrammed at the factory for particular ranges and sequences of movement.

Referring again to FIG. 2, server 18 includes a controlling software application 36 which is executed by server 18 to perform the various functions described below. The controlling software application 36 may be a system for generating a sequence of control commands based on an application program for motion control systems such as is disclosed in U.S. Pat. Nos. 5,867,385 and 5,691,897 to Brown et al., which are incorporated herein by reference.

The controlling software application 36 includes a script generator 38 and a script assignor 40. Script generator 38 is designed to generate script programs 32 from script information entered through workstation 20. The script programs 32 are a specific type of command program such as those typically executed by programmable devices. The script programs 32 contain the information necessary for the microcontroller 56 to cause the toy 26 to perform a desired task.

The script information is entered through a script entry screen 42. In the preferred embodiment, script entry screen 42 is implemented as a web page on server 18. Workstation 20 includes a web browser for accessing the web page to enter the script information.

Figure 5:
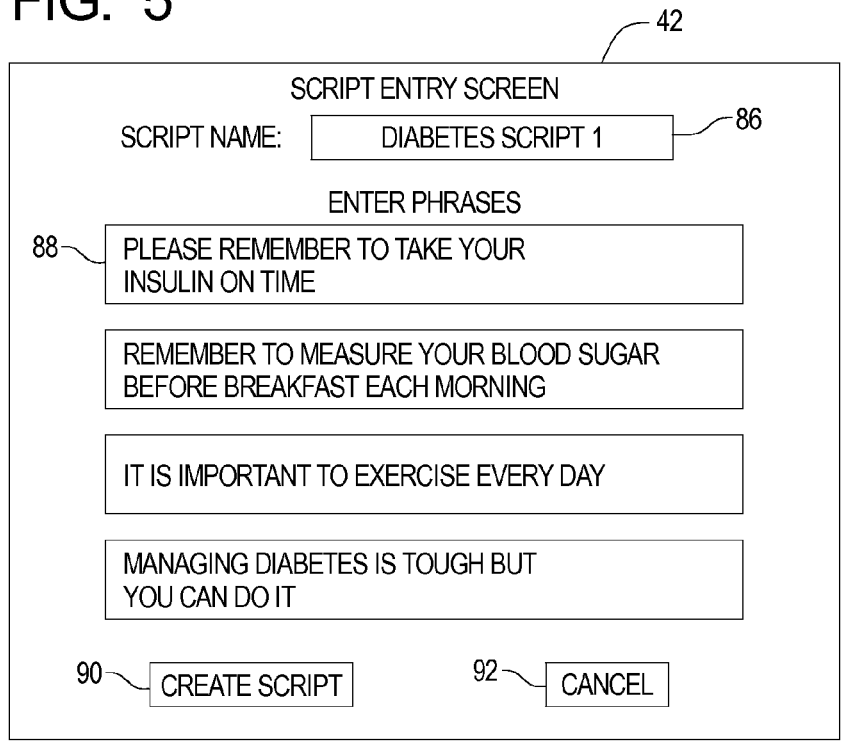
FIG. 5 is a script entry screen according to the preferred embodiment of the invention.

FIG. 5 illustrates a sample script entry screen 42 as it appears on workstation 20. Screen 42 includes a script name field 86 for specifying the name of a script program to be generated. Screen 42 also includes entry fields 88 for entering information defining the desired task, such as a message containing instructions from the healthcare provider end user to be communicated to the patient end user and a movement to be performed when patient end user complies with the instructions.

FIG. 5 illustrates an exemplary set of statements which encourage the end user to comply with his or her diabetes care regimen. However, it is to be understood that any type of desired task may be entered in screen 42, including movement, sounds, or other messages such as advertisements, educational messages, and entertainment messages. Screen 42 further includes a CREATE SCRIPT button 90 for instructing the script generator to generate a script program from the information entered in screen 42. Screen 42 also includes a CANCEL button 92 for canceling the information entered.

In the preferred embodiment, each script program created by the script generator conforms to the standard file format used on UNIX systems. In the standard file format, each command is listed in the upper case and followed by a colon.

Every line in the script program is terminated by a linefeed character {LF}, and only one command is placed on each line. The last character in the script program is a UNIX end of file character {EOF}. Table 1 shows an exemplary listing of script commands used in the preferred embodiment of the invention.

TABLE 1

SCRIPT COMMANDS

| Command | Description |
| --- | --- |
| SPEAK: {words} {LF} | Synthesize the words following the SPEAK command. |
| RECOGNIZE: {word} {LF} | Recognize the word following the RECOGNIZE command. |
| DELAY: t {LF} | Wait a period of seconds specified by time parameter t. |

The script commands illustrated in Table 1 are representative of the preferred embodiment and are not intended to limit the scope of the invention. After consideration of the ensuing description, it will be apparent to one skilled in the art many other suitable scripting languages and sets of script commands may be used to implement the invention.

Script generator 38 preferably stores a script program template which it uses to create each script program. To generate a script program, script generator 38 inserts into the template the information entered in screen 42. For example, FIG. 6 illustrates a sample script program created by the script generator from the script information shown in FIG. 5. The script program includes speech commands to synthesize the phrases or statements entered in fields 88. The steps included in the script program are also shown in the flow chart of FIG. 10 and will be discussed in the operation section below.

Referring again to FIG. 2, script assignor 40 is for assigning script programs 32 to the patient end users. Script programs 32 are assigned in accordance with script assignment information entered through workstation 30. The script assignment information is entered through a script assignment screen 44, which is preferably implemented as a web page on server 18.

FIG. 7 illustrates a sample script assignment screen 44 as it appears on workstation 20. Screen 44 includes check boxes 94 for selecting a script program to be assigned and check boxes 96 for selecting the patient end users to whom the script program is to be assigned. Screen 44 also includes an ASSIGN SCRIPT button 100 for entering the assignments. When button 100 is pressed, the script assignor creates and stores for each patient end user selected in check boxes 96 a respective pointer to the script program selected in check boxes 94. Each pointer is stored in the look-up table of the database. Screen 44 further includes an ADD SCRIPT button 98 for adding a new script program and a DELETE SCRIPT button 102 for deleting a script program.

Figure 8:
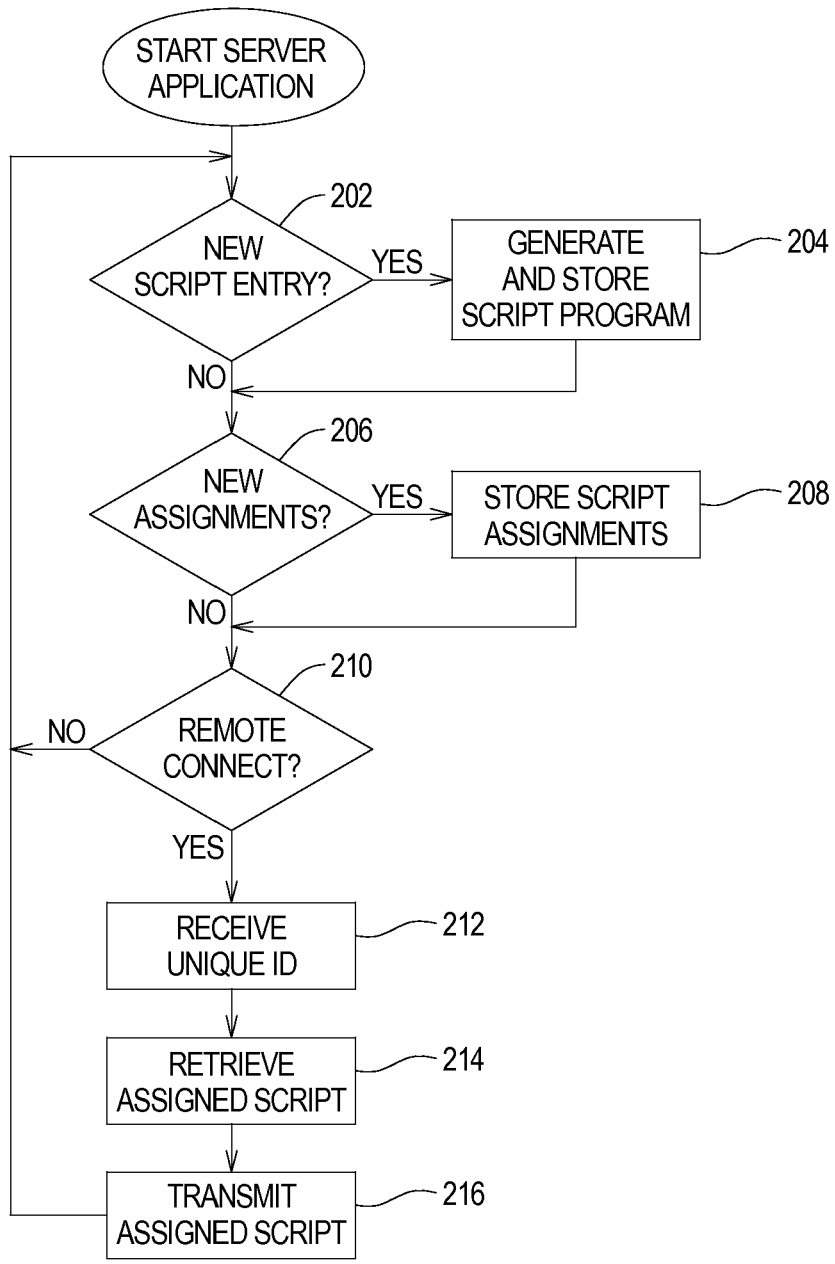
FIG. 8 is a flow chart illustrating the steps included in a software application executed by the server of FIG. 1 according to the preferred embodiment of the invention.

The operation of the preferred embodiment is illustrated in FIGS. 1-10. FIG. 8 is a flow chart illustrating the steps included in the software application executed by server 18. In step 202, server 18 determines if new script information has been entered through script entry screen 42. If new script information has not been entered, server 18 proceeds to step 206. If new script information has been entered, server 18 proceeds to step 204.

In the preferred embodiment, the script information is entered in server 18 by one or more healthcare provider end users, such as a physician or case manager assigned to the patient, as generally discussed above. Of course, any person desiring to communicate with the end users may be granted access to server to create and assign script programs.

Further, it is to be understood that the system may include any number of remote interfaces for entering script generation and script assignment information in server 18. In a toy created for entertainment rather than healthcare purposes, a child may log on to the server 18, custom design a script program, and download the program into the toy.

As shown in FIG. 5, the script information specifies a desired task, such as a message containing a set of statements or phrases, to be communicated to one or more patient end users. The desired task may further comprise movements selected and/or entered in a similar manner.

In step 204, the script generator 38 generates a script program from the information entered in screen 42. The script program is stored in database 30. Steps 202 and 204 are preferably repeated to generate multiple script programs, e. g. a script program for diabetes patients, a script program for asthma patients, etc. Each script program corresponds to a respective one of the sets of statements entered through script entry screen 42. In step 206, the server 18 determines if new script assignment has been entered through assignment screen 44. If new script assignment information has not been entered, server 18 proceeds to step 210. If new script assignment information has been entered server 18 proceeds to step 208.

As shown in FIG. 7, the script assignment information is entered by the healthcare provider end user by selecting a desired script program through check boxes 94, selecting the patient end users to whom the selected scrip program is to be assigned through check boxes 96, and pressing the ASSIGN SCRIPT button 100. When button 100 is pressed, script assignor 40 creates for each end user selected in check boxes 96 a respective pointer to the script program selected in check boxes 94. In step 208, each pointer is stored in look-up table 34 of database 30. In step 210, server 18 determines if any one of the programmable toys is remotely connected to the server.

Each patient end user is preferably provided with his or her own programmable toy which has the end user's unique identification code stored therein. Each patient end user is thus uniquely associated with a respective one of the programmable toys. If none of the programmable toys is connected, server 18 returns to step 202. If a programmable toy is connected, server 18 receives from the programmable toy the patient end user's unique identification code to retrieve from table 34 the pointer to the script program assigned to the patient end user. In step 214, server 18 retrieves the assigned script program from database 30. In step 216, server 18 transmits the assigned script program to the patient end user's programmable toy through communication network 24. Following step 216, the server returns to step 202.

Figure 9:
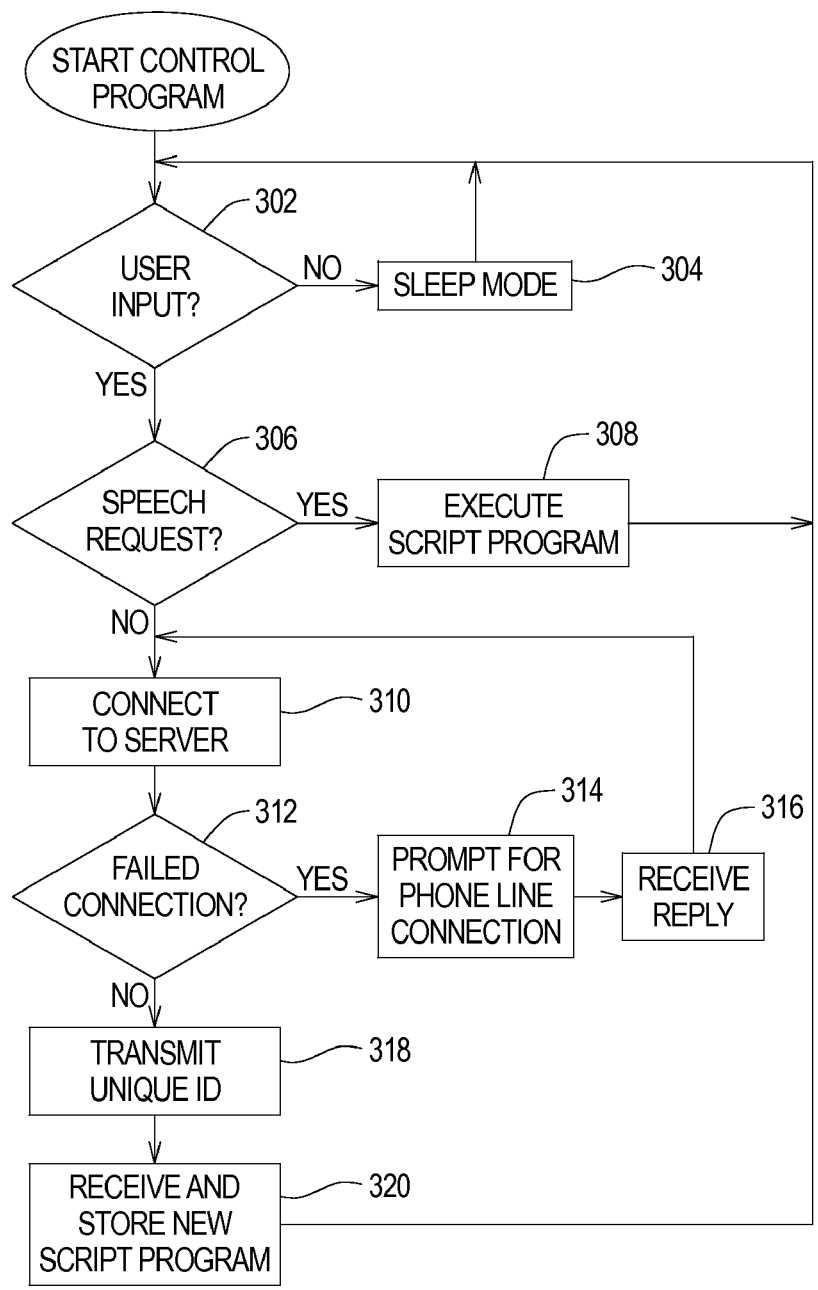
FIG. 9 is a flow chart illustrating the steps included in a control program executed by the talking toy of FIG. 3 according to the preferred embodiment of the invention.

Each programmable toy is initially programmed with its user's unique identification code, the script interpreter used by the toy to interpret and execute script program commands, and a control program executed by the toy to control its overall operation. The initial programming may be achieved during manufacture or during an initial connection to server 18. FIG. 9 illustrates the steps included in the control program executed by microcontroller 56 of programmable toy 26.

In step 302, microcontroller 56 determines if any user input has been received. In the preferred embodiment, user input is received through control buttons 50 and 52. Control button 50 is pressed to instruct the programmable toy to move and/or speak, and control button 52 is pressed to instruct the toy to connect to the server and download a new script program. If no user input is received for a predetermined period of time, such as two minutes, toy 26 enters sleep mode in step 304. The sleep mode conserves battery power while the toy is not in use. Following step 304, microcontroller 56 returns to step 302 and awaits user input.

If user input has been received, microcontroller 56 determines if the input is a task request, step 306. If the user has pressed control button 50, if microcontroller 56 executes the script program last received from the server, step 308. The steps included in a sample script program are shown in the flow chart of FIG. 10 and will be discussed below. Following step 308, microcontroller 56 returns to step 302 and awaits new user input.

If the user presses control button 52 requesting a connection to the server, microcontroller 56 attempts to establish a communication link to the server through modem 85 and communication network 24, step 310. In step 312, microcontroller determines if the connection was successful. If the connection failed, the user is prompted to connect toy 26 to telephone jack 22 in step 314. Microcontroller 56 preferably prompts the user by synthesizing the phrase "PLEASE CONNECT ME TO THE TELEPHONE JACK USING THE CONNECTION CORD AND SAY 'DONE' WHEN YOU HAVE FINISHED."

In step 316, microcontroller 56 waits until the appropriate reply is received through microphone 66. Upon recognizing the reply 'DONE', microcontroller 56 repeats step 310 to get a successful connection to the server. Once a successful connection is established, microcontroller 56 transmits the unique identification code stored in memory 58 to server 18 in step 318.

Figure 10:
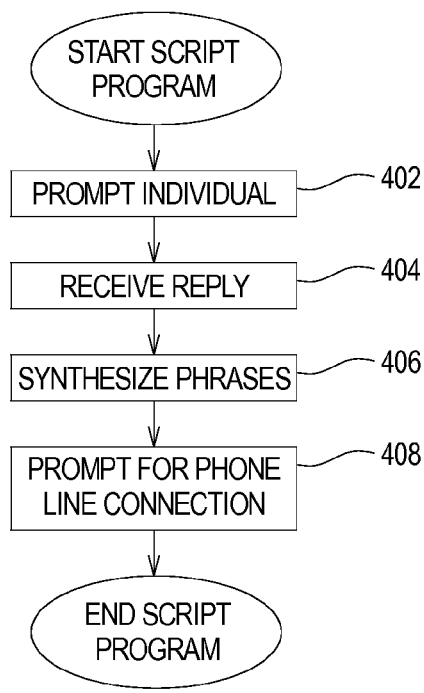
FIG. 10 is a flow chart illustrating the steps included in the script program of FIG. 6.

In step 320, microcontroller 56 receives a new script program from the server through communication network 24 and modem 85. The new script program is stored in memory 58 for subsequent execution by microcontroller 56. Following step 320, microcontroller 56 returns to step 302 and awaits new user input. FIG. 10 is a flow chart illustrating the steps included in a sample script program executed by microcontroller 56. In step 402, microcontroller 56 prompts the user by synthesizing through speaker 64 "SAY 'OK' WHEN YOU ARE READY". In step 404, microcontroller 56 waits until a reply to the prompt is received through the microphone 66. When the reply 'OK' is recognized, microcontroller 55 proceeds to step 406. If no reply is received within a predetermined period of time, such as two minutes, toy 26 preferably enters sleep mode until it is reactivated by pressing one of the control buttons.

In step 406, microcontroller 56 executes successive speech commands to synthesize through speaker 64 the phrases or statements specified in the script program. Referring again to FIG. 6, the speech commands are preferably separated by delay commands which instruct microcontroller 56 to pause for a number of seconds between statements. The number of seconds is selected to allow the user sufficient time to absorb each statement. Alternatively, the user may be prompted to acknowledge each statement before a subsequent statement is synthesized. For example, the script program may include commands which instruct microcontroller 56 to synthesize the phrase "SAY 'OK' WHEN YOU ARE READY TO HEAR THE NEXT STATEMENT." Upon recognizing the reply 'OK', microcontroller 56 proceeds to the next speech command in the script program. Movement commands are processed for execution by the motion system in a similar manner.

In step 408, the user is reminded to connect toy 26 to telephone jack 22 to download a new script program. Microcontroller 56 synthesizes through speaker 64 "PLEASE CONNECT ME TO THE TELEPHONE JACK TO GET NEW MESSAGES." Following step 408, the script program ends.

One advantage of the system of the present invention is that it allows each programmable toy to be programmed remotely through the use of script programs. This allows the task performed by each programmable toy to be tailored to the specific needs of a specific end user or group of end users. Moreover, each script program may be easily created, assigned, and downloaded by simply accessing a server through a communication network, such as the Internet. Thus, the invention provides a powerful, convenient, and inexpensive system for communicating messages to a large number of end users.

Figure 11:
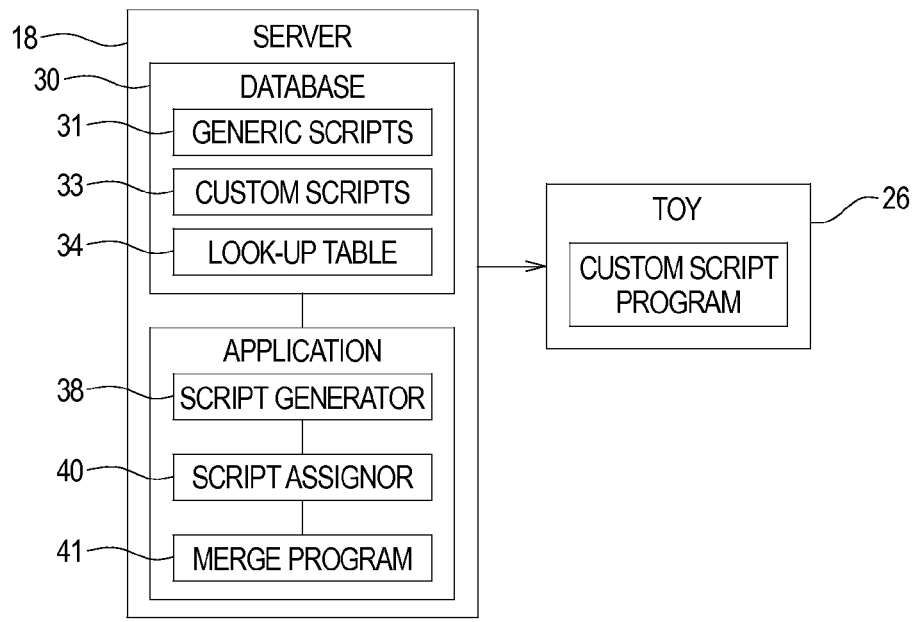
FIG. 11 is a block diagram illustrating the interaction of the server of FIG. 1 with the talking toy of FIG. 3 according to a second embodiment of the invention.

FIGS. 11-15 illustrate a second embodiment of the invention in which messages are further customized to each patient end user by merging personal data with the script programs, much like a standard mail merge application. Referring to FIG. 11, personal data relating to each patient end user is preferably stored in look-up table 34 of database 30. By way of example, the data may include each patient end user's name, the name of each patient end user's medication or disease, or any other desired data. As in the preferred embodiment, database 30 also stores generic script programs 31 created by script generator 38.

In the second embodiment, server 18 includes a data merge program 41 for merging the data stored in table 34 with generic script programs 31. Data merge program 41 is designed to retrieve selected data from table 34 and to insert the data into statements in generic script programs 31, thus creating custom script programs 33. Each custom script program contains a message which is customized to a patient end user. For example, the message may be customized with the patient end user's name, medication name, disease name, etc.

Figure 15:
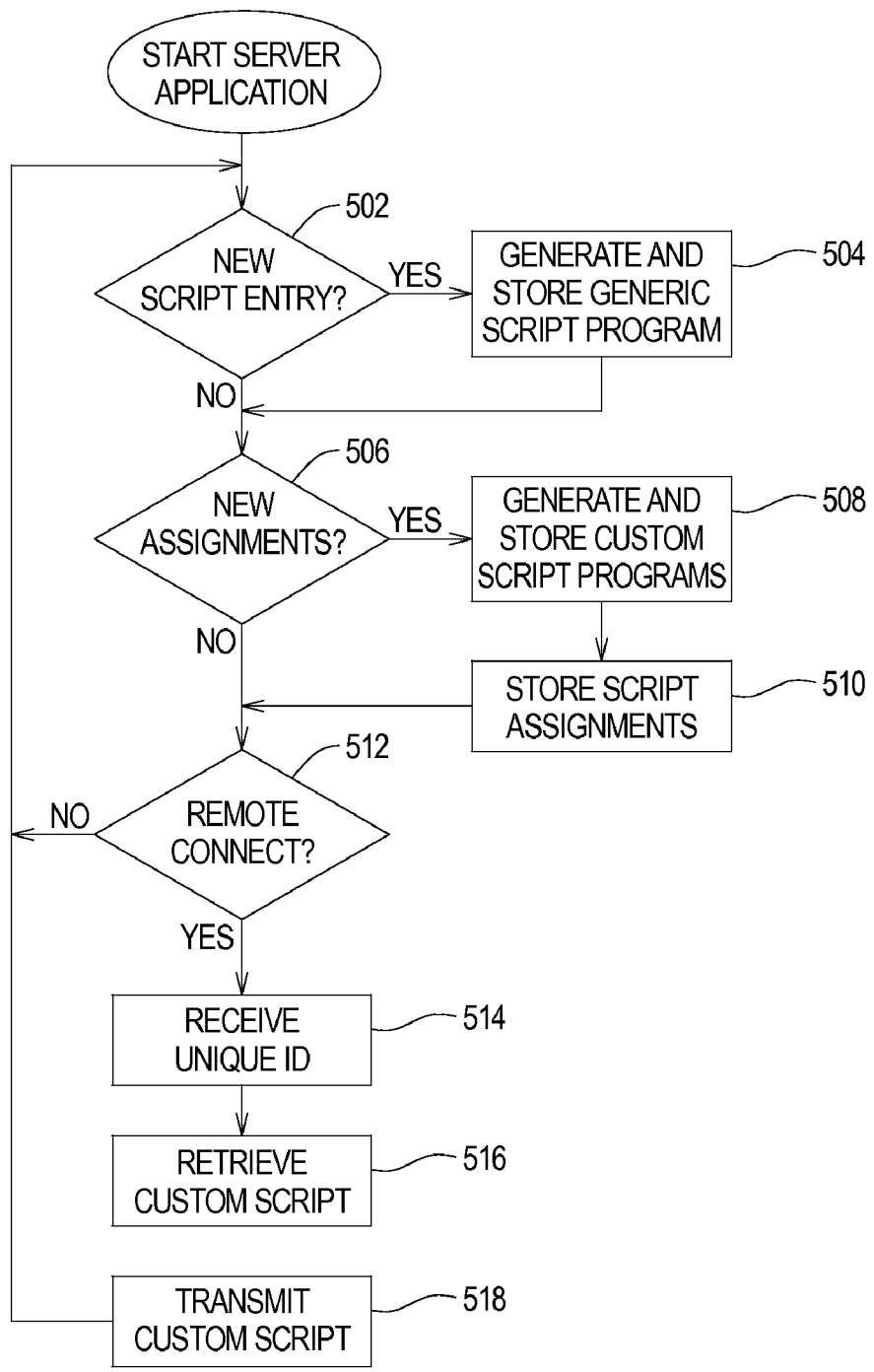
FIG. 15 is a flow chart illustrating the steps included in a software application executed by the server of FIG. 1 according to the second embodiment of the invention.

The operation of the second embodiment is illustrated in FIGS. 11-15. The operation of the second embodiment is similar to the operation of the preferred embodiment except that server 18 transmits custom script programs to each programmable toy rather than generic script programs. FIG. 15 is a flow chart illustrating the steps included in a software application executed by server 18 according to the second embodiment.

Figure 12:
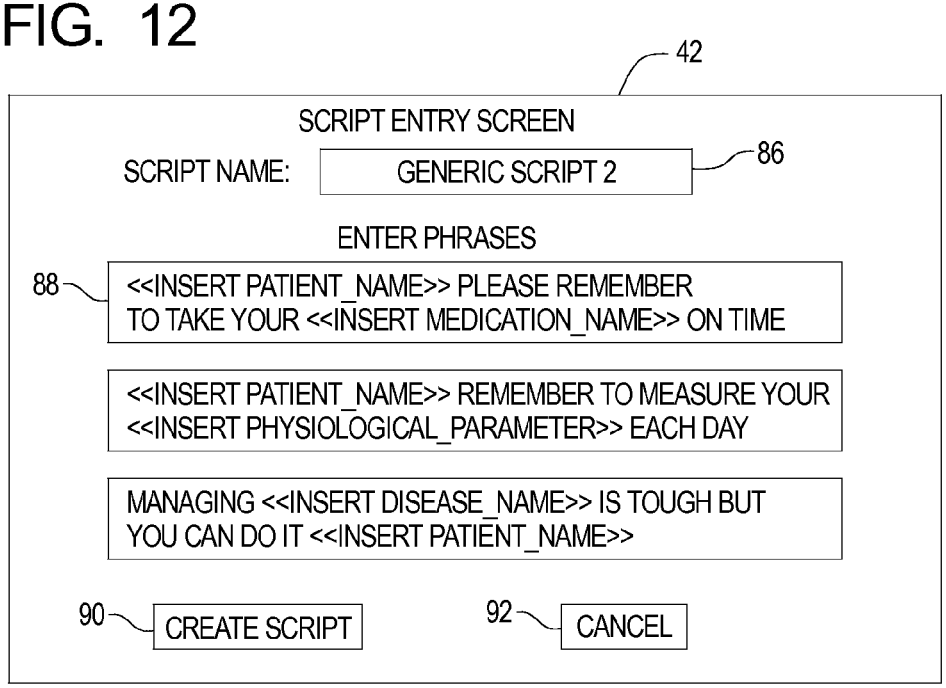
FIG. 12 is a script entry screen according to the second embodiment of the invention.

In step 502, server 18 determines if new script information has been entered through script entry screen 42. If new script information has not been entered, server 18 proceeds to step 506. If new script information has been entered, server 18 proceeds to step 504. As shown in FIG. 12, the script information specifies a message, such as a set of statements or phrases, to be communicated to the patient end users. Each statement preferably includes one or more insert commands specifying data from table 34 to be inserted into the statement. The insert commands instruct data merge program 41 to retrieve the specified data from database 30 and to insert the data into the statement. For example, the first statement shown in FIG. 12 includes insert commands instructing the data merge program to insert a patient name and a medication name into the statement.

Following entry of the statements and insert commands, CREATE SCRIPT button 90 is pressed. When button 90 is pressed, script generator 38 generates a generic script program from the information entered in screen 42, step 504. A sample generic script program is illustrated in FIG. 13. The generic script program includes speech commands to synthesize the statements entered in fields 88. Each statement preferably includes one or more insert commands specifying data to be inserted into the script program. The generic script program is stored in database 30.

In step 506, server 18 determines if new script assignment information has been entered through assignment screen 44. If new script assignment information has not been entered, server 18 proceeds to step 512. If new script assignment information has been entered, server 18 proceeds to step 508. As shown in FIG. 7, the script assignment information is entered by selecting a desired script program through check boxes 94, selecting the patient end users to whom the selected script program is to be assigned through check boxes 96, and pressing the ASSIGN SCRIPT button 100.

When button 100 is pressed, data merge program 41 creates a custom script program for each patient end user selected in check boxes 96, step 508. Each custom script program is preferably created by using the selected generic script program as a template. For each patient end user selected, data merge program 41 retrieves from database 30 the data specified in the insert commands. Next, data merge program 41 inserts the data into the appropriate statements in the generic script program to create a custom script program for the patient end user.

For example, FIG. 14 illustrates a custom script program created from the generic script program of FIG. 13. Each custom script program is stored in database 30.

As each custom script program is generated for a patient end user, script assignor 40 assigns the custom script program to the patient end user, step 510. This is preferably accomplished by creating a pointer to the custom script program and storing the pointer with the patient end user's unique identification code in table 34. In step 512, server 18 determines if any one of the programmable toys is remotely connected to the server. If a programmable toy is connected, server 18 receives from the programmable toy the patient end user's unique identification code in step 514.

Server 18 uses the received identification code to retrieve from table 34 the pointer to the custom script program assigned to the patient end user. In step 516, server 18 retrieves the custom script program from database 30. In step 518, server 18 transmits the custom script program to the patient end user's programmable toy. The programmable toy receives and executes the script program in the same manner described in the preferred embodiment. The remaining operation of the second embodiment is analogous to the operation of the preferred embodiment described above.

Although it is presently preferred to generate a custom script program for each patient end user as soon as script assignment information is received for the patient end user, it is also possible to wait until the patient end user's programmable toy s connects to the server before generating the custom script program. This is accomplished by creating and storing a pointer to the generic script program assigned to the patient end user, as previously described in the preferred embodiment. When the patient end user's programmable toy connects to the server, the data merge program creates a custom script program for the patient end user from the generic script program assigned to the patient end user. The custom script program is then transmitted to the patient end user's programmable toy for execution.

Figure 16:
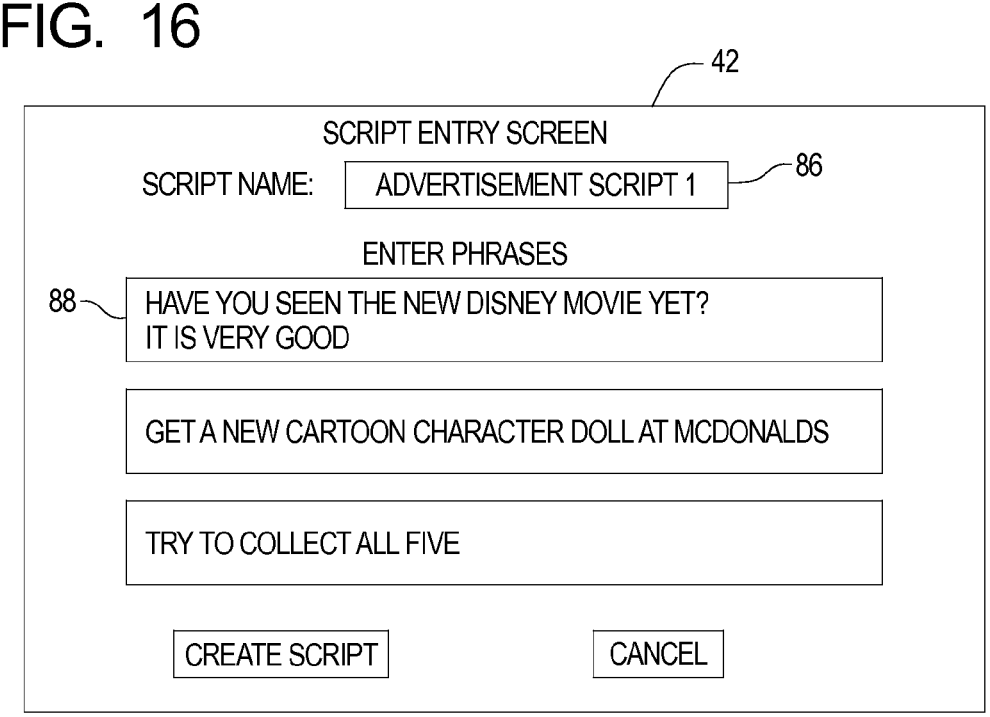
FIG. 16 is a script entry screen according to an alternative embodiment of the invention.

Although the first and second embodiments focus on healthcare applications, the system of the present invention may be used for any messaging application. For example, the system is particularly well suited for advertising. In a third embodiment of the invention, an advertising service is provided with a remote interface to the server for creating and assigning script programs which contain advertising messages. As shown in FIG. 16, each advertising message may be conveniently entered through script entry screen 42, like the health-related messages of the preferred embodiment. The operation of the third embodiment is analogous to the operation of the preferred embodiment, except that the talking toys communicate advertising messages rather than health-related messages.

Figure 17:
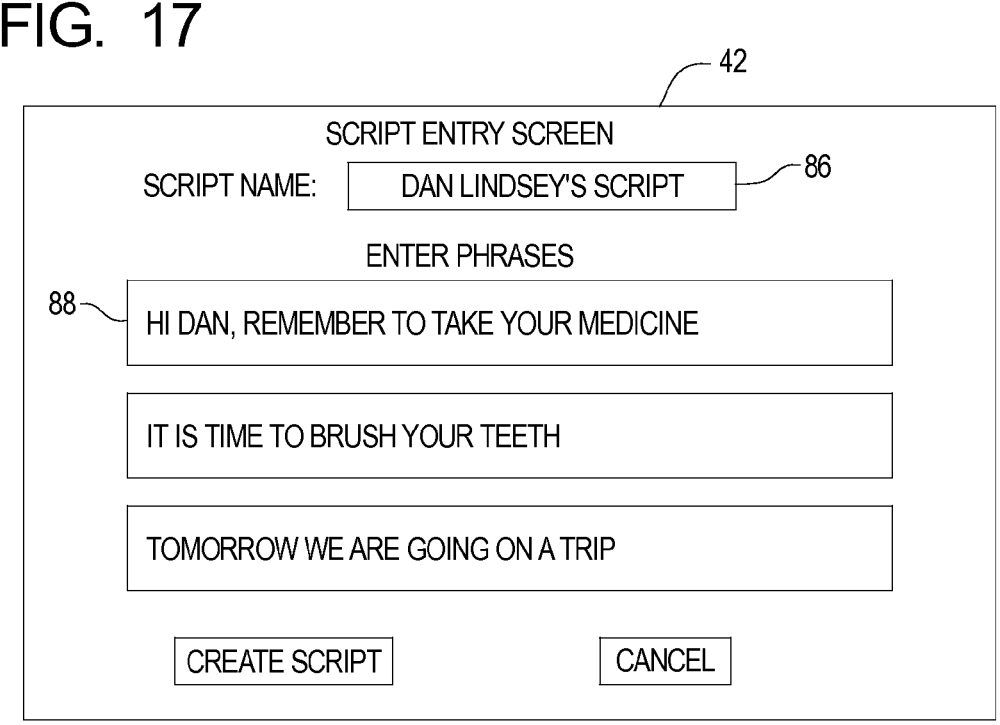
FIG. 17 is a script entry screen according to another embodiment of the invention.

Of course, the system of the present invention has many other applications. Typically, the user of each programmable toy is a child. In a fourth embodiment of the invention, the child's parent or guardian is provided with a remote interface to the server for creating and assigning script programs which contain messages for the child. As shown in FIG. 17, each message may be conveniently entered through script entry screen 42. The operation of the fourth embodiment is analogous to the operation of the preferred embodiment, except that script information is entered in the server by a parent or guardian rather than a healthcare provider.

Alternatively, the child may be provided with a remote interface to the server to create and assign his or her own script programs. It should also be noted that script programs may be generated from information received from multiple sources, such as a healthcare provider, an advertiser, and a parent. In a fifth embodiment of the invention, the script entry screen includes a respective section for each of the sources to enter a message to be communicated. Each of the sources is provided with a remote interface to the server and a password for accessing the script entry screen. After each source has entered one or more messages in the server, a script program is generated which contains a combination of health-related messages, advertisements, educational messages, or entertainment messages. The remaining operation of the fifth embodiment is analogous to the operation of the preferred embodiment described above.

Although the above description contains many specificities, these should not be construed as limitations on the scope of the invention but merely as illustrations of some of the presently preferred embodiments. Many other embodiments of the invention are possible. For example, the scripting language and script commands shown are representative of the preferred embodiment. It will be apparent to one skilled in the art many other scripting languages and specific script commands may be used to implement the invention.

Moreover, the programmable device need not be embodied as a doll. The toys may be embodied as action figures, robots, or any other type of toy. Further, each programmable toy need not include a control button for triggering speech output. In alternative embodiments, speech is triggered by other mechanisms, such as voice prompts, the absence of the user's voice, position sensitive sensors, switches, or the like. Specific techniques for triggering speech in a programmable toy are well known in the art. In addition, the system of the present invention is not limited to healthcare applications.

The system may be used in any application which involves the communication of messages, including advertising, education, or entertainment. Of course, various combinations of these applications are also possible. For example, messages from multiple sources may be combined to generate script programs which contain a combination of health-related messages, advertisements, or educational messages. Further, the system may include any number of remote interfaces for entering and assigning script programs, and any number of programmable toys for delivering messages.

More generally, the programmable device need not be a toy.

For example, the programmable device may be a handheld computing device adapted to control and monitor an athlete end user's performance during athletic training. The device may monitor the athlete end user's heart rate and lactose levels. The device may be remotely programmed by a trainer end user or automated system with instructions for training for a specific athletic event based on data collected by the handheld device.

The programmable device may be a house hold appliance such as a refrigerator that monitors its contents. A remote end user such as a service that delivers groceries could reprogram the refrigerator as necessary to reflect delivered goods.

The programmable device may also be an industrial motion control system such as a robotic welding machine. An engineer in charge of the product being welded may change its design and remotely generate a new command program for the robotic welding machine in response to the design changes.

The programmable device may be an HVAC system that communicates with a remote weather monitoring system that generates a new command program for the HVAC system in response to changes in the weather.

The embodiments of the present invention disclosed above are merely an illustrative, and not exhaustive, list of the environments in which the present invention may be applied. Therefore, the scope of the invention should be determined not by the examples given, but by the appended claims and their legal equivalents.

We claim:

1. System comprising:
a plurality of motion devices, where each motion device is associated with at least one device user and comprises
a motion system, where the motion system contains state data and motion data, where the motion system causes the motion device to move based on the motion data,
a data input system, where the at least one device user enters control data into the motion system using the data input system, and
a data output system, where the motion system communicates message data to the at least one device user using the data output system;
at least one server system, where
the server system comprises at least one server web page,
at least one system user is associated with each server system, and
the at least one system user generates message data associated with a given one of the plurality of motion devices using a web browser operatively connected to the at least one server web page; and
a communications network for communicating data between the at least one server system and each of the plurality of motion devices; whereby
the message data generated by the at least one server system is communicated to the given motion device through the communications network and communicated to the at least one device user associated with the given motion device by the data output system of the given motion device.

2. A system as recited in claim 1, in which the at least one device user associated with the given motion device enters control data using the data input system associated with the given motion device, where the control data alters the motion data to alter operation of the motion system associated with the given motion device.

3. A system as recited in claim 1, in which the system user generates the message data by selecting at least one user message from a plurality of predefined user messages stored by the at least one server system.

4. A system as recited in claim 3, in which the system user generates the message data by selecting a plurality of user messages from the plurality of predefined user messages.

5. A system as recited in claim 1, in which the motion device transfers state data to the at least one server system.

6. A system as recited in claim 1, in which the motion device transfers control data to the at least one server system.

7. A system comprising:
a plurality of motion devices, where each motion device is associated with at least one device user and comprises
a motion system, where the motion system causes movement of the motion device based on at least one motion script,
a data input system, where the at least one device user alters the at least one motion script using the data input system, and
a data output system, where the motion system communicates message data to the at least one device user using the data output system;
at least one server system, where
the server system comprises at least one server web page,
at least one system user is associated with each server system, and
the at least one system user generates message data associated with a given one of the plurality of motion devices using a web browser operatively connected to the at least one server web page, and
at least one motion script associated with the given one of the plurality of motion devices using the at least one server system; and
a communications network for communicating message data and motion scripts between the at least one server system and each of the plurality of motion devices; whereby
the message data generated by the at least one server system is communicated to the given motion device through the communications network and communicated to the at least one device user associated with the given motion device by the data output system of the given motion device.

8. A system as recited in claim 7, in which the at least one device user associated with the given motion device alters the motion script using the data input system associated with the given motion device to alter operation of the motion system associated with the given motion device.

9. A system as recited in claim 7, in which the system user generates the message data by selecting at least one user message from a plurality of predefined user messages stored by the at least one server system.

10. A system as recited in claim 7, in which the system user generates the message data by selecting a plurality of user messages from the plurality of predefined user messages.

11. A system as recited in claim 7, in which the motion device transfers data to the at least one server system.

12. A system as recited in claim 7, in which the motion device transfers message data to the at least one server system.

13. A system as recited in claim 7, in which:
the user enters message data using the data input system; and
the motion system sends the message data to the at least one server system.

* * * * *